US007544808B2

(12) United States Patent  
Weinstein et al.

(10) Patent No.: US 7,544,808 B2
(45) Date of Patent: Jun. 9, 2009

(54) TRICYCLIC MODULATORS OF THE GLUCOCORTICOID RECEPTOR, AP-1, AND/OR NF-κB ACTIVITY AND USE THEREOF

(75) Inventors: David S. Weinstein, East Windsor, NJ (US); John L. Gilmore, Yardley, PA (US); James Sheppeck, Newtown, PA (US); Bingwei Vera Yang, Belle Mead, NJ (US); Soong-Hoon Kim, Titusville, NJ (US); Wayne Vaccaro, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 53 days.

(21) Appl. No.: 11/773,506

(22) Filed: Jul. 5, 2007

(65) Prior Publication Data

US 2007/0270453 A1    Nov. 22, 2007

Related U.S. Application Data

(62) Division of application No. 11/035,176, filed on Jan. 13, 2005, now Pat. No. 7,253,283.

(60) Provisional application No. 60/537,469, filed on Jan. 16, 2004.

(51) Int. Cl.
 C07D 277/20 (2006.01)
 A61K 31/425 (2006.01)

(52) U.S. Cl. .............. 548/185; 548/233; 548/265.4; 548/332.5; 514/371; 514/377; 514/383; 514/398

(58) Field of Classification Search ............. 548/185, 548/233, 265.4, 332.5; 514/371, 377, 383, 514/398
 See application file for complete search history.

(56) References Cited

U.S. PATENT DOCUMENTS

| 3,317,387 | A | 5/1967 | Prichard et al. |
| 3,517,073 | A | 6/1970 | Fields |
| 4,786,646 | A | 11/1988 | Guthrie et al. |
| 5,055,468 | A | 10/1991 | Gray et al. |
| 5,202,486 | A | 4/1993 | Barrish et al. |
| 5,332,820 | A | 7/1994 | Duncia |
| 5,409,932 | A | 4/1995 | Schwenner et al. |
| 5,411,960 | A | 5/1995 | Schwenner et al. |
| 5,455,248 | A | 10/1995 | DeHaven-Hudkins et al. |
| 5,514,683 | A | 5/1996 | Kalindjian et al. |
| 5,569,655 | A | 10/1996 | Dority, Jr. et al. |
| 5,616,780 | A | 4/1997 | Pitteloud et al. |
| 6,214,915 | B1 | 4/2001 | Avakian et al. |
| 6,262,059 | B1 | 7/2001 | Pamukcu et al. |
| 6,291,679 | B1 | 9/2001 | Mailliet et al. |
| 6,995,181 | B2 | 2/2006 | Vaccaro et al. |
| 2004/0132758 | A1 | 7/2004 | Vaccaro et al. |
| 2005/0171136 | A1 | 8/2005 | Vaccaro et al. |
| 2005/0176716 | A1 | 8/2005 | Duan et al. |
| 2005/0176749 | A1 | 8/2005 | Yang et al. |
| 2005/0182082 | A1 | 8/2005 | Duan et al. |
| 2005/0182083 | A1 | 8/2005 | Weinstein et al. |
| 2005/0182110 | A1 | 8/2005 | Yang |
| 2006/0154962 | A1 | 7/2006 | Yang |
| 2006/0154973 | A1 | 7/2006 | Sheppeck et al. |
| 2006/0154975 | A1 | 7/2006 | Yang et al. |

FOREIGN PATENT DOCUMENTS

| CS | 198 678 | 11/1982 |
| DE | 197 42 014 | 3/1999 |
| EP | 0 405 436 | 11/1995 |
| WO | WO 93/16982 | 9/1993 |
| WO | WO 94/00421 | 1/1994 |
| WO | WO 95/05359 | 2/1995 |
| WO | WO 95/15947 | 6/1995 |
| WO | WO 99/15493 | 4/1999 |
| WO | WO 02/051851 | 7/2002 |
| WO | WO 03/007949 | 1/2003 |
| WO | WO 03/062241 | 7/2003 |
| WO | WO 03/101932 | 12/2003 |

(Continued)

OTHER PUBLICATIONS

Alibert, S. et al., "Synthesis and Effects on Chloroquine Susceptibility in *Plasmodium falciparum* of a Series of New Dihydroanthracene Derivatives", Journal of Medicinal Chemistry, vol. 45, No. 15, pp. 3195-3209 (2002).

(Continued)

*Primary Examiner*—Shailendra Kumar
(74) *Attorney, Agent, or Firm*—Laurelee A. Duncan; Terence Bogie

(57) ABSTRACT

Novel non-steroidal compounds are provided which are useful in treating diseases associated with modulation of the glucocorticoid receptor, AP-1, and/or NF-κB activity including obesity, diabetes, inflammatory and immune diseases, and have the structure of formula (I)

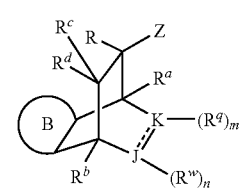

or stereoisomers or prodrugs or pharmaceutically acceptable salts thereof, wherein B, J, K, Z, R, $R^a$, $R^b$, $R^c$, $R^d$, $R^q$, $R^w$, m and n are defined herein. Also provided are pharmaceutical compositions and methods of treating obesity, diabetes and inflammatory or immune associated diseases comprising said compounds.

14 Claims, No Drawings

FOREIGN PATENT DOCUMENTS

| WO | WO 03/104195 | 12/2003 |
|----|--------------|---------|
| WO | WO 2004/000869 | 12/2003 |
| WO | WO 2004/005229 | 1/2004 |
| WO | WO 2004/009017 | 1/2004 |
| ZA | 681802 | 3/1968 |

OTHER PUBLICATIONS

Compounds (by Registry Number) with no references in the Chemical Abstracts file: 500280-08-0, 496959-82-1, 332907-97-8, 331751-07-6, 331427-65-7, 312317-98-9, 312315-55-2, 311331-77-8.

El-Zanfally, S. et al., "Reactions of Aminopyridines with some Inner Anhydrides", Egypt J. Pharm. Sci., vol. 17, No. 3, pp. 53-62 (1976).

Kotha, S. et al., "Synthesis of highly constrained unusual α-amino acid derivative by the Diels-Alder approach", Indian Journal of Chemistry, vol. 41B, pp. 2330-2332 (2002).

Pradines, B. et al., "In Vitro Increase in Chloroquine Accumulation Induced by Dihydroethano- and Ethenoanthracene Derivatives in *Plasmodium falciparum*-Parasitized Erythrocytes", Antimicrobial Agents and Chemotherapy, vol. 46, No. 7, pp. 2061-2068 (2002).

Baldwin, Jr., A.S., "The transcription factor NF-κB and human disease", The Journal of Clinical Investigation, vol. 107, No. 1, pp. 3-6 (2001).

Bradsher, C.K. et al., "Acridizinium Ion Chemistry. II. The Diels-Alder Reaction", Journal of the American Chemical Society, vol. 80, pp. 933-934 (1958).

Bradsher, C.K. et al., "Addition of Dienophiles to the Acridizinium Ion. III. Evidence for a Two-Step Reaction", The Journal of Organic Chemistry, vol. 34, No. 6, pp. 1700-1702 (1969).

Bradsher, C.K. et al., "Cationic Polar Cycloaddition of Cyclopropenes", J. Org. Chem., vol. 44, No. 8, pp. 1199-1202 (1979).

Bradsher, C.K. et al., "Possible Role of Charge-Transfer Complexes in Cationic Polar Cycloaddition", J. Org. Chem., vol. 43, No. 5, pp. 822-827 (1978).

Bradsher, C.K. et al., "Stereoselectivity Due to Electrostatic Repulsion in the Polar Cycloaddition of the Acridizinium Ion", J. Het. Chem., vol. 10, pp. 1031-1033 (1973).

Bradsher, C.K. et al., "Steric Effects in Some Cycloaddition Reactions", Journal of the American Chemical Society, vol. 99, No. 8, pp. 2588-2591 (1977).

Bradsher, C.K. et al., "The Nature of the Addition of Dienophiles to the Acridizinium Ion", The Journal of Organic Chemistry, vol. 33, No. 2, pp. 519-523 (1968).

Burke, J.R., "Targeting IκB kinase for the treatment of inflammatory and other disorders", Current Opinion in Drug Discovery & Development, vol. 6, No. 5, pp. 720-728 (2003).

Burnham, W.S. et al., "6,11-Dihydroacridizinium Derivatives Having a 6,11-Etheno Bridge", J. Org. Chem., vol. 37, No. 3, pp. 355-358 (1972).

Caldenhoven, E. et al., "Negative Cross-Talk between RelA and the Glucocorticoid Receptor: A Possible Mechanism for the Antiinflammatory Action of Glucocorticoids", Molecular Endocrinology, vol. 9, No. 4, pp. 401-412 (1995).

Chakravarti, D. et al., "Role of CBP/P300 in nuclear receptor signalling", Nature, vol. 383, pp. 99-103 (1996).

Diamond, M.I. et al., "Transcription Factor Interactions: Selectors of Positive or Negative Regulation from a Single DNA Element", Science, vol. 249, pp. 1266-1272 (1990).

Fields, D.L., "A Novel Synthesis of 2-Naphthols, Phenanthrols, Anthracenes, and Other Polycyclic Aromatic Products", J. Org. Chem., vol. 36, No. 20, pp. 3002-3005 (1971).

Fields, D.L. et al., "Azonia Polycyclic Quinones, *o*-Diazo-Oxides and Related Products", J. Het. Chem., vol. 7, pp. 91-97 (1970).

Fields, D.L. et al., "Cleavage Reactions of Bicyclic Ketones Derived from Azoniaanthracene-Ketene Acetal Adducts", J. Org. Chem., vol. 35, No. 6, pp. 1870-1875 (1970).

Fields, D.L. et al., "Diels-Alder Reactions Involving Azonia Polycyclic Aromatic Compounds and Nucleophilic Dienophiles", J. Org. Chem., vol. 33, No. 1, pp. 390-395 (1968).

Fields, D.L. et al., "Overcrowded Molecules. I. Substituted 8-*tert*-Butyl-1-(2-pyridyl)naphthalenes, Including a Thermodynamically Stable Ketonic Tautomer", J. Org. Chem., vol. 36, No. 20, pp. 2986-2990 (1971).

Fields, D.L. et al., "Overcrowded Molecules. II. 4,5-Bis(2-pyridyl)phenanthrene-3,6-diols", J. Org. Chem., vol. 36, No. 20, pp. 2991-2995 (1971).

Fields, D.L. et al., "Overcrowded Molecules. III. 13,14-Bis(2-pyridyl)pentaphene and Related Compounds", J. Org. Chem., vol. 36, No. 20, pp. 2995-3001 (1971).

Firestein, G.S. et al., "Signal Transduction and Transcription Factors in Rheumatic Disease", Arthritis & Rheumatism, vol. 42, No. 4, pp. 609-621 (1999).

Hart, H. et al., "1,4,5,8,9-pentamethylanthracene, Synthesis and Protonation", Tetrahedron Letters, vol. 16, No. 52, pp. 4639-4642 (1975).

Jackson, R.W. et al., "Benzobicyclooctanes as Novel Inhibitors of TNF-α Signaling", Bioorganic & Medicinal Chemistry Letters, vol. 12, pp. 1093-1097 (2002).

Jonat, C. et al., "Antitumor Promotion and Antiinflammation: Down-Modulation of AP-1 (Fos/Jun) Activity by Glucocorticoid Hormone", Cell, vol. 62, pp. 1189-1204 (1990).

Kamei, Y. et al., "A CBP Integrator Complex Mediates Transcriptional Activation and AP-1 Inhibition by Nuclear Receptors", Cell, vol. 85, pp. 403-414 (1996).

Manning, A.M. et al., "Targeting JNK for Therapeutic Benefit: From Junk to Gold", Nature Reviews Drug Discovery, vol. 2, pp. 554-565 (2003).

Miesfeld, R. et al., "Characterization of a steroid hormone receptor gene and mRNA in wild-type and mutant cells", Nature, vol. 312, pp. 779-781 (1984).

Parham, M.E. et al., "The Cycloaddition of the Acridizinium Ion with Norbornene Derivatives", J. Org. Chem., vol. 37, No. 3, pp. 358-362 (1972).

Peltz, G., "Transcription factors in immune-mediated disease", Current Opinion in Biotechnology, vol. 8, pp. 467-473 (1997).

Prostakov, N.S. et al., "Hydrogenation and halogenation of 6-phenyl-5-azabenzo[f]fluoranthene and reduction of its adducts with acrylonitrile", Khimiya Geterotsiklicheskikh Soedinenii, vol. 2, pp. 233-235 (1982), (Abstract only).

Reichardt, H.M. et al., "DNA Binding of the Glucocorticoid Receptor Is Not Essential for Survival", Cell, vol. 93, pp. 531-541 (1998).

Reichardt, H.M. et al., "Repression of inflammatory responses in the absence of DNA binding by the glucocorticoid receptor", The EMBO Journal, vol. 20, No. 24, pp. 7168-7173 (2001).

Weinberger, C. et al., "Domain structure of human glucocorticoid receptor and its relationship to the v*erb-A* oncogene product", Nature, vol. 318, pp. 670-672 (1985).

Weinberger, C. et al., "Identification of Human Glucocorticoid Receptor Complementary DNA Clones by Epitope Selection", Science, vol. 228, pp. 740-742 (1985).

Westerman, I.J. et al., "Rates of Addition to Styrene to 9-Substituted Acridizinium Ions", J. Org. Chem., vol. 36, No. 7, pp. 969-970 (1971).

Westerman, I.J. et al., "Regiochemistry of Polar Cycloaddition. Validity of the Electrophilic Addition Model", J. Org. Chem., vol. 43, No. 15, pp. 3002-3006 (1978).

Westerman, I.J. et al., "Stereochemistry of Cationic Polar Cycloaddition", J. Org. Chem., vol. 44, No. 5, pp. 727-733 (1979).

Yang-Yen, H.-F. et al., "Transcriptional Interference between c-Jun and the Glucocorticoid Receptor: Mutual Inhibition of DNA Binding Due to Direct Protein-Protein Interaction", Cell, vol. 62, pp. 1205-1215 (1990).

U.S. Appl. No. 11/330,749, filed Jan. 12, 2006, Bristol-Myers Squibb Co.

TRICYCLIC MODULATORS OF THE GLUCOCORTICOID RECEPTOR, AP-1, AND/OR NF-κB ACTIVITY AND USE THEREOF

This application is a divisional of U.S. Ser. No. 11/035,176, filed Jan. 13, 2005 now U.S. Pat. No. 7,253,283, which claims priority from U.S. Provisional Application No. 60/537,469, filed Jan. 16, 2004, incorporated in its entirety herein by reference.

FIELD OF THE INVENTION

The present invention relates to new non-steroidal compounds which are modulators of the glucocorticoid receptor, AP-1, and/or NF-κB activity and thus are useful in treating diseases such as obesity, diabetes and inflammatory or immune associated diseases, and to a method for using such compounds to treat these and related diseases.

BACKGROUND OF THE INVENTION

The transcription factors NF-κB and AP-1 are involved in regulating the expression of a number of genes involved in mediating inflammatory and immune responses. NF-κB regulates the transcription of genes including TNF-α, IL-1, IL-2, IL-6, adhesion molecules (such as E-selectin) and chemokines (such as Rantes), among others. AP-1 regulates the production of the cytokines TNF-α, IL-1, IL-2, as well as, matrix metalloproteases. Drug therapies targeting TNF-α, a gene whose expression is regulated by both NF-κB and AP-1, have been shown to be highly efficacious in several inflammatory human diseases including rheumatoid arthritis and Crohn's disease. Accordingly, NF-κB and AP-1 play key roles in the initiation and perpetuation of inflammatory and immunological disorders. See Baldwin, A S, *Journal of Clin. Investigation*, 107, 3 (2001); Firestein, G. S., and Manning, A. M., *Arthritis and Rheumatism*, 42, 609 (1999); and Peltz, G., *Curr. Opin, in Biotech.* 8, 467 (1997).

There are many signaling molecules (kinases and phosphatases) upstream of AP-1 and NF-κB which are potential therapeutic drug targets. The kinase JNK plays an essential role in regulating the phosphorylation and subsequent activation of c-jun, one of the subunits which constitute the AP-1 complex (fos/cjun). Compounds which inhibit JNK have been shown to be efficacious in animal models of inflammatory disease. See Manning A M and Davis R J, *Nature Rev. Drug Disc.*, V. 2, 554 (2003). A kinase critical to the activation of NF-κB is the IκB kinase (IKK). This kinase plays a key role in the phosphorylation of IκB. Once IκB is phosphorylated it undergoes degradation leading to the release of NF-κB which can translocate into the nucleus and activate the transcription of the genes described above. An inhibitor of IKK, BMS-345541, has been shown to be efficacious in animal models of inflammatory disease. See Burke J R., *Curr Opin Drug Discov Devel.*, Sep; 6(5), 720-8, (2003).

In addition to inhibiting signaling cascades involved in the activation of NF-κB and AP-1, the glucocorticoid receptor has been shown to inhibit the activity of NF-κB and AP-1 via direct physical interactions. The glucocorticoid receptor (GR) is a member of the nuclear hormone receptor family of transcription factors, and a member of the steroid hormone family of transcription factors. Affinity labeling of the glucocorticoid receptor protein allowed the production of antibodies against the receptor which facilitated cloning the glucocorticoid receptors. For results in humans see Weinberger, et al., *Science* 228, 640-742, (1985); Weinberger, et al., *Nature*, 318, 670-672 (1986) and for results in rats see Miesfeld, R., *Nature*, 312, 779-781, (1985).

Glucocorticoids which interact with GR have been used for over 50 years to treat inflammatory diseases. It has been clearly shown that glucocorticoids exert their anti-inflammatory activity via the inhibition by GR of the transcription factors NF-κB and AP-1. This inhibition is termed transrepression. It has been shown that the primary mechanism for inhibition of these transcription factors by GR is via a direct physical interaction. This interaction alters the transcription factor complex and inhibits the ability of NF-κB and AP-1 to stimulate transcription. See Jonat, C., et al., *Cell*, 62, 1189 (1990); Yang-Yen, H. F., et al., *Cell*, 62, 1205 (1990); Diamond, M. I. et al., *Science* 249, 1266 (1990); and Caldenhoven, E. et al., *Mol. Endocrinol.*, 9, 401 (1995). Other mechanisms such as sequestration of co-activators by GR have also been proposed. See Kamer Y, et al., *Cell*, 85, 403 (1996); and Chakravarti, D. et al., *Nature*, 383, 99 (1996).

In addition to causing transrepression, the interaction of a glucocorticoid with GR can cause GR to induce transcription of certain genes. This induction of transcription is termed transactivation. Transactivation requires dimerization of GR and binding to a glucocorticoid response element (GRE).

Recent studies using a transgenic GR dimerization defective mouse which cannot bind DNA have shown that the transactivation (DNA binding) activities of GR could be separated from the transrepressive (non-DNA binding) effect of GR. These studies also indicate that many of the side effects of glucocorticoid therapy are due to the ability of GR to induce transcription of various genes involved in metabolism, whereas, transrepression, which does not require DNA binding leads to suppression of inflammation. See Tuckermann, J. et al., *Cell*, 93, 531 (1998) and Reichardt, H M, *EMBO J.*, 20, 7168 (2001).

Additionally, tetrahydronaphthaleneamines and benzobicyclooctanes have been reported in the literature as having calcium ion channel activity and inhibiting cellular events involving TNF-α and IL-8, respectively. For example, U.S. Pat. No. 5,202,486; PCT application WO 02/051851; and Jackson et al., *Bioorg. Med. Chem. Lett.* 12 pp. 1093-1097 (2002). Also, PCT application WO 2004/009017 published Jan. 29, 2004 and assigned to Applicant, and incorporated herein by reference in its entirety, describes substituted bicyclooctanes useful in treating diseases such as obesity, diabetes and inflammatory or immune associated diseases.

Compounds that modulate AP-1 and/or NF-κB activity would be useful as such compounds would be useful in the treatment of inflammatory and immune diseases and disorders such as osteoarthritis, rheumatoid arthritis, multiple sclerosis, asthma, inflammatory bowel disease, transplant rejection and graft vs. host disease.

Also, with respect to the glucocorticoid receptor pathway, it is known that glucocorticoids are potent anti-inflammatory agents, however their systemic use is limited by side effects. Compounds that retain the anti-inflammatory efficacy of glucocorticoids while minimizing the side effects such as diabetes, osteoporosis and glaucoma would be of great benefit to a very large number of patients with inflammatory diseases.

Additionally concerning GR, the art is in need of compounds that antagonize transactivation. Such compounds may be useful in treating metabolic diseases associated with increased levels of glucocorticoid, such as diabetes, osteoporosis and glaucoma.

Additionally concerning GR, the art is in need of compounds that cause transactivation. Such compounds may be useful in treating metabolic diseases associated with a deficiency in glucocorticoid. Such diseases include Addison's disease.

It is believed that the compounds of the present invention as described below fill the above needs.

DESCRIPTION OF THE INVENTION

The present invention relates to new non-steroidal compounds which are modulators of the glucocorticoid receptor, AP-1, and/or NF-κB activity and thus are useful in treating diseases such as obesity, diabetes and inflammatory or immune associated diseases, and to a method for using such compounds to treat these and related diseases.

In one embodiment, the present invention is directed to novel compounds of Formula I below:

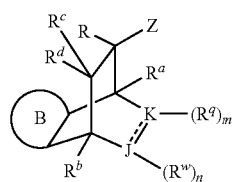

I including all stereoisomers thereof, or a prodrug thereof, or a pharmaceutically acceptable salt thereof, or a solvate thereof, wherein "≡≡≡" is a single or double bond;

m is 1 to 2;

n is 1 to 2;

J and K are the same or different and are independently selected from C, N, O or S;

R is independently selected from hydrogen, alkyl, alkenyl, alkynyl, alkoxy, cyano, aryl, arylalkyl, aryloxy, heteroaryl, cycloheteroalkyl, heteroarylalkyl, cycloheteroalkylalkyl, cycloalkyl, cycloalkylalkyl, cyanoalkyl, aminoalkyl, hydroxyalkyl, aryloxyalkyl, hydroxyaryl or $NR^1R^2$, wherein $R^1$ and $R^2$ are the same or different and are independently selected from hydrogen, alkyl, alkenyl, alkynyl, alkoxy, amino, cycloalkyl, cycloalkylalkyl, aryl, heteroaryl, heteroarylalkyl, cycloheteroalkyl, cycloalkenyl, monoalkylaminoalkyl, dialkylaminoalkyl, cycloheteroalkylalkyl, hydroxyaryl, aryloxyalkyl, alkoxyalkyl, hydroxyalkyl, or a heterocyclic ring;

$R^a$ is hydrogen, halo, alkyl, alkenyl, alkynyl, alkoxy, aryl, aryloxy, heteroaryl, cycloheteroalkyl, heteroarylalkyl, cycloheteroalkylalkyl, cyano, heteroarylaminocarbonyl, cycloheteroalkylcarbonyl, cyanoalkyl, alkylaminoalkyl, hydroxyalkyl, hydroxyaryl, alkoxyalkyl, aryloxyalkyl, nitro, amino, CHO, $CO_2$ alkyl, $CONR^eR^f$, $CH_2NR^gR^h$, $CO_2H$, $CH_2OH$, $CH_2NRH$, $NR^gR^h$, $NHCH_2R^g$, $NHCHR^gR^h$, $NHCOR^e$, $NHCONR^eR^f$ or $NHSO_2R^eR^f$, $R^b$ is hydrogen, alkyl, alkenyl, alkynyl, alkoxy, aryl, aryloxy, heteroaryl, cycloheteroalkyl, heteroarylalkyl, cycloheteroalkylalkyl, cyano, halo, heteroarylaminocarbonyl, cycloheteroalkylcarbonyl, cyanoalkyl, alkylaminoalkyl, hydroxyalkyl, alkoxyalkyl, nitro, amino, CHO, $CO_2$ alkyl, hydroxyaryl, aryloxyalkyl, $CONR^iR^j$, $CH_2NR^kR^l$, $CO_2H$, $CH_2OH$, $CH_2NHR^k$, $NHCH_2R^k$, $NR^kR^l$, $NHCHR^kR^l$, $NHCOR^i$, $NHCONR^iR^j$ or $NHSO_2R^i$;

$R^q$ and $R^w$ are the same or different and are independently selected from hydrogen, halo, hydroxy, alkyl, alkenyl, alkynyl, alkoxy, aryl, arylalkyl, aryloxy, heteroaryl, cycloheteroalkyl, heteroarylalkyl, cycloheteroalkylalkyl, cyano, heteroarylaminocarbonyl, cycloheteroalkylcarbonyl, cyanoalkyl, alkylaminoalkyl, hydroxyalkyl, hydroxyaryl, aryloxyalkyl, nitro, amino, CHO, $CO_2$ alkyl, $CONR^eR^f$, $CH_2NR^gR^h$, $CO_2H$, $CH_2OH$, $CH_2NHR^g$, $NR^gR^h$, $NHCH_2R^g$, $NHCHR^gR^h$, $NHCOR^e$, $NHCONR^eR^f$, $NHSO_2R^eR^f$, =O, =S, $SR^i$, $NHNR^kR^l$, $NHNR^kCO_2R^i$, $NHSO_2R^i$ or a heterocyclic ring;

where $R^e$ and $R^f$ are the same or different and are independently selected from hydrogen, aryl, alkyl, alkenyl, alkynyl, alkoxy, amino, alkoxyalkyl, alkylaminoalkyl, dialkylaminoalkyl, heteroaryl, cycloheteroalkyl, heteroarylalkyl, cycloheteroalkylalkyl, cycloalkyl, or cycloalkylalkyl, and $R^e$ and $R^f$ can be taken together with the nitrogen to which they are attached to form a 5-, 6- or 7-membered heteroaryl or cycloheteroalkyl ring which contains 1, 2 or 3 hetero atoms which can be N, O or S;

$R^g$ and $R^h$ are the same or different and are independently selected from hydrogen, aryl, alkyl, alkenyl, alkynyl, alkoxy, amino, alkoxyalkyl, alkylaminoalkyl, dialkylaminoalkyl, heteroaryl, cycloheteroalkyl, heteroarylalkyl, cycloheteroalkylalkyl, cycloalkyl, or cycloalkylalkyl, and $R^g$ and $R^h$ can be taken together with the nitrogen to which they are attached to form a 5-, 6- or 7-membered heteroaryl ring or cycloheteroalkyl ring which contains 1, 2 or 3 hetero atoms which can be N, O or S;

$R^i$ and $R^j$ are the same or different and are independently selected from hydrogen, aryl, alkyl, alkenyl, alkynyl, alkoxy, amino, alkoxyalkyl, alkylaminoalkyl, dialkylaminoalkyl, heteroaryl, cycloheteroalkyl, heteroarylalkyl, cycloheteroalkylalkyl, cycloalkyl, or cycloalkylalkyl, and $R^i$ and $R^j$ can be taken together with the nitrogen to which they are attached to form a 5-, 6-or 7-membered heteroaryl ring or cycloheteroalkyl ring which contains 1, 2 or 3 hetero atoms which can be N, O or S;

$R^k$ and $R^l$ are the same or different and are independently selected from hydrogen, aryl, alkyl, alkenyl, alkynyl, alkoxy, amino, alkoxyalkyl, alkylaminoalkyl, dialkylaminoalkyl, heteroaryl, cycloheteroalkyl, heteroarylalkyl, cycloheteroalkylalkyl, cycloalkyl, or cycloalkylalkyl, and $R^k$ and $R^l$ can be taken together with the nitrogen to which they are attached to form a 5-, 6- or 7-membered heteroaryl ring or cycloheteroalkyl ring which contains 1, 2 or 3 hetero atoms which can be N, O or S;

$R^c$ and $R^d$ are the same or different and are independently selected from hydrogen, alkyl, alkenyl, alkynyl, alkoxy, aryl, hydroxy, aryloxy, heteroaryl, cycloheteroalkyl, heteroarylalkyl, cycloheteroalkylalkyl, hydroxyaryl, or aryloxyalkyl;

$R^c$ and $R^d$ may optionally be taken together with the carbon to which they are attached to form a 3- to 7-membered ring which may optionally include an O atom or an N atom;

Z is independently selected from the group consisting of $CONR^1R^2$, $CH_2NR^1R^2$, $SONR^1R^2$ or $SO_2NR^1R^2$, wherein $R^1$ and $R^2$ are the same or different and are independently selected from hydrogen, alkyl, alkenyl, alkynyl, alkoxy, amino, cycloalkyl, cycloalkylalkyl, aryl, heteroaryl, heteroarylalkyl, cycloheteroalkyl, cycloalkenyl, monoalkylaminoalkyl, dialkylaminoalkyl, cycloheteroalkylalkyl, hydroxyaryl, aryloxyalkyl, alkoxyalkyl, hydroxyalkyl, or a heterocyclic ring; and B is an optionally substituted carbocyclic or heterocyclic ring.

Preferred compounds include the embodiments described in paragraphs 1-12, (below). Whether or not specifically listed, all preferred compounds described herein include prodrugs thereof, as well as stereoisomers thereof, a solvate thereof, or pharmaceutically acceptable salts thereof 1. A compound as defined in formula (I) (defined above) including all stereoisomers thereof, or a pharmaceutically acceptable salt thereof, or a solvate thereof, wherein J and K are the same or different and are independently selected from C or N;

R is independently selected from the group consisting of hydrogen, alkyl, alkenyl, alkynyl, alkoxy, aryl, arylalkyl, aryloxy, heteroaryl, cycloheteroalkyl, heteroarylalkyl, cycloheteroalkylalkyl, cycloalkyl, cycloalkylalkyl, cyanoalkyl, aminoalkyl, hydroxyalkyl, aryloxyalkyl, hydroxyaryl or $NR^1R^2$, wherein $R^1$ and $R^2$ are the same or different and are independently selected from hydrogen, alkyl, alkenyl, alkynyl, alkoxy, amino, cycloalkyl, cycloalkylalkyl, aryl, heteroaryl, heteroarylalkyl, cycloheteroalkyl, cycloalkenyl, monoalkylaminoalkyl, dialkylaminoalkyl, cycloheteroalkylalkyl, hydroxyaryl, aryloxyalkyl, alkoxyalkyl, hydroxyalkyl, or a heterocyclic ring;

Z is independently selected from the group consisting of $CONR^1R^2$, $CH_2NR^1R^2$ or $SO_2NR^1R^2$, wherein $R^1$ and $R^2$ are the same or different and are independently selected from hydrogen, alkyl, alkenyl, alkynyl, alkoxy, amino, cycloalkyl, cycloalkylalkyl, aryl, heteroaryl, heteroarylalkyl, cycloheteroalkyl, cycloalkenyl, monoalkylaminoalkyl, dialkylaminoalkyl, cycloheteroalkylalkyl, hydroxyaryl, aryloxyalkyl, alkoxyalkyl, hydroxyalkyl, or a heterocyclic ring; and B is an optionally substituted 6-membered carbocyclic ring.

2. A compound within the scope of the embodiment of paragraph number 1, including all stereoisomers thereof, or a pharmaceutically acceptable salt thereof, or a solvate thereof, wherein one of J and K is N and the other is C or N.

3. A compound within the scope of the embodiment of paragraph number 2, including all stereoisomers thereof, or a pharmaceutically acceptable salt thereof, or a solvate thereof, wherein the B ring has the structure

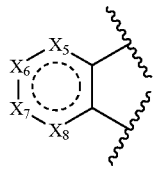

wherein:

$X_5$, $X_6$, $X_7$ and $X_8$ are the same or different and are independently selected from CH, $CH_2$, $CHR^{19}$, $CR^{20}$, $CR^{20}R^{21}$, N, NH, $NR^{22}$, O or S;

$R^{19}$, $R^{20}$, and $R^{21}$ are the same or different and are independently selected from halo, alkyl, aryl, cycloalkyl, heteroaryl, cycloheteroalkyl, hydroxy, alkoxy, aryloxy, cyano, nitro, $NR^eR^f$, CHO, —$CO_2$alkyl, hydroxyaryl, aryloxyalkyl, $OCONR^eR^f$, $OCOR^e$, $OCOOR^eR^f$, —OCO-aryl, —OCO-heteroaryl, $CONR^eR^f$, $CO_2H$, $OCSOR^eR^f$, $CSNR^eR^f$NHCOR$^i$, $NHCONR^eR^f$, $NHCSNR^eR^f$, $NHSO_pR^i$, —$SO_2NR^eR^f$, $NR^eSO_2NR^eR^f$, and $NR^eSO_pR^i$; and $R^{22}$ is selected from aryl, alkyl, alkenyl, alkynyl, alkoxy, amino, substituted amino, alkoxyalkyl, $CO_2$alkyl, C(O)alkyl alkylaminoalkyl, dialkylaminoalkyl, heteroaryl, cycloheteroalkyl, heteroarylalkyl, cycloheteroalkylalkyl, cycloalkyl, and cycloalkylalkyl.

4. A compound within the scope of the embodiment of paragraph number 3, including all stereoisomers thereof, or a pharmaceutically acceptable salt thereof, or a solvate thereof, having the structure

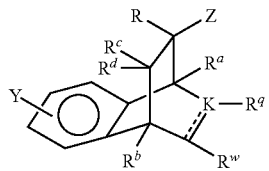

A wherein K is N or C and Y is hydrogen, alkyl, aryl, arylalkyl, heteroaryl, heteroarylalkyl, halo, or alkoxy.

5. A compound within the scope of the embodiment of paragraph number 4, including all stereoisomers thereof, or a pharmaceutically acceptable salt thereof, or a solvate thereof, having the structure

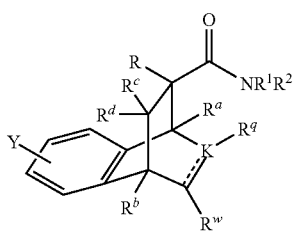

BB including all stereoisomers thereof, or a pharmaceutically acceptable salt thereof, or a solvate thereof, wherein K is N or C and Y is hydrogen, alkyl, aryl, arylalkyl, heteroaryl, heteroarylalkyl, halo, or alkoxy.

6. A compound within the scope of the embodiment of paragraph numbers 5, including all stereoisomers thereof, or a pharmaceutically acceptable salt thereof, or a solvate thereof, where R is hydrogen, alkyl or hydroxyalkyl;

$R^a$ is selected from hydrogen, halo, alkyl, CN, $NO_2$, $NH_2$, CHO, $CO_2$ alkyl, $CONR^eR^f$, $NR^gR^h$ or $CH_2NR^gR^h$;

$R^b$ is selected from hydrogen, halo, alkyl, CN, $NO_2$, $NH_2$, CHO, $CO_2$ alkyl, $CONR^iR^j$, $NR^kR^l$ or $CH_2NR^kR^l$;

$R^q$ is hydrogen, halo, alkyl, aryl, arylalkyl, heteroaryl, heteroarylalkyl, CN, $NO_2$, $NH_2$, CHO, $CO_2$ alkyl, $CONR^eR^f$, $NR^gR^h$ or $CH_2NR^gR^h$;

$R^w$ is hydrogen, hydroxy, alkyl, aryl, arylalkyl, heteroaryl, heteroarylalkyl, cyano, halo, nitro, amino, =O, =S, $SR^i$, CHO, $CO_2$ alkyl, $CONR^iR^j$, $CH_2NR^kR^l$, $NR^kR^l$, $NHNR^kR^l$, $NHNR^kCO_2R^i$, or a heterocyclic ring;

$R^cC$ and $R^d$ are the same or different and are independently selected from hydrogen, alkyl, or hydroxy; and Y is selected from hydrogen, halo or alkyl.

7. A compound within the scope of the embodiment of paragraphs number 6, including all stereoisomers thereof, or a pharmaceutically acceptable salt thereof, or a solvate thereof, wherein R is hydrogen or alkyl; $R^a$ is hydrogen; $R^b$ is independently hydrogen or alkyl; $R^cC$ and $R^d$ are each hydrogen; and Y is hydrogen or alkyl.

8. A compound within the scope of the embodiment of paragraph number 5, including all stereoisomers thereof, or a pharmaceutically acceptable salt thereof, or a solvate thereof, having a structure of formula C:

C

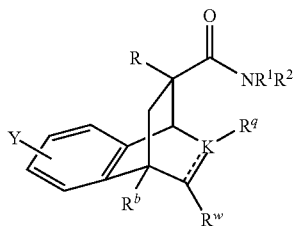

including all stereoisomers thereof, or a pharmaceutically acceptable salt thereof, or a solvate thereof, wherein R is hydrogen, alkyl, or hydroxyalkyl;

$R^b$ is selected from hydrogen, halo, alkyl, CN, $NO_2$, $NH_2$, CHO, $CO_2$ alkyl, $CONR^iR^j$, $NR^kR^l$ or $CH_2NR^kR^l$;

$R^q$ is hydrogen, halo, alkyl, aryl, arylalkyl, heteroaryl, heteroarylalkyl, CN, $NO_2$, $NH_2$, CHO, $CO_2$ alkyl, $CONR^eR^f$, $NR^gR^h$ or $CH_2NR^gR^h$;

$R^w$ is hydrogen, hydroxy, alkyl, aryl, arylalkyl, heteroaryl, heteroarylalkyl, cyano, halo, nitro, amino, =O, =S, $SR^i$, CHO, $CO_2$ alkyl, $CONR^iR^j$, $CH_2NR^kR^l$, $NR^kR^l$, $NHNR^kR^l$, $NHNR^kCO_2R^i$, or a heterocyclic ring;

one of $R^1$ and $R^2$ is heteroaryl; and

Y is selected from hydrogen, halo or alkyl.

9. A compound within the scope of the embodiment of paragraph number 5, including all stereoisomers thereof, or a pharmaceutically acceptable salt thereof, or a solvate thereof, wherein R is hydrogen or alkyl;

$R^b$ is selected from hydrogen, halo, alkyl, CN, $NO_2$, $NH_2$, CHO, $CO_2$ alkyl, $CONR^iR^j$, $NR^kR^l$ or $CH_2NR^kR^l$;

$R^q$ is hydrogen, halo, alkyl, aryl, arylalkyl, heteroaryl, heteroarylalkyl, CN, $NO_2$, $NH_2$, CHO, $CO_2$ alkyl, $CONR^eR^f$, $NR^gR^h$ or $CH_2NR^gR^h$;

$R^w$ is hydrogen, hydroxy, alkyl, aryl, arylalkyl, heteroaryl, heteroarylalkyl, cyano, halo, nitro, amino, =O, =S, $SR^i$, CHO, $CO_2$ alkyl, $CONR^iR^j$, $CH_2NR^kR^l$, $NR^kR^l$, $NHNR^kR^l$, $NHNR^kCO_2R^i$, or a heterocyclic ring;

one of $R^1$ and $R^2$ is

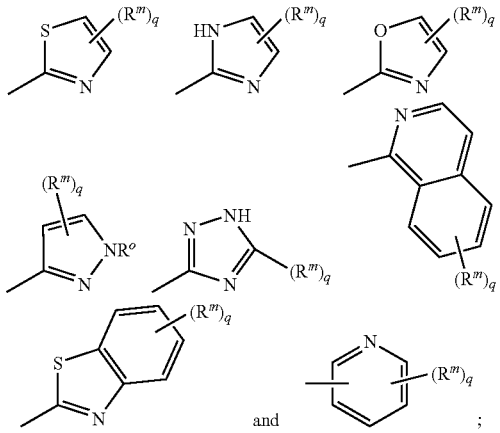

$R^m$ at each occurrence is independently selected from hydrogen, halogen, nitro, cyano, hydroxyl, alkoxy, $-CO_2$(alkyl), $-C(O)N(alkyl)_2$, alkyl, heteroarylalkyl, arylalkyl, aryl and heteroaryl;

$R^o$ is hydrogen or alkyl;

q is 1 or 2; and

Y is selected from hydrogen, halo or alkyl.

10. A compound within the scope of the embodiment of paragraph number 9, including all stereoisomers thereof, or a pharmaceutically acceptable salt thereof, or a solvate thereof, wherein R is alkyl;

$R^b$ is hydrogen or alkyl;

$R^q$ is hydrogen, alkyl, aryl, arylalkyl, heteroaryl, or heteroarylalkyl;

$R^w$ is hydrogen, hydroxy, alkyl, aryl, arylalkyl, heteroaryl, heteroarylalkyl, =O, =S, $SR^i$, $NR^kR^l$, $NHNR^kR^l$, $NHNR^kCO_2R^i$, or a heterocyclic ring;

one of $R^1$ and $R^2$ is

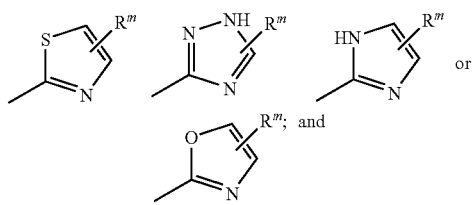

Y is hydrogen or alkyl.

11. A compound within the scope of formula (I), including all stereoisomers thereof, or a pharmaceutically acceptable salt thereof, or a solvate thereof, wherein

D

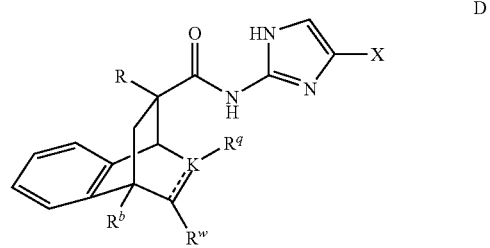

including all stereoisomers thereof, or a pharmaceutically acceptable salt thereof, or a solvate thereof, where K is N or C; R is alkyl; $R^b$ is hydrogen or alkyl; $R^q$ is hydrogen, alkyl, or arylalkyl; $R^w$ is hydroxy, =O, =S, $SR^i$, $NR^kR^l$, $NHNR^kR^l$, $NHNR^kCO_2R^i$, or a heterocyclic ring; and X is aryl, arylalkyl, alkyl, heteroaryl, or heteroarylalkyl; or

E

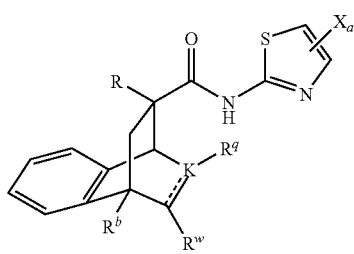

including all stereoisomers thereof, or a pharmaceutically acceptable salt thereof, or a solvate thereof, where K is N or C; R is alkyl; $R^b$ is hydrogen or alkyl; $R^q$ is hydrogen, alkyl, or arylalkyl; $R^w$ is hydroxy, =O, =S, $SR^i$, $NR^kR^l$, $NHNR^kR^l$, NHNR$^k$CO$_2$R$^i$, or a heterocyclic ring; and X$_a$ is aryl, arylalkyl, alkyl, heteroaryl, heteroarylalkyl or halo; or

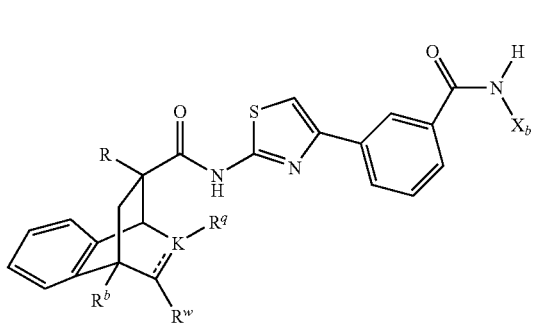

F including all stereoisomers thereof, or a pharmaceutically acceptable salt thereof, or a solvate thereof, where K is N or C; R is alkyl; R$^b$ is hydrogen or alkyl; R$^q$ is hydrogen, alkyl, or arylalkyl; R$^w$ is hydroxy, =O, =S, SR$^i$, NR$^k$R$^l$, NHNR$^k$R$^l$, NHNR$^k$CO$_2$R$^i$, or a heterocyclic ring; and X$_b$ is aryl, arylalkyl, alkyl, heteroaryl, heteroarylalkyl or halo; or

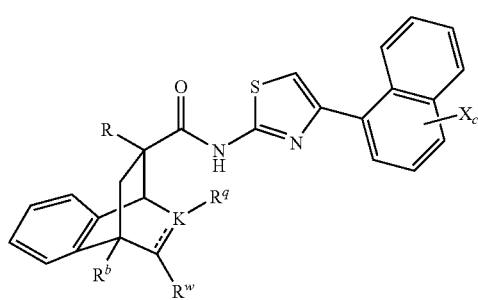

G including all stereoisomers thereof, or a pharmaceutically acceptable salt thereof, or a solvate thereof, where K is N or C;

R is alkyl;

R$^b$ is hydrogen, CO$_2$ alkyl, nitro, cyano, formyl, cycloheteroalkylcarbonyl, alkylaminoalkyl or amino;

R$^q$ is hydrogen, alkyl, or arylalkyl;

R$^w$ is hydroxy, =O, =S, SR$^i$, NR$^k$R$^l$, NHNR$^k$R$^l$, NHNR$^k$CO$_2$R$^i$, or a heterocyclic ring; and X$_c$ is hydrogen, alkyl or halo; or

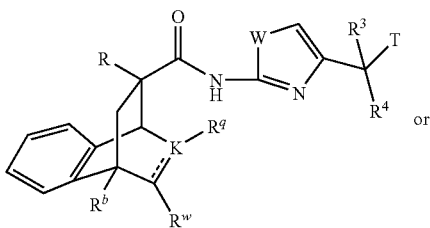

H including all stereoisomers thereof, or a pharmaceutically acceptable salt thereof, or a solvate thereof, where W is S or NH; K is N or C; R is alkyl; R$^b$ is H, alkyl, nitro, formyl, CO$_2$alkyl, amino, halo, and CN; R$^q$ is hydrogen, alkyl, or arylalkyl; R$^w$ is hydroxy, =O, =S, SR$^i$, NR$^k$R$^l$, NHNR$^K$R$^l$, NHNR$^k$CO$_2$R$^i$, or a heterocyclic ring; and X$_a$ is aryl, arylalkyl, alkyl, heteroaryl, heteroarylalkyl or halo;

T is a cycloalkyl, cycloalkenyl, heterocycloalkyl, aryl, or heteroaryl ring, each ring substituted by 0-4 R$^5$ and 0-1 R$^6$;

R$^3$ and R$^4$ are independently at each occurrence hydrogen, halogen, hydroxy, alkyl, alkenyl, alkynyl, alkoxy, cyano, nitro, NR$^e$R$^f$, or CHO provided that if M is CR$^m$, X is S, and either of R$^3$ and R$^4$ is alkyl, alkenyl, or alkynyl, then the other of R$^3$ and R$^4$ is not alkyl, alkenyl, or alkynyl;

or R$^3$ and R$^4$ combine to form =O or a =C, wherein the carbon of =C is substituted by hydrogen, aryl, alkyl, alkenyl, alkynyl, alkoxy, amino, substituted amino, alkoxyalkyl, alkylaminoalkyl, dialkylaminoalkyl, heteroaryl, cycloheteroalkyl, heteroarylalkyl, cycloheteroalkylalkyl, cycloalkyl, or cycloalkylalkyl; and R$^5$ and R$^6$ are, independently at each occurrence, hydrogen, halogen, hydroxy, alkyl, alkenyl, alkynyl, alkoxy, aryl, aryloxy, heteroaryl, cycloheteroalkyl, heteroarylalkyl, cycloheteroalkylalkyl, cyano, heteroarylaminocarboyl, cycloheteroalkylcarbonyl, cyanoalkyl, alkylaminoalkyl, hydroxyalkyl, hydroxyaryl, aryloxyalkyl, nitro, oxo, NR$^e$R$^f$, CHO, CO$_2$ alkyl, hydroxyaryl, aryloxyalkyl, CONR$^e$R$^f$, CH$_2$NR$^e$R$^f$, CO$_2$H, CH$_2$OH, CH$_2$NHC(O)R$^e$R$^f$, NHCOR$^i$, NHCONR$^e$R$^f$, NHSO$_p$R$^i$, —SO$_2$NR$^e$R$^f$, NR$^e$SO$_2$NR$^e$R$^f$, or NR$^e$SO$_p$R$^i$;

or R$^5$ and R$^6$ located on adjacent atoms can be taken together to form an optionally substituted cycloalkyl, aryl, heteroaryl, or cycloheteroalkyl ring.

12. A compound within the scope of the embodiment of paragraph number 11, including all stereoisomers thereof, or a pharmaceutically acceptable salt thereof, or a solvate thereof, having the structure:

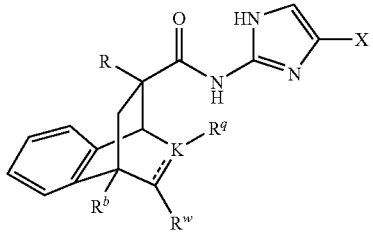

D including all stereoisomers thereof, or a pharmaceutically acceptable salt thereof, or a solvate thereof, where K is N or C; R is CH$_3$; R$^b$ is hydrogen or CH$_3$; R$^q$ is hydrogen, CH$_3$, C$_2$H$_5$, or benzyl; R$^w$ is hydroxy, =O, =S, SCH$_3$, NHC$_3$H$_7$, NHNH(C$_6$H$_5$), NHNHCO$_2$C$_2$H$_5$ or dioxolanyl; and X is 1-naphthyl, 1-(4-methyl)naphthyl, 1-(4-fluoro)naphthyl, 1-(6-methoxy) naphthyl, benzyl, or phenyl, t-butyl; or

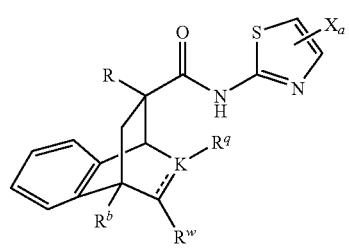

E including all stereoisomers thereof, or a pharmaceutically acceptable salt thereof, or a solvate thereof, where K is N or C; R is $CH_3$; $R^b$ is hydrogen or $CH_3$; R is hydrogen, $CH_3$, $C_2H_5$, or benzyl; $R^w$ is hydroxy, =O, =S, $SCH_3$, $NHC_3H_7$, NHNH($C_6H_5$), $NHNHCO_2C_2H_5$ or dioxolanyl; and $X_a$ is phenyl, benzyl, t-butyl, 1-naphthyl, 1-(4-fluoro)naphthyl, benzthiophen-3-yl, 1-(4-methyl)naphthyl, 1-(2-methoxy)naphthyl, 1-(6-methoxy)naphthyl, 3-fluorophenyl, 4-fluorophenyl, 3-methylphenyl, 2-chlorophenyl, 1-(4-methoxy)naphthyl, 1-(4-bromo)naphthyl, 1-(4-iodo)naphthyl, 5-anthracenyl, 1-anthracenyl, 4-quinolin-1-yl 2-quinolin-1-yl, 1-(4-cyano)naphthyl, 5-iodo, 4-benzthiophenyl, 1-(2-hydroxy)naphthyl, 1-(6-hydroxy)naphthyl, 1-(4-hydroxy)naphthyl; or

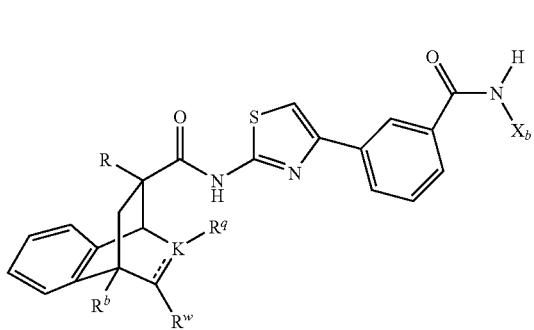

F including all stereoisomers thereof, or a pharmaceutically acceptable salt thereof, or a solvate thereof, where K is N or C; R is $CH_3$; $R^b$ is hydrogen or $CH_3$; $R^q$ is hydrogen, $CH_3$, $C_2H_5$, or benzyl; $R^w$ is hydroxy, =O, =S, $SCH_3$, $NHC_3H_7$, NHNH($C_6H_5$), $NHNHCO_2C_2H_5$ or dioxolanyl; and $X_b$ is phenyl, 3-methoxyphenyl, 4-methoxyphenyl, 2,5-dimethoxyphenyl, 3,5-dimethoxyphenyl, 3-pyridyl, 2-(4-pyridyl)ethyl, 2-(4-imidazolyl)ethyl, 3-chloro-4-methoxyphenyl, 3-hydroxy-4-methoxyphenyl, 3-fluoro-4-methoxyphenyl, 3,4,5-trimethoxyphenyl, 3,4-dimethoxyphenyl, 4-methyl-3-methoxyphenyl, 3-methoxyphenyl, 3,5-dimethoxyphenyl, 2,3-dimethoxyphenyl, 4-chlorophenyl, 2-napthyl, 3-chlorophenyl, 3,4-dichlorophenyl, 4-azidophenyl, 2,4-dimethoxyphenyl, 3-ethoxyphenyl, 3-(methylthio)phenyl, 4-(methylthio)phenyl, 3-(acetylenyl)phenyl, 4-methoxy-3-pyridyl, 3-cyanophenyl, 2-methyl-4-methoxyphenyl, 3-azidophenyl, 3-methyl-isothiazolyl, 1-methyl-pyrazol-5-yl, 5-trifluoromethyl-1,3,4-thiadiazol-2-yl; or

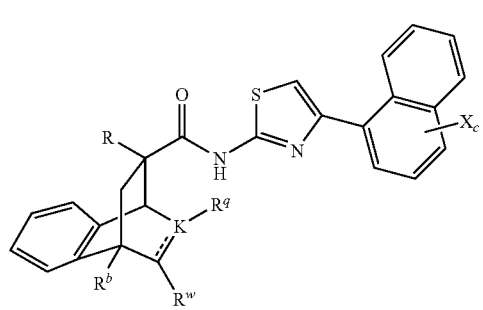

G including all stereoisomers thereof, or a pharmaceutically acceptable salt thereof, or a solvate thereof, where K is N or C; R is $CH_3$; $R^b$ is hydrogen or $CH_3$; $R^q$ is hydrogen, $CH_3$, $C_2H_5$, or benzyl; $R^w$ is hydroxy, =O, =S, $SCH_3$, $NHC_3H_7$, NHNH($C_6H_5$), $NHNHCO_2C_2H_5$ or dioxolanyl; and $X_c$ is hydrogen, $CH_3$, or F; or

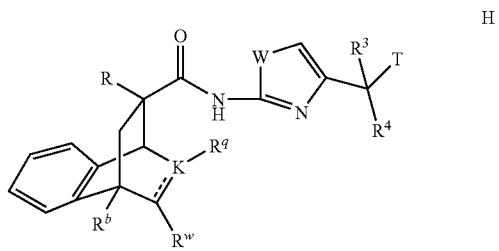

H including all stereoisomers thereof, or a pharmaceutically acceptable salt thereof, or a solvate thereof, where W is S or NH; K is N or C; R is alkyl; $R^b$ is H, $C_{1-4}$alkyl, halo, and CN; $R^q$ is hydrogen, alkyl, or arylalkyl; $R^w$ is hydroxy, =O, =S, $SR^i$, $NR^kR^l$, $NHNR^kR^l$, $NHNR^kCO_2R^i$, or a heterocyclic ring; and $X_a$ is aryl, arylalkyl, alkyl, heteroaryl, heteroarylalkyl or halo; W is S or NH; Q is CH;

T is a phenyl, naphthyl, pyrimidyl, pyridinyl, pyridazinyl, piperazinyl, thiophenyl, thiazolyl, isoxazolyl, or imidazolyl ring;

$R^3$ is hydrogen, halogen, or hydroxy; and $R^4$ is hydrogen, halogen, hydroxy, alkyl, alkenyl, alkynyl, alkoxy, cyano, nitro, $NR^eR^f$, or CHO;

or $R^3$ and $R^4$ combine to form =O or a double bond, wherein the double bond is substituted by hydrogen, aryl, alkyl, alkenyl, alkynyl, alkoxy, amino, substituted amino, alkoxyalkyl, alkylaminoalkyl, dialkylaminoalkyl, heteroaryl, heterocycloalkyl, heteroarylalkyl, heterocycloalkylalkyl, cycloalkyl, or cycloalkylalkyl;

$R^5$ and $R^6$ are independently at each occurrence:

(a) hydrogen, bromo, chloro, fluoro, $C_{1-4}$alkyl, arylalkyl, $OR^7$, oxo, $NO_2$, cyano, $NH_2$, —$NHC_{1-4}$alkyl, —$N(C_{1-4}alkyl)_2$, $SO_2C_{1-4}$alkyl, —$NHC(O)C_{1-4}$alkyl, —$C(O)N(C_{1-4}alkyl)_2$, —$C(O)NH(C_{1-4}alkyl)$, —$C(O)NH_2$, $CO_2H$, —$CO_2(C_{1-4}alkyl)$, arylalkyl; or (b) a phenyl, naphthyl, pyrazolyl, pyrimidinyl, pyridinyl, isoxazolyl, indolyl, or morpholinyl ring; each of which is optionally further substituted by 1-3 $R^8$;

or $R^5$ and $R^6$ located on adjacent atoms can be taken together to form a dioxole or phenyl ring, where each ring is optionally further substituted;

$R^7$ at each occurrence is selected from hydrogen, $C_{1-4}$alkyl, $(CH_2)_vC(O)NH_2$, $(CH_2)_v$heteroaryl, $(CH_2)_vO(CH_2)_y$, $O(CH_2)_zOR^9$, $(CH_2)_vN(C_{1-4}alkyl)_2$, $(CH_2)_v$heterocycloalkyl, or $(CH_2)_v$phenyl;

$R^8$ is halogen, oxo, $NH_2$, hydroxy, $C_{1-4}$alkyl, $C_{1-4}$alkoxy, —$(CH_2)$aryl, or heterocycloalkyl;

$R^9$ is hydrogen or $C_{1-4}$alkyl;

and v, y and z are independently at each occurrence selected from 0, 1 or 2.

13. A compound within the scope of the embodiment of paragraph number 12, including all stereoisomers thereof, or a pharmaceutically acceptable salt thereof, or a solvate thereof, having the structure:

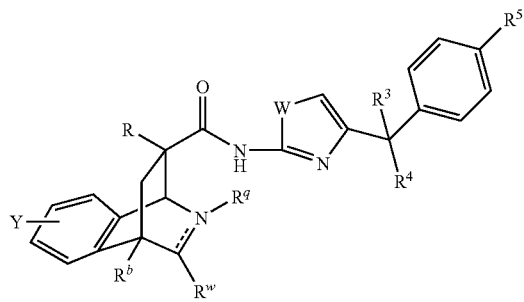

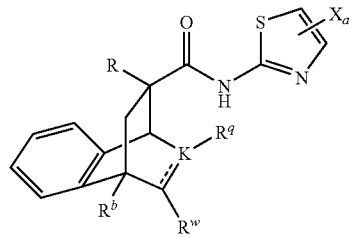

including all stereoisomers thereof, or a pharmaceutically acceptable salt thereof, or a solvate thereof, where Y is H or $CH_3$; R is $CH_3$, $C_2H_5$ or 2-hydroxyethyl; $R^b$ is H, $CH_3$, Cl, Br, and CN; W is S or NH; $R^3$ and $R^4$ are independently hydrogen, halogen, or hydroxy; or $R^3$ and $R^4$ combine to form =O. $R^5$ is hydrogen, $C_{1-4}$alkoxy; halogen, pyrimidine, isoxazole, pyrazole, or pyridine, where the $C_{1-4}$alkoxy; halogen, pyrimidine, isoxazole, pyrazole, or pyridine groups are substituted by hydrogen, morpholinyl, $C_{1-4}$alkoxy, or $C_{1-4}$alkyl.

14. A compound within the scope of the embodiment of paragraph number 13, including all stereoisomers thereof, or a pharmaceutically acceptable salt thereof, or a solvate thereof, having the structure:

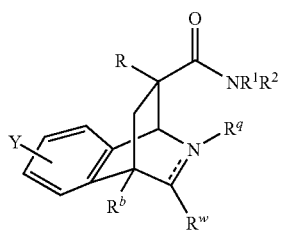

including all stereoisomers thereof, or a pharmaceutically acceptable salt thereof, or a solvate thereof, where Y is H or $CH_3$; R is $CH_3$, $C_2H_5$ or 2-hydroxyethyl; $R_b$ is hydrogen or $CH_3$; and one of $R^1$ and $R^2$ is H and the other of $R^1$ and $R^2$ is benzothiazol-2-yl, alkylbenzothiazol-2-yl, alkoxybenzothiazol-2-yl, halobenzothiazol-2-yl, thiazol-2-yl, 4-(1-naphthyl) thiazol-2-yl, 2-quinolin-1-yl, or a thiazole which is optionally substituted with heteroarylthio, heteroaryl, dialkyl, alkyl, aryl where the aryl may be optionally substituted with halo, alkyl, nitro, hydroxy, alkoxy, dialkoxy, carboxy, alkylaminocarbonyl, arylaminocarbonyl, hydroxyalkylaminocarbonyl, cycloheteroalkylcarbonyl, alkoxyalkylaminocarbonyl, heteroarylaminocarbonyl.

15. A compound within the scope of the embodiment of paragraph number 14, including all stereoisomers thereof, or a pharmaceutically acceptable salt thereof, or a solvate thereof, wherein including all stereoisomers thereof, or a pharmaceutically acceptable salt thereof, or a solvate thereof, where $X_a$ is 4,5-dimethyl, 5-chloro, 4-methyl, 5-methyl, 4-phenyl, 4-(1-naphthyl), 4-(2-naphthyl), 4-(4-fluoronaphth-1-yl), 4-(4-methylnaphth-1-yl), 4-(3-nitrophenyl), 4-(6-hydroxynaphth-1-yl), 4-[(1,2,4-triazol-5-yl)thio]methyl, 4-benzoic acid, 4-(4-bromonaphth-1-yl), 4-(N-ethyl)benzamide, 4-(N-2-methoxyphenyl)benzamide, 4-(N-methyl-N-2-hydroxyethyl)benzamide, 4-(N-(pyrrolidinyl)benzamide, 4-(N-morpholinyl)benzamide, 4-(N-phenyl-N-methyl)benzamide, 3-(N-ethyl)benzamide, 3-(N-2-methoxyphenyl)benzamide, 3-(N-2-methoxyethyl)benzamide, 3-(N-methyl-N-2-hydroxyethyl)benzamide, 3-(N-methyl-N-phenyl)benzamide, 3-(N-4-acetylpiperaziny-1-yl)benzamide, 3-(N-3-methoxypropyl)benzamide, 2-(6-carboxy)pyridine, 3-(N-3-hydroxy-4-methoxyphenyl)benzamide, 3-(N-3-fluoro-4-methoxyphenyl)benzamide, 3-(N-2,3-dimethoxyphenyl) benzamide, 3-(N-3-dimethoxyphenyl)benzamide, 3-(N-5-trifluormethyl-1,3,4-thiadiazol-2-yl)benzamide, 3-(N-5-methyl-1,3,4-thiadiazol-2-yl)benzamide, 3-(N-5-chlorobenzoxazol-2-yl)benzamide, 3-(N-3-benzonitrile) benzamide, 3-(N-4-methoxypyrid-3-yl)benzamide, 5-(1,4-benzodioxane), 4-(1,3-benzodioxole).

16. A compound having the structure:

(i)

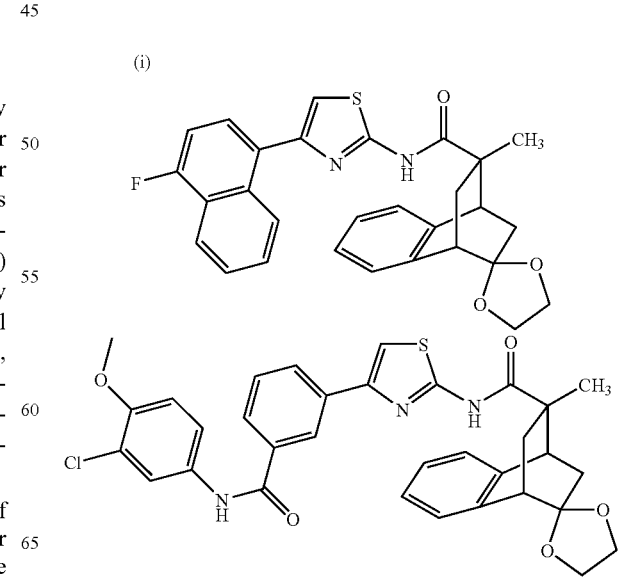

-continued
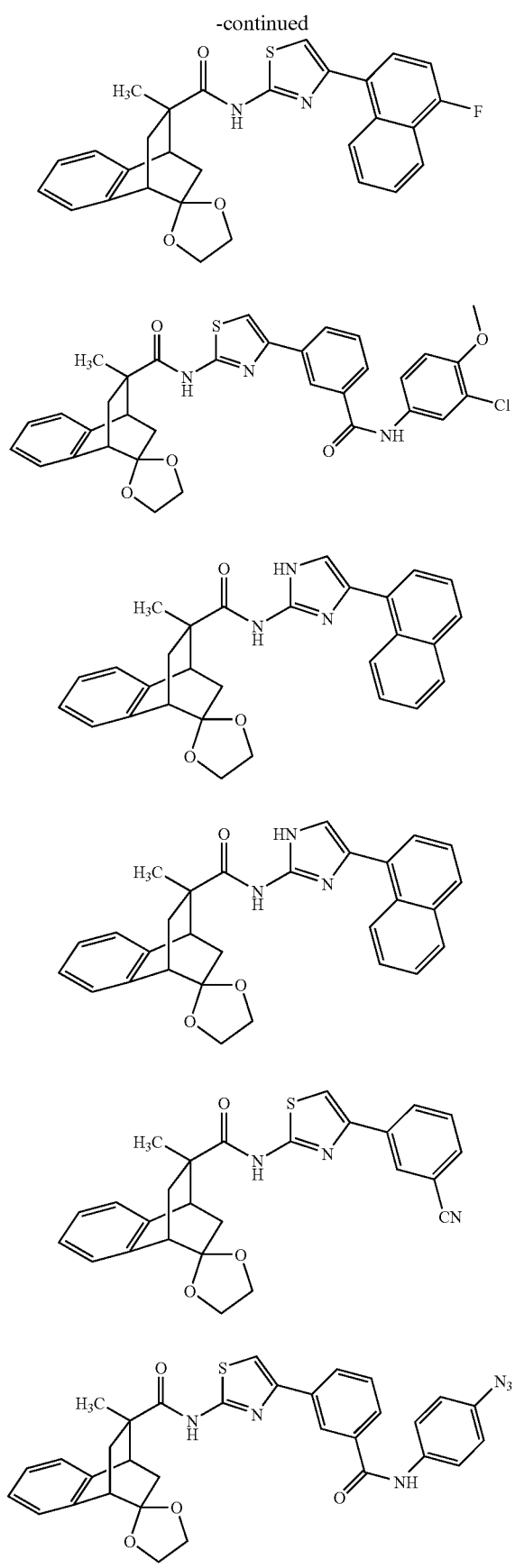
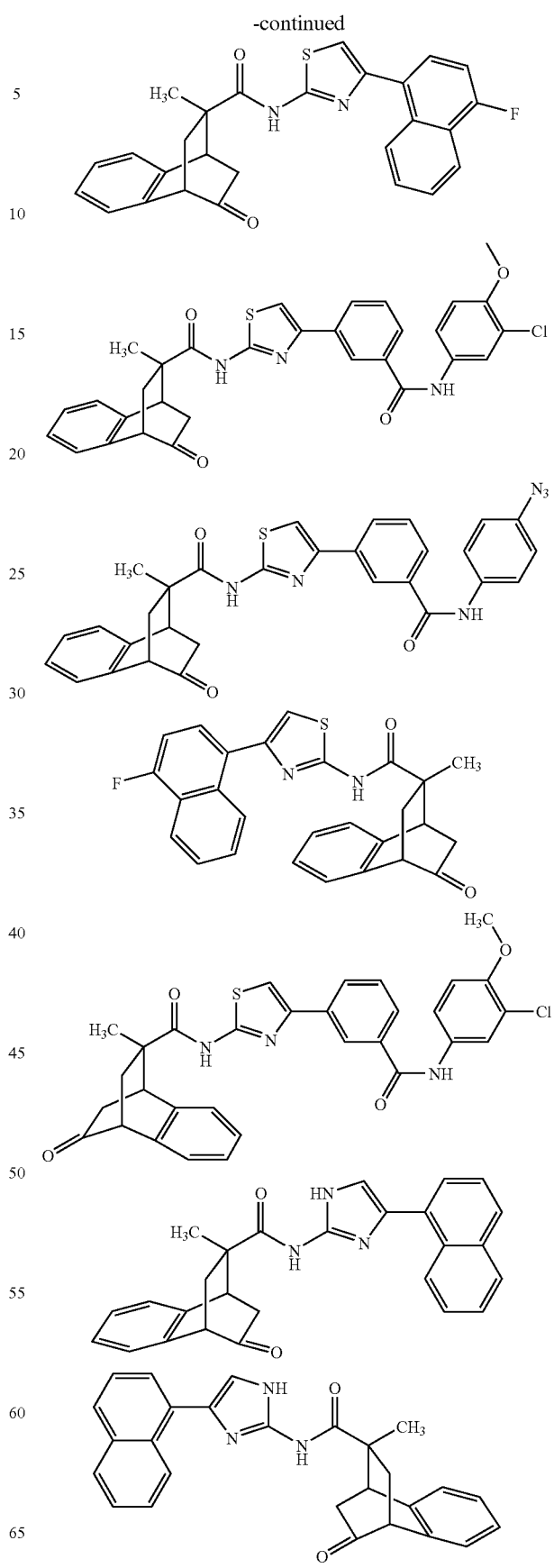

-continued
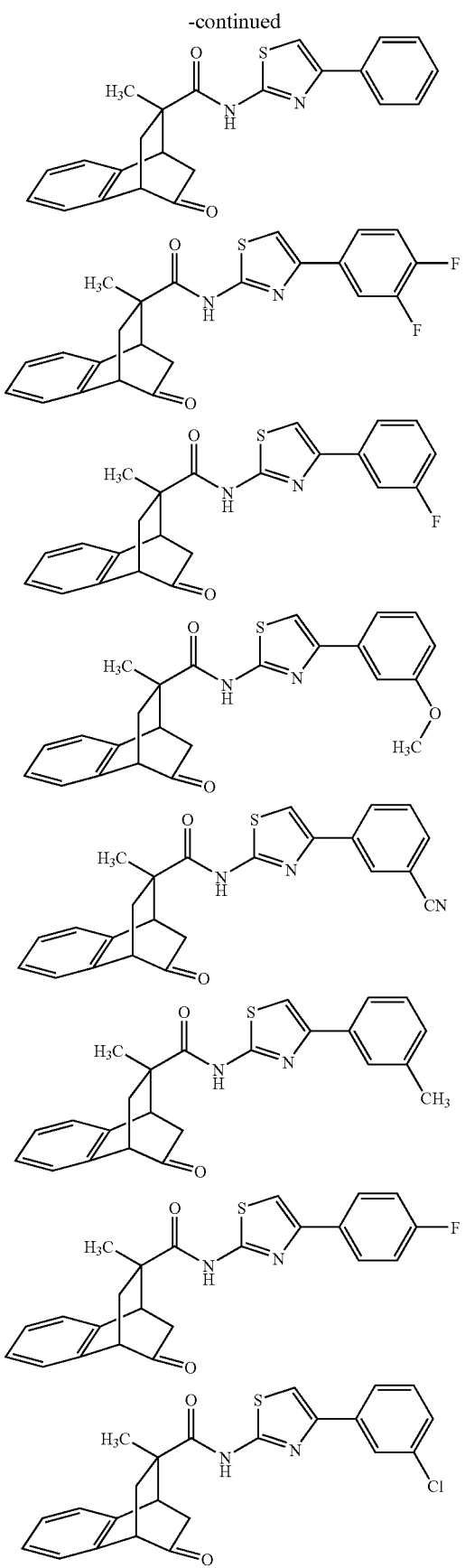
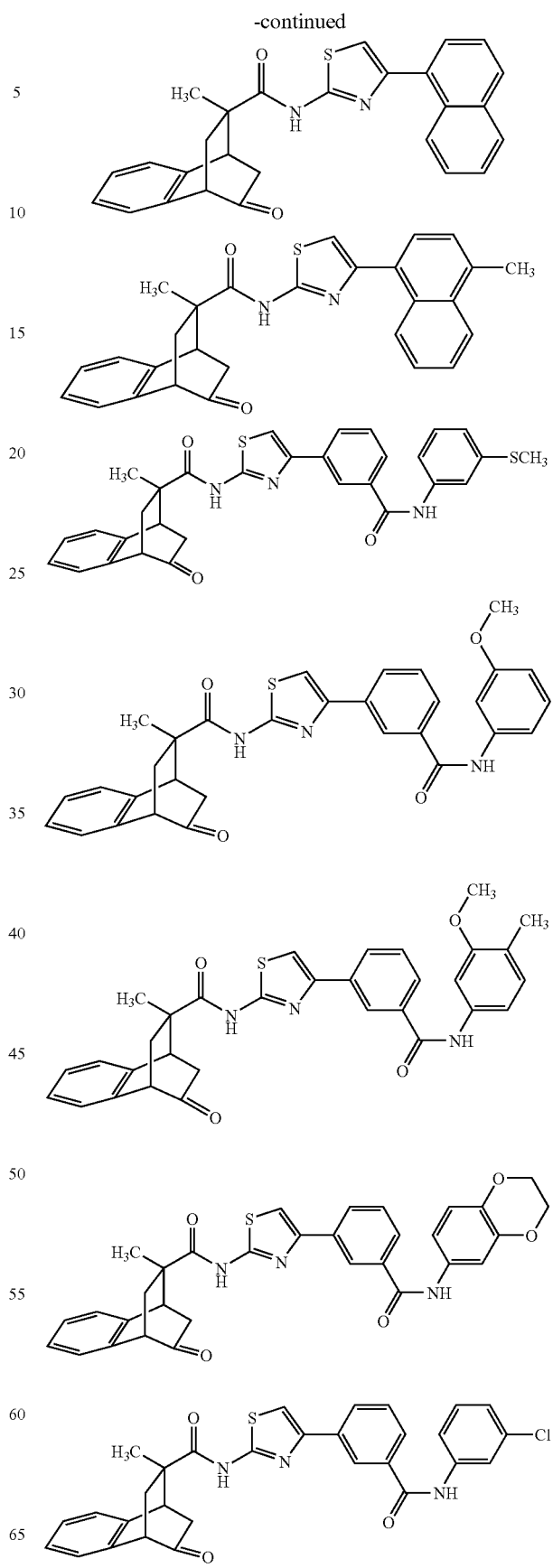

-continued
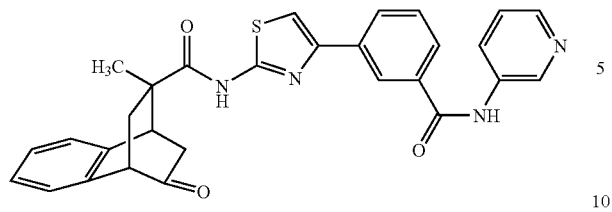
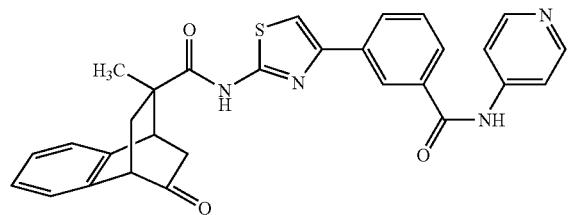
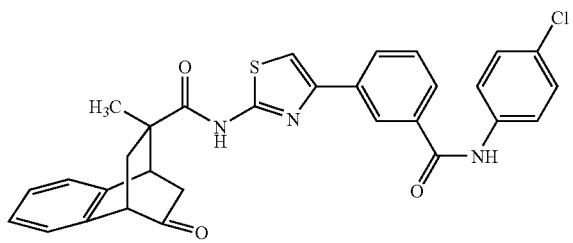
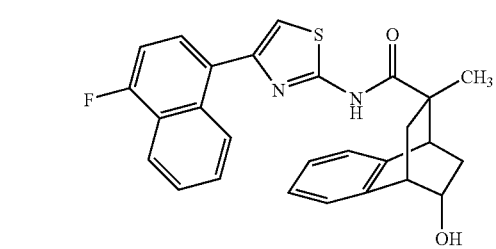
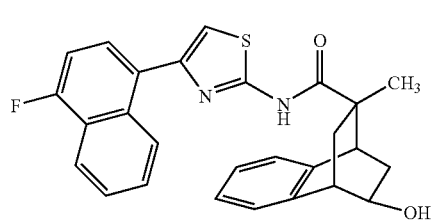
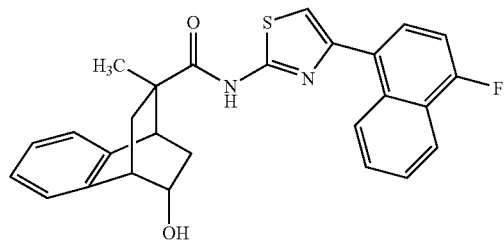
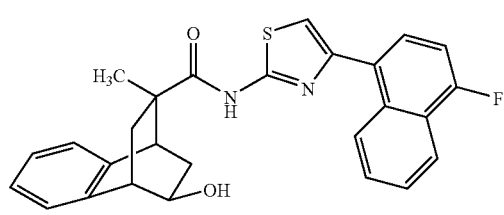
-continued
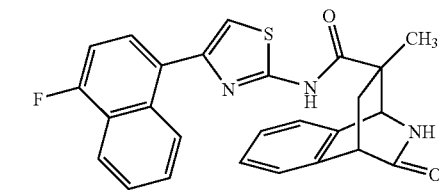
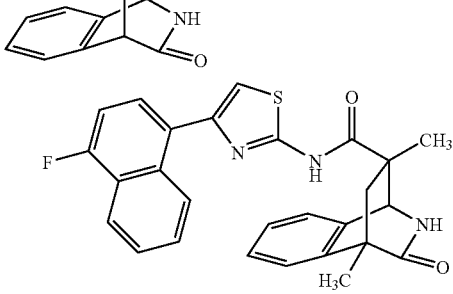
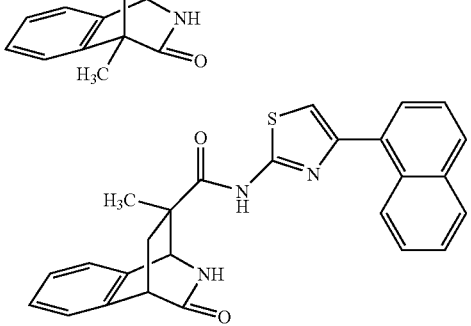
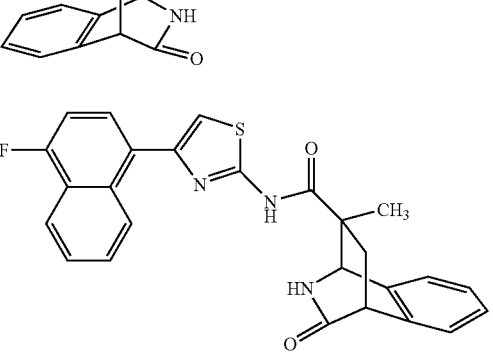

-continued
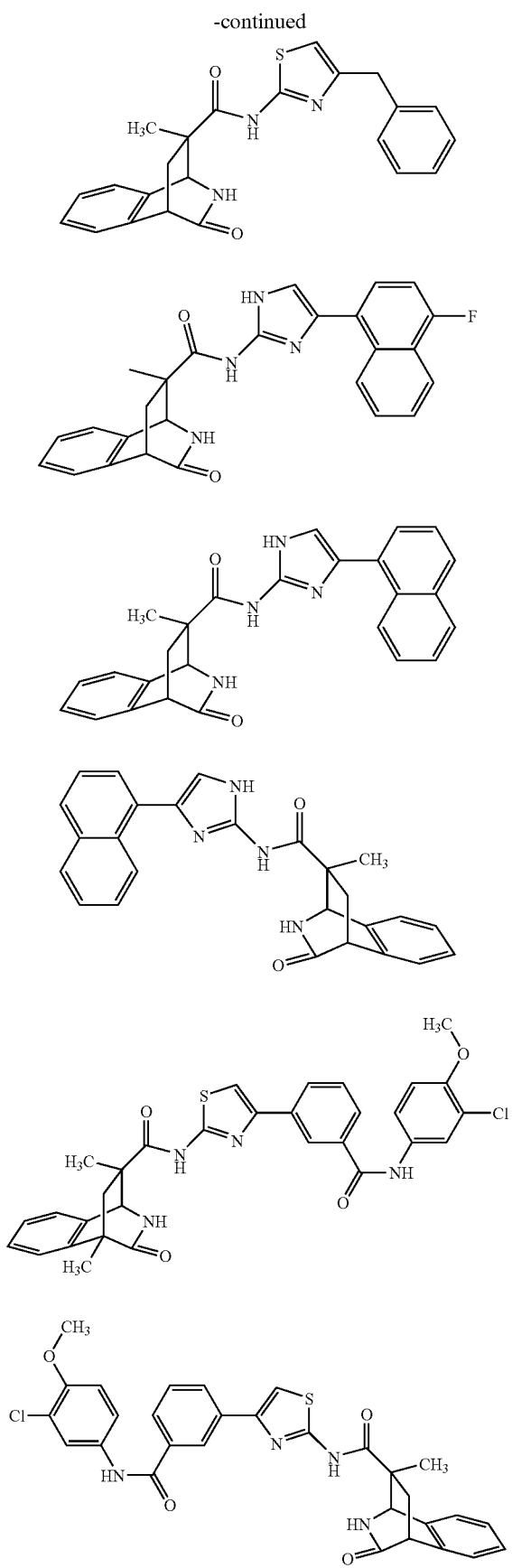
-continued
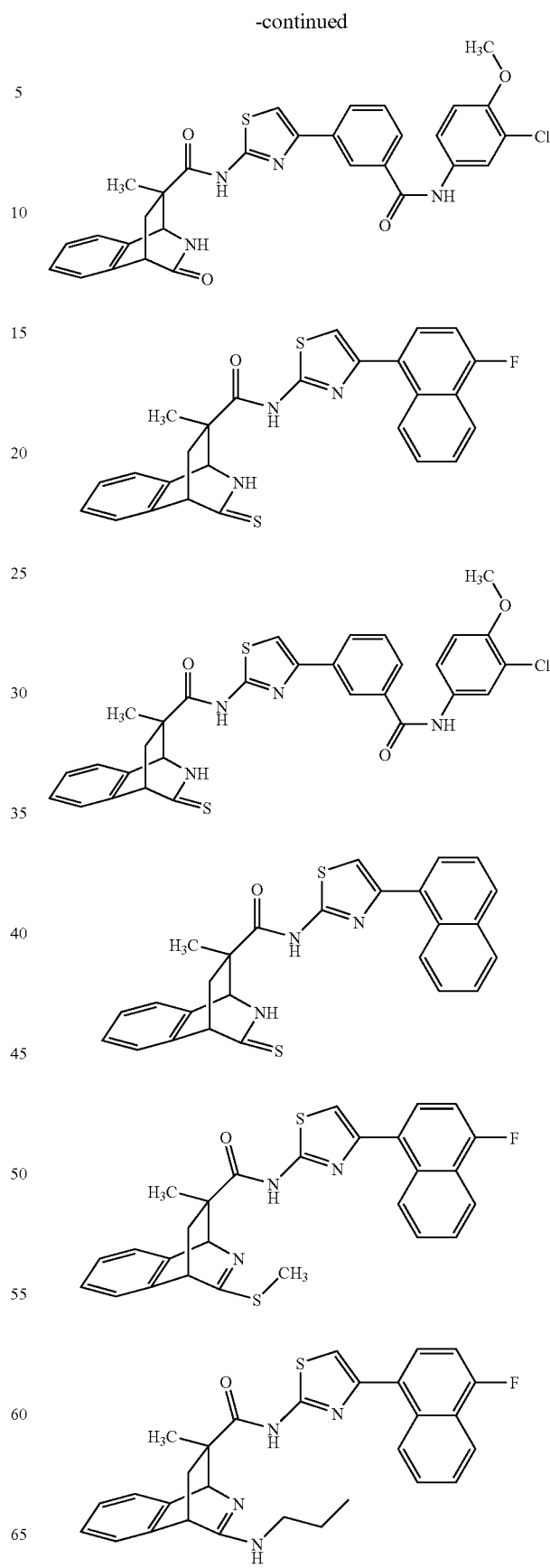

-continued
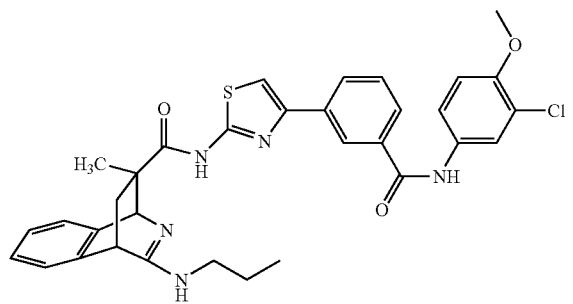
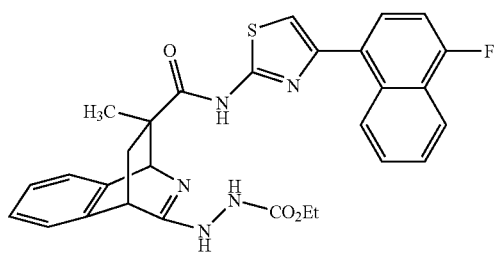
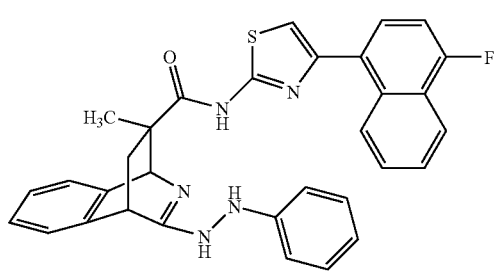
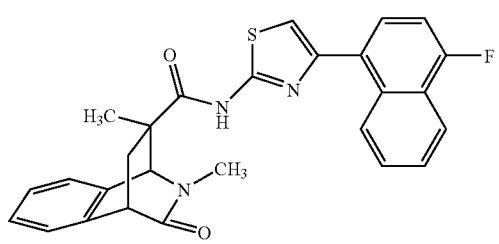
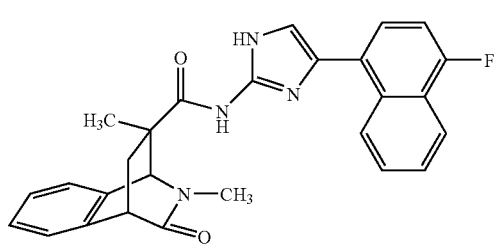
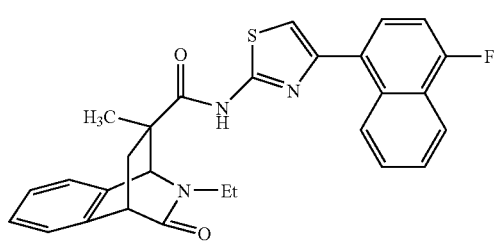
-continued
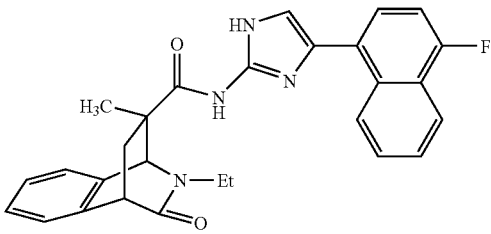
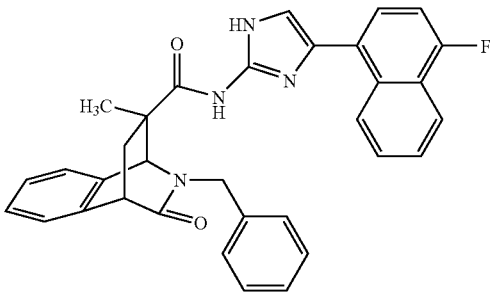
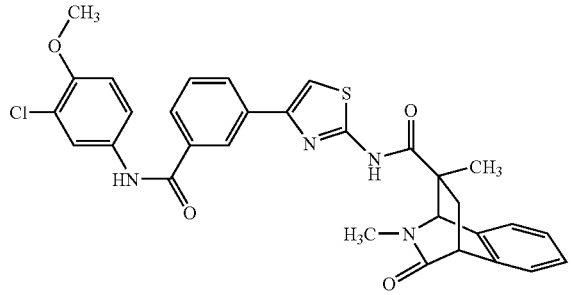
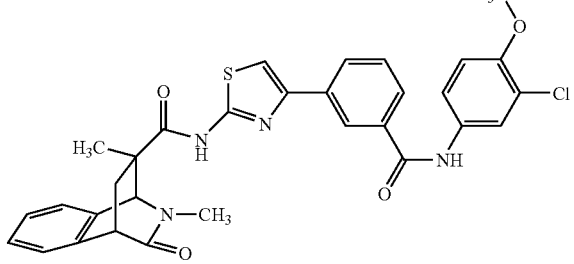
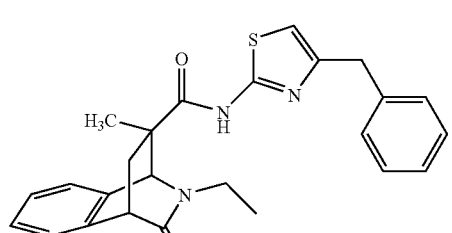
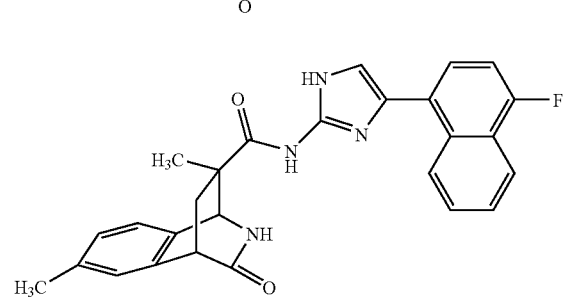

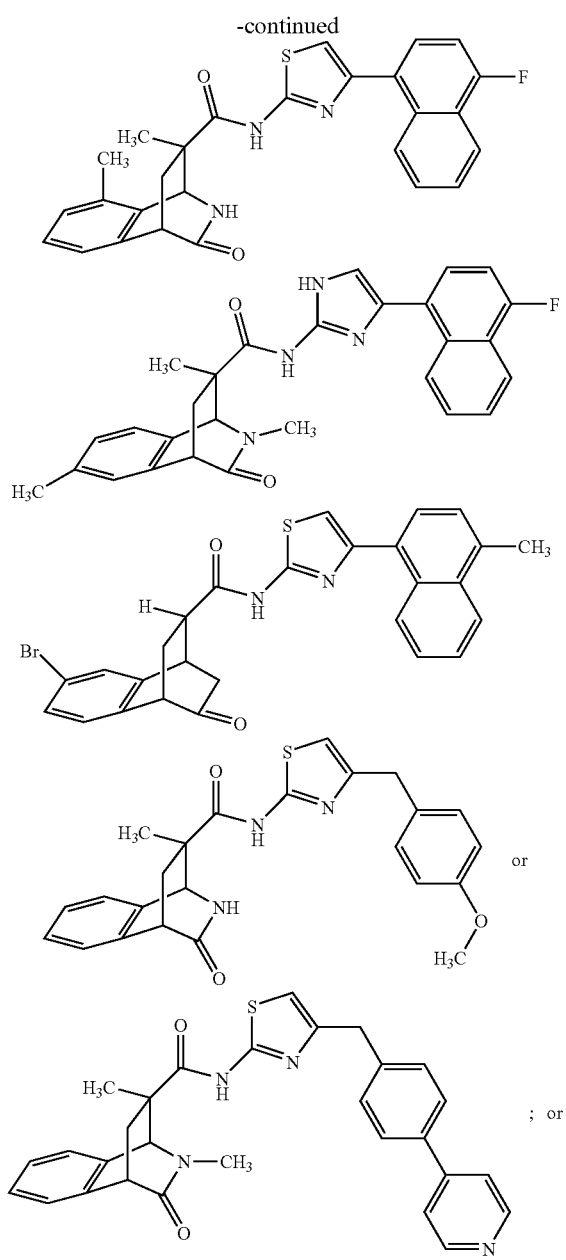

(ii). stereoisomers of (i) thereof, or a pharmaceutically acceptable salt of (i) thereof, or a solvate of (i) thereof.

In another embodiment of the present invention, there is provided pharmaceutical compositions useful in treating endocrine disorders, rheumatic disorders, collagen diseases, dermatologic disease, allergic disease, ophthalmic disease, respiratory disease, hematologic disease, gastrointestinal disease, inflammatory disease, autoimmune disease, diabetes, obesity, and neoplastic disease, as well as other uses as described herein, which includes a therapeutically effective amount (depending upon use) of a compound of formula (I) of the invention and a pharmaceutically acceptable carrier.

In still another embodiment, the present invention provides a method of treating endocrine disorders, rheumatic disorders, collagen diseases, dermatologic disease, allergic disease, ophthalmic disease, respiratory disease, hematologic disease, gastrointestinal disease, inflammatory disease, autoimmune disease, diabetes, obesity, and neoplastic disease, that is a disease associated with the expression product of a gene whose transcription is stimulated or repressed by glucocorticoid receptors, or a disease associated with AP-1- and/or NFκB (particularly AP-1-)-induced transcription, or a disease associated with AP-1 and/or NFκB—(particularly AP-1-) dependent gene expression, wherein the disease is associated with the expression of a gene under the regulatory control of AP-1 and/or NF-κB (particularly AP-1), including inflammatory and immune diseases and disorders as described hereinafter, which includes the step of administering a therapeutically effective amount of a compound of formula (I) of the invention to a patient.

Another embodiment of the present invention involves a method for treating a disease or disorder associated with the expression product of a gene whose transcription is stimulated or repressed by glucocorticoid receptors, or a method of treating a disease or disorder associated with AP-1- and/or NF-κB—(particularly AP-1-) induced transcription, or a method for treating a disease or disorder associated with AP-1 and/or NF-κB (particularly AP-1) dependent gene expression, wherein the disease is associated with the expression of a gene under the regulatory control of AP-1 and/or NF-κβ (particularly AP-1), such as inflammatory and immune disorders, cancer and tumor disorders, such as solid tumors, lymphomas and leukemia, and fungal infections such as mycosis fungoides.

The term "disease associated with GR transactivation," as used herein, refers to a disease associated with the transcription product of a gene whose transcription is transactivated by a GR. Such diseases include, but are not limited to: osteoporosis, diabetes, glaucoma, muscle loss, facial swelling, personality changes, hypertension, obesity, depression, and AIDS, the condition of wound healing, primary or secondary andrenocortical insufficiency, and Addison's disease.

The term "treat", "treating", or "treatment," in all grammatical forms, as used herein refers to the prevention, reduction, or amelioration, partial or complete alleviation, or cure of a disease, disorder, or condition, wherein prevention indicates treatment of a person at risk for developing such a disease, disorder or condition.

The terms "glucocorticoid receptor" and "GR," as used herein, refer either to a member of the nuclear hormone receptor ("NHR") family of transcription factors which bind glucocorticoids and either stimulate or repress transcription, or to GR-beta. These terms, as used herein, refer to glucocorticoid receptor from any source, including but not limited to: human glucocorticoid receptor as disclosed in Weinberger, et al. *Science* 228, p 640-742 (1985), and in Weinberger, et al. *Nature*, 318, p 670-672 (1986); rat glucocorticoid receptor as disclosed in Miesfeld, R. *Nature*, 312, p 779-781 (1985); mouse glucocortoid receptor as disclosed in Danielson, M. et al. *EMBO J.*, 5, 2513; sheep glucocorticoid receptor as disclosed in Yang, K., et al. *J. Mol. Endocrinol.* 8, p 173-180 (1992); marmoset glucocortoid receptor as disclosed in Brandon, D. D., et al, *J. Mol. Endocrinol.* 7, p 89-96 (1991); and human GR-beta as disclosed in Hollenberg, S M. et al. *Nature*, 318, p 635, 1985, Bamberger, C. M. et al. *J. Clin Invest.* 95, p 2435 (1995).

The term, "disease or disorder associated with AP-1 and/or NF-κB" as used herein, refers to a disease associated with the expression product of a gene under the regulatory control of AP-1 and/or NF-κB. Such diseases include, but are not limited to: inflammatory and immune diseases and disorders; cancer and tumor disorders, such as solid tumors, lymphomas and leukemia; and fungal infections such as mycosis fungoides.

The term "inflammatory or immune associated diseases or disorders" is used herein to encompass any condition, disease, or disorder that has an inflammatory or immune component, including, but not limited to, each of the following conditions: transplant rejection (e.g., kidney, liver, heart, lung, pancreas (e.g., islet cells), bone marrow, cornea, small bowel, skin allografts, skin homografts (such as employed in burn treatment), heart valve xenografts, serum sickness, and graft vs. host disease, autoimmune diseases, such as rheumatoid arthritis, psoriatic arthritis, multiple sclerosis, Type I and Type II diabetes, juvenile diabetes, obesity, asthma, inflammatory bowel disease (such as Crohn's disease and ulcerative colitis), pyoderma gangrenum, lupus (systemic lupus erythematosis), myasthenia gravis, psoriasis, dermatitis, dermatomyositis; eczema, seborrhoea, pulmonary inflammation, eye uveitis, hepatitis, Grave's disease, Hashimoto's thyroiditis, autoimmune thyroiditis, Behcet's or Sjorgen's syndrome (dry eyes/mouth), pernicious or immunohaemolytic anaemia, atherosclerosis, Addison's disease (autoimmune disease of the adrenal glands), idiopathic adrenal insufficiency, autoimmune polyglandular disease (also known as autoimmune polyglandular syndrome), glomerulonephritis, scleroderma, morphea, lichen planus, viteligo (depigmentation of the skin), alopecia greata, autoimmune alopecia, autoimmune hypopituatarism, Guillain-Barre syndrome, and alveolitis; T-cell mediated hypersensitivity diseases, including contact hypersensitivity, delayed-type hypersensitivity, contact dermatitis (including that due to poison ivy), uticaria, skin allergies, respiratory allergies (hayfever, allergic rhinitis) and gluten-sensitive enteropathy (Celiac disease); inflammatory diseases such as osteoarthritis, acute pancreatitis, chronic pancreatitis, acute respiratory distress syndrome, Sezary's syndrome and vascular diseases which have an inflammatory and or a proliferatory component such as restenosis, stenosis and artherosclerosis. Inflammatory or immune associated diseases or disorders also includes, but is not limited to: endocrine disorders, rheumatic disorders, collagen diseases, dermatologic disease, allergic disease, ophthalmic disease, respiratory disease, hematologic disease, gastrointestinal disease, inflammatory disease, autoimmune disease, congenital adrenal hyperplasia, nonsuppurative thyroiditis, hypercalcemia associated with cancer, juvenile rheumatoid arthritis, Ankylosing spondylitis, acute and subacute bursitis, acute nonspecific tenosynovitis, acute gouty arthritis, post-traumatic osteoarthritis, synovitis of osteoarthritis, epicondylitis, acute rheumatic carditis, pemphigus, bullous dermatitis herpetiformis, severe erythema multiforme, exfoliative dermatitis, seborrheic dermatitis, seasonal or perennial allergic rhinitis, bronchial asthma, contact dermatitis, atopic dermatitis, drug hypersensitivity reactions, allergic conjunctivitis, keratitis, herpes zoster ophthalmicus, iritis and iridocyclitis, chorioretinitis, optic neuritis, symptomatic sarcoidosis, fulminating or disseminated pulmonary tuberculosis chemotherapy, idiopathic thrombocytopenic purpura in adults, secondary thrombocytopenia in adults, acquired (autoimmune) hemolytic anemia, leukemias and lymphomas in adults, acute leukemia of childhood, regional enteritis, autoimmune vasculitis, multiple sclerosis, chronic obstructive pulmonary disease, solid organ transplant rejection, sepsis. Preferred treatments include treatment of transplant rejection, rheumatoid arthritis, psoriatic arthritis, multiple sclerosis, Type 1 diabetes, asthma, inflammatory bowel disease, systemic lupus erythematosis, psoriasis and chronic pulmonary disease.

In addition, in accordance with the present invention a method of treating a disease associated with AP-1-induced and/or NF-κB-induced transcription (particularly AP-1-induced transcription) is provided wherein a compound of formula (I) of the invention is administered to a patient at risk of developing the disease in a therapeutically effective amount to induce NHR transrepression of the AP-1-induced and/or NF-κB-induced transcription (particularly AP-1-induced transcription), thereby treating the disease.

Other therapeutic agents, such as those described hereafter, may be employed with the compounds of the invention in the present methods. In the methods of the present invention, such other therapeutic agent(s) may be administered prior to, simultaneously with or following the administration of the compound(s) of the present invention.

In a particular embodiment, the compounds of the present invention are useful for the treatment of the aforementioned exemplary disorders irrespective of their etiology, for example, for the treatment of transplant rejection, rheumatoid arthritis, inflammatory bowel disease, and viral infections.

Methods of Preparation

The compounds of the present invention may be synthesized by many methods available to those skilled in the art of organic chemistry. General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds. Example compounds are typically prepared as racemic mixtures. Preparation of homochiral examples may be carried out by techniques known to one skilled in the art. For example, homochiral compounds may be prepared by separation of racemic products by chiral phase preparative high performance liquid chromatography. Alternatively, the example compounds may be prepared by methods known to give enantiomerically enriched products. For example, [4+2]cycloadditions may be carried out with stereocontrolling elements within either reacting component (diene or dienophile). Products are thus obtained as diastereomerically enriched mixtures which give enantiomerically enriched mixtures after a subsequent step in which the stereocontrolling element (typically a chiral auxiliary such as oxazolidinone, menthol ester, pantolactone ester, etc.) is removed.

Compounds of formula I of the invention are prepared as described in the Schemes and examples below. In the schemes the various groups B, J, K, Z, R, $R^a$, $R^b$, $R^c$, $R^d$, $R^q$, $R^w$, m and n correspond to those described above.

Scheme 1. [4 + 2] Cycloadditions

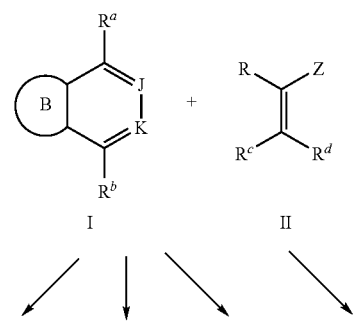

-continued

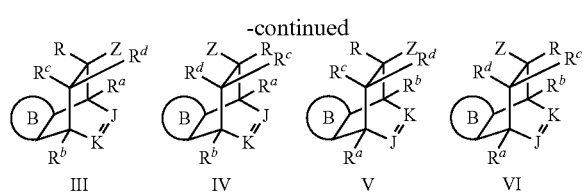

III IV V VI the diene I are carbon atoms and ring B is a substituted or unsubstituted phenyl ring, the diene I is a naphthalene derivative. In this case, when one of J or K is substituted with a hydroxy group, the diene I is β-naphthol, or a substituted derivative thereof. The use of β-naphthol as the diene component of [4+2]cycloadditions has been described in the literature (see Nazaki, et al., *Bull Chem. Soc. Jap.*, 1975; 48(11): 3278-3284 and Barrish, et al., *BioMed. Chem.*, 1993; 1(4): 309-325).

Scheme 2. [4 + 2] Cycloadditions II.

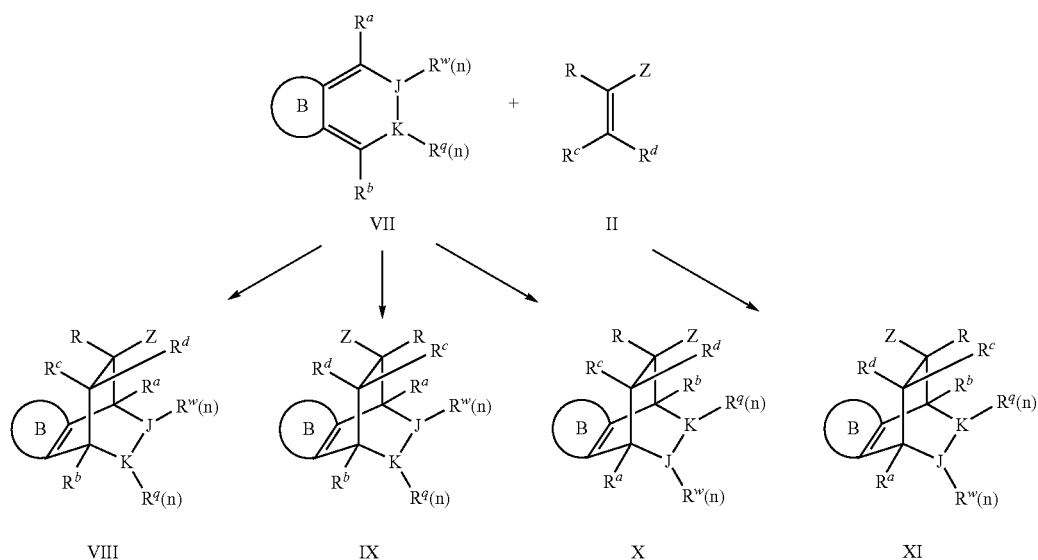

VIII IX X XI

Scheme 1 illustrates a general method for the synthesis of example compounds of the invention, or intermediates which may be readily elaborated to example compounds of the invention. Thus, [4+2]cycloaddition of an appropriately substituted diene (I) with an appropriately substituted dienophile (II) may give rise to one, any combination, or all of the four isomeric products, III-VI. The cycloadditions are typically carried out at elevated temperature (50° C.-200° C.) and may be accelerated under high pressure, such as is generated when the reaction is carried out in a sealed reaction vessel. The cycloadditions may be carried out neat or in an appropriate, inert solvent (such as benzene, toluene, or nitrobenzene). It is well known that that the cycloaddition may be facilitated by the use of a catalyst, such as diethylaluminium chloride or boron trifluoride diethyl etherate. For the diene I, when only one of J or K is nitrogen, the other of J or K is a hydroxy-substituted carbon, and ring B is a substituted or unsubstituted phenyl ring, the diene is a 3-hydroxy isoquinoline which may be obtained commercially or prepared following any general method which has been described for the synthesis of substituted 3-hydroxy isoquinolines (see Fukumi, et al., *Heterocycles*, 1978; 9(9): 1197-1205 and Simchen, et al., *Justus Liebigs Ann. Chem.*, 1974; 1802-1812). The use of 3-hydroxy isoquinolines as the diene component of [4+2]cycloadditions has been described in the literature (see Plieninger, et al., *Chem. Ber.*, 1964; 97:667-681 and Mirak, et al., *Tet. Lett.*, 1970; 1209-1212 and Laszlo, et al., *Hung. Acta Chim. Hungarica*, 1985; 120(4): 271-274). When both atoms J and K of Example compounds of the invention, or intermediates which may be readily elaborated to example compounds of the invention, may also be prepared from [4+2]cycloaddition of dienes represented by the generic structure VII and dienophile II (Scheme 2). When both J and K of diene VII are both carbon, the diene is a substituted cyclohexadiene. The prototypical Diels-Alder [4+2]cycloaddition of cyclohexadienes and dienophiles are well known in the literature. When one of J or K is nitrogen and the other atom is carbon, the diene is a substituted dihydropyridine. The [4+2]cycloadditions of dihyropyridine dienes and dienophiles has been reported in the literature (see Petrzilka, "Preparation and Diels-Alder Reactions of Hetero-Substituted 1,3-Dienes," *Synthesis*, 1981; 753-786 and Sundberg, et al., *J. Org. Chem.*, 1981; 46: 4836.) Dihydropyridines may be prepared readily by the reduction of corresponding pyridines (see Fowler, F., *J. Org. Chem.*, 1972; 37(9): 1321-1323). The reduction is usually carried out in the presence of an acylating reagent (typically a chloroformate such as methyl chloroformate, benzyl chloroformate, or the like) with an appropriate reducing reagent (typically an alkali metal hydride reductant such as sodium borohydride, lithium aluminum hydride, or the like) in an appropriate solvent (typically an alcoholic solvent such as methanol or ethanol).

Scheme 3.

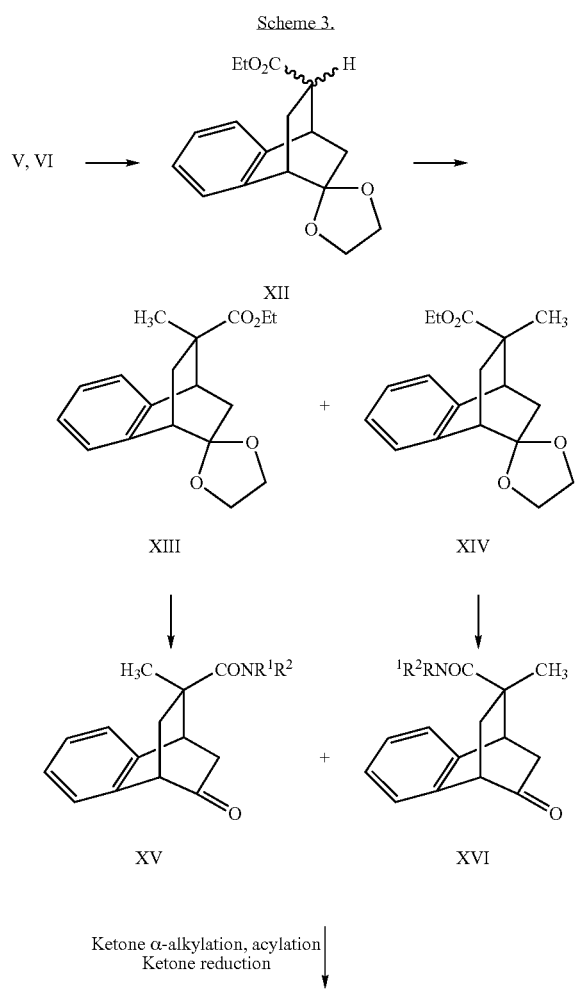

Products V and VI of Scheme 1 (where Z=ethyl, R$^c$ and R$^d$=H, J=COH, K=CH and ring B=phenyl) may be prepared following the method described by Barrish et al. (*BioMed. Chem.*, 1993; 1(4): 309-325). Treatment of a mixture of products V and VI with ethylene glycol under acidic conditions (typically catalytic p-toluene sulfonic acid) in an inert solvent under dehydrative conditions (typically benzene or toluene at reflux in an reaction apparatus equipped with a Dean-Stark trap) provides the mixture of diastereomeric dioxolane ketals XII (Scheme 3). Alpha-methylation of the ethyl ester may then be accomplished by generation of ester enolate with a suitable base (lithium diisopropyl amide, hexamethyl disilazane or the like) at low temperature (typically −78° C. to −30° C.) in a suitable solvent for enolate generation (typically anhydrous tetrahydrofuran, "THF"), followed by quenching of the intermediate enolate with the addition of iodomethane to provide the intermediate alpha-methylated esters XIII and XIV. The esters XIII and XIV may then be elaborated to keto-amides XV and XVI, respectively. Thus, saponification of the ethyl ester functionality of XIII or XIV may be carried out under basic conditions (typically 1N lithium hydroxide ("LiOH") in a mixture of THF, water, and methanol) at elevated temperature (typically 80° C.) to provide a carboxylic acid intermediate. Condensation of the acid with an amine NHR$^1$R$^2$ may then be effected under standard amide-forming reaction conditions (typically 1-hydroxybenzotriazole hydrate ("HOBt") or 1-hydroxy-7-azabenzotriazole ("HOAt") in the presence of a carbodiimide such as the water-soluble 1-[3-(dimethylamino)propyl-3-ethylcarbodiimide hydrochloride ("EDCI") and tertiary amine base such as triethylamine, or diisopropylethylamine in an appropriate solvent, such as dimethylformamide ("DMF") or acetonitrile, at elevated temperature (typically 70-90° C. Removal of the dioxolane ketal may be effected under acidic conditions with an aqueous mineral acid (typically a solution of 1-2N hydrochloric acid ("HCl") in THF) at ambient temperature. Preparation of ketoamides XV and XVI from esters XIII and XIV may also be carried out by initial removal of the ketal functionality, followed by ester saponification and subsequent amide formation, employing the conditions described above for each step. The ketones XV and XVI may be subsequently derivatized to other compounds of the invention. For example, treatment of the ketone with 1-2 equivalents of a suitable base for enolate generation (e.g., lithium diisopropylamide ("LDA") or lithium hexamethyldisilazane) followed by quenching with an appropriate electrophile (typically an alkyl halide such as benzyl bromide, iodomethane, and the like) will provide an alpha-alkylated ketone. Alternatively, the enolate may be treated with an appropriate acylating reagent (acyl halide, chloroformate, cyanoformate, or the like) to provide an alpha-acylated ketone product. The ketones XV and XVI may be reduced to the corresponding secondary alcohols by treatment with an appropriate reducing agent under standard ketone reduction conditions (typically sodium borohydride in methanol).

Scheme 4.

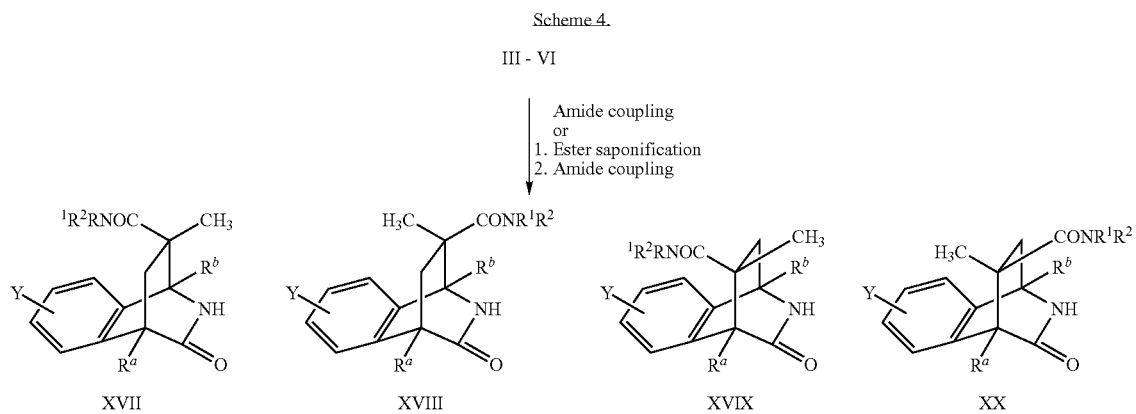

Each of the products III-VI of Scheme 1 (where R=CH₃, Z=CO₂H, R^c and R^d=H, J=COH, and K=N) may be coupled to primary or secondary amines to give example compounds of the invention corresponding to XVII-XX (Scheme 4). Thus, condensation of the carboxylic acid starting material with an amine NHR¹R² may then be effected under standard amide-forming reaction conditions (typically HOBt or HOAt in the presence of a carbodiimide such as the water-soluble carbodiimide EDCI and tertiary amine base such as triethylamine, or diisopropylethylamine in an appropriate solvent such as DMF or acetonitrile) at elevated temperature (typically 70-90° C.). Alternatively, when the products III-VI of Scheme 1 are esters (where R=CH₃, Z=CO₂R^e, R^e=Me or Et, R^c and R^d=H, J=COH, and K=N) the ester may first be saponified with an aqueous base (typically 1N LiOH in a mixture of THF, water, and methanol or 4N potassium hydroxide ("KOH") in methanol) at elevated temperature (typically 80° C.) to provide carboxylic acid intermediates which may then be coupled with an amine as described above to provide amides XVII-XX.

water-soluble carbodiimide EDCI and tertiary amine base such as triethylamine, or diisopropylethylamine in an appropriate solvent such as DMF or acetonitrile) at elevated temperature (typically 70-90° C.) to provide N-alkyl lactam amides XXV-XXVIII.

Definition of Terms

Unless otherwise indicated, the term "lower alkyl", "alkyl" or "alk" as employed herein alone or as part of another group includes both straight and branched chain hydrocarbons, containing 1 to 20 carbons, preferably 1 to 10 carbons, more preferably 1 to 8 carbons, in the normal chain, and may optionally include an oxygen or nitrogen in the normal chain. Examples of such chains include methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like, as well as such groups including 1 to 4 substituents such as halo, (including F, Br, Cl or I), CF₃, alkoxy, aryl, aryloxy, aryl(aryl) or diaryl, arylalkyl, arylalky-

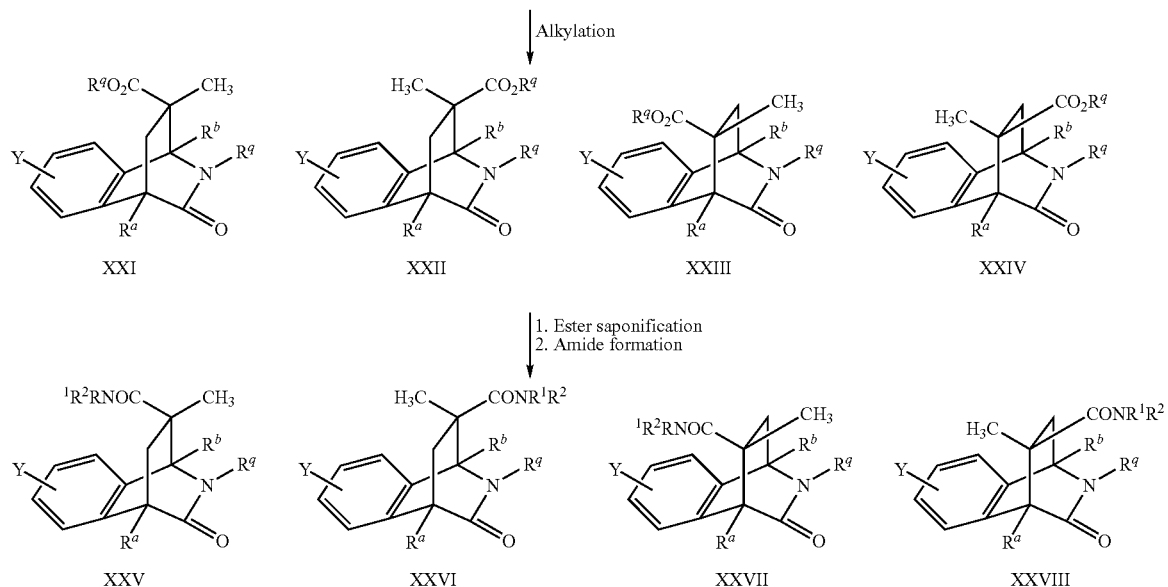

Scheme 5.

III - VI

XXI XXII XXIII XXIV

XXV XXVI XXVII XXVIII

Each of the products III-VI of Scheme 1 (where R=CH₃, Z=CO₂H, R^c and R^d=H, J=COH, and K=N) may be doubly alkylated to provide the N-alkyl lactam esters XXI-XXIV, where R^q is an alkyl group (Scheme 5). The alkylation may be effected by treatment of the lactam carboxylic acid with a suitable base and electrophile in an appropriate solvent (typically cesium carbonate and alkyl halide such as benzyl bromide, methyl iodide, etc., in warm acetone). Subsequent saponification of the ester functionality may be carried out under basic conditions (typically 1N LiOH in a mixture of THF, water, and methanol or 4N KOH in methanol) at elevated temperature (typically 80° C.) to provide a carboxylic acid intermediate. Condensation of the carboxylic acid intermediate with an amine NHR¹R² may then be effected under standard amide-forming reaction conditions (typically HOBt or HOAt in the presence of a carbodiimide such as the loxy, alkenyl, cycloalkyl, cycloalkylalkyl, cycloalkylalkyloxy, amino, hydroxy, hydroxyalkyl, acyl, heteroaryl, heteroaryloxy, HO—N=, cycloheteroalkyl, alkyloxycarbonyl, alkoxyoximyl, arylheteroaryl, arylalkoxycarbonyl, heteroarylalkyl, heteroarylalkoxy, aryloxyalkyl, aryloxyaryl, alkylamido, alkanoylamino, hydroxyalkyl (alkyl)amino carbonyl, arylcarbonylamino, nitro, cyano, thiol, haloalkyl, trihaloalkyl and/or alkylthio and/or any of the substituents for aryl.

When numbers appear in a subscript after the symbol "C", the subscript defines with more specificity the number of carbon atoms that a particular group may contain. The subscript "0" refers to a bond. When the term "alkyl" is used together with another group, such as in "arylalkyl", this conjunction defines with more specificity at least one of the substituents that the alkyl will contain. For example, "arylalkyl" or "(aryl)alkyl" refers to an alkyl group as defined above where at least one of the substituents is an aryl, such as benzyl. Also, the term aryl($C_{0-4}$)alkyl includes a lower alkyl having at least one aryl substituent and also includes an aryl directly bonded to another group, i.e., aryl($C_0$)alkyl.

Unless otherwise indicated, the term "cycloalkyl" as employed herein alone or as part of another group includes saturated cyclic hydrocarbon groups containing 1 to 3 rings, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings (defined below). Accordingly, the term "cycloalkyl" includes groups such as cyclopropyl, cyclobutyl, cyclopentyl, cyclohexyl, cycloheptyl, cyclooctyl, cyclodecyl and cyclododecyl, cyclohexenyl,

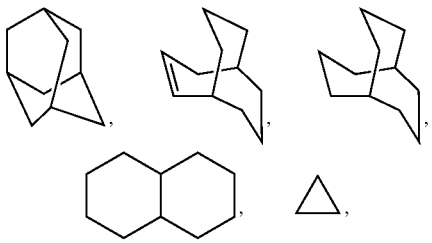

and the like as well as such groups including 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol and/or alkylthio and/or any of the substituents for alkyl.

The term "cycloalkenyl" as employed herein alone or as part of another group refers to cyclic hydrocarbons containing 3 to 12 carbons, preferably 5 to 10 carbons and 1 or 2 double bonds. Exemplary cycloalkenyl groups include cyclopentenyl, cyclohexenyl, cycloheptenyl, cyclooctenyl, cyclohexadienyl, and cycloheptadienyl, which may be optionally substituted as defined for cycloalkyl.

The term "cycloalkylene" as employed herein refers to a "cycloalkyl" group which includes free bonds and thus is a linking group such as

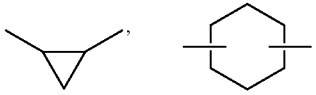

and the like, and may optionally be substituted as defined above for "cycloalkyl".

The term "alkanoyl" as used herein alone or as part of another group refers to alkyl linked to a carbonyl group.

Unless otherwise indicated, the term "lower alkenyl" or "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, and may optionally include an oxygen or nitrogen in the normal chain. Accordingly, the term "lower alkenyl" or "alkenyl" includes groups such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like as well as such groups including 1 to 4 substituents such as halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonylamino, nitro, cyano, thiol, alkylthio and/or any of the substituents for alkyl set out herein.

Unless otherwise indicated, the term "lower alkynyl" or "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, and may optionally include an oxygen or nitrogen in the normal chain. Accordingly, the term "lower alkynyl" or "alkynyl" includes groups such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like as well as such groups including 1 to 4 substituents such as halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the substituents for alkyl set out herein.

The terms "arylalkenyl" and "arylalkynyl" as used alone or as part of another group refer to alkenyl and alkynyl groups as described above having an aryl substituent.

The term "alkylene" refers to bivalent straight or branched chain hydrocarbon groups having 1 to 12 carbon atoms, preferably 1 to 8 carbon atoms, e.g. $\{-CH_2-\}_n$, wherein n is 1 to 12, preferably 1-8. Lower alkylene groups, that is, alkylene groups of 1 to 4 carbon atoms, are most preferred, for example "methylene". The terms "alkenylene" and "alkynylene" refer to bivalent radicals of alkenyl and alkynyl groups, respectively, as defined above. When reference is made to a substituted alkenyl, alkynyl, alkylene, alkenylene, or alkynylene group, these groups are substituted with one to three substitutents as defined above for substituted alkyl groups.

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

$(CH_2)_p$ and $(CH_2)_q$, includes alkylene, allenyl, alkenylene or alkynylene groups, as defined herein, each of which may optionally include an oxygen or nitrogen in the normal chain, which may optionally include 1, 2, or 3 substituents which include alkyl, alkenyl, halogen, cyano, hydroxy, alkoxy, amino, thioalkyl, keto, $C_3$-$C_6$ cycloalkyl, alkylcarbonylamino or alkylcarbonyloxy; the alkyl substituent may be an alkylene moiety of 1 to 4 carbons which may be attached to one or two carbons in the $(CH_2)_p$ or $(CH_2)_q$ group to form a cycloalkyl group therewith.

Examples of $(CH_2)_p$, $(CH_2)_q$, alkylene, alkenylene and alkynylene include

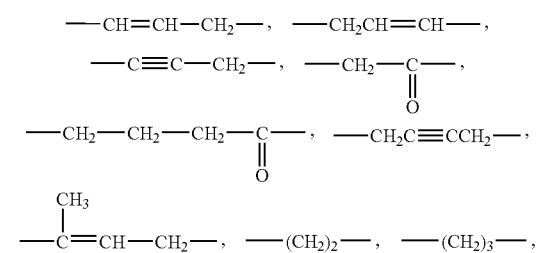

-continued

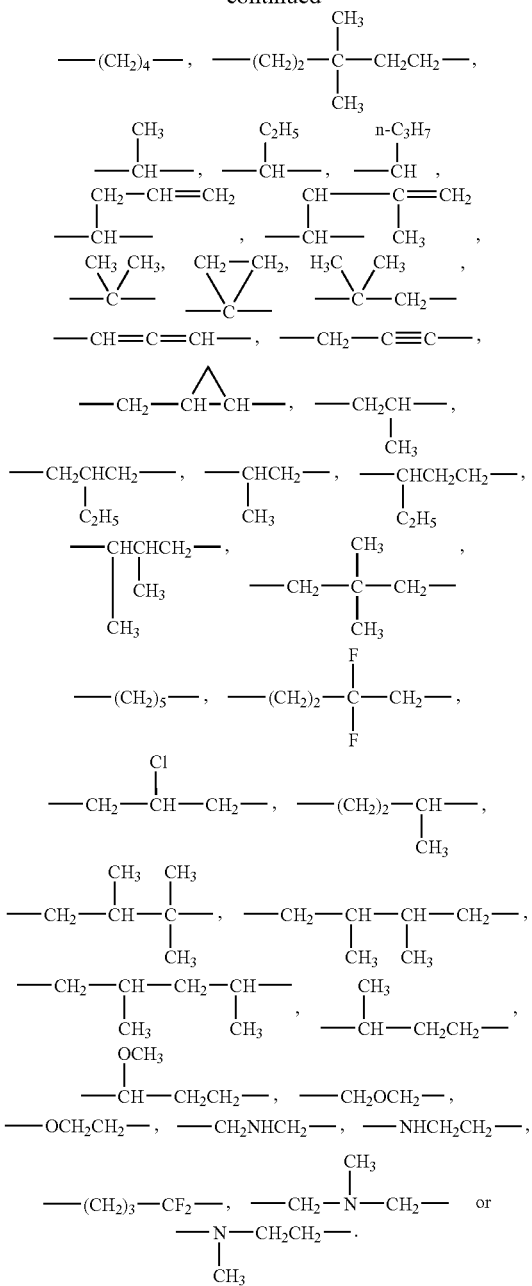

The term "halogen" or "halo" as used herein alone or as part of another group (e.g. CF$_3$ is a haloalkyl group) refers to chlorine, bromine, fluorine, and iodine, with chlorine fluorine or bromine being preferred.

The term "metal ion" refers to alkali metal ions such as sodium, potassium or lithium and alkaline earth metal ions such as magnesium and calcium, as well as zinc and aluminum.

Unless otherwise indicated, the term "aryl", as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring (such as aryl, cycloalkyl, heteroaryl or cycloheteroalkyl rings. Accordingly, the term "aryl" includes, for example

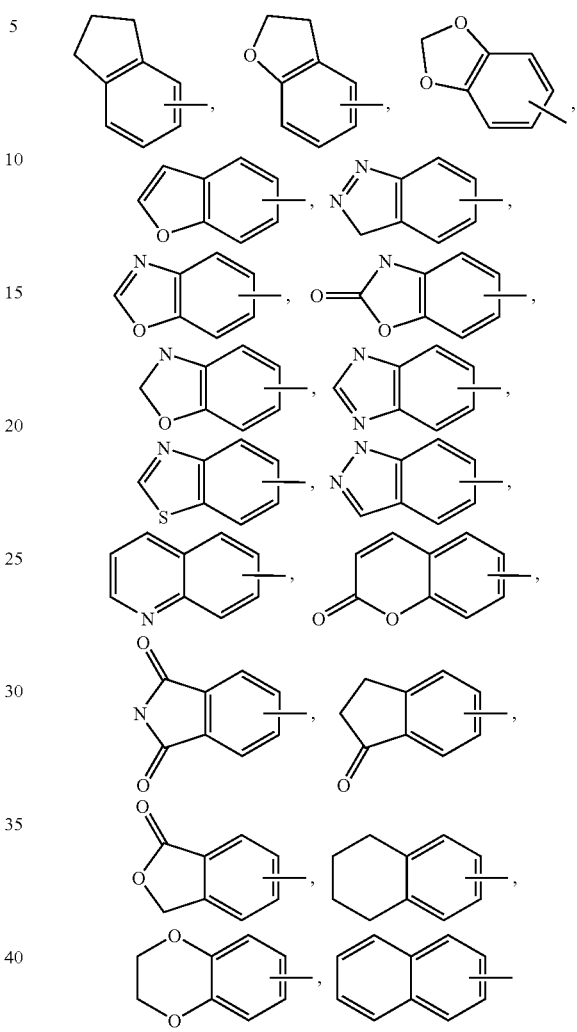

and may be optionally substituted through available carbon atoms with 1, 2, or 3 groups selected from hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, alkoxycarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl, carboxy, cycloalkyl, arylalkoxy, aryloxycarbonyl, cycloalkylaminocarbonyl, cycloalkylalkylaminocarbonyl, alkoxycarbonylalkyl, alkoxyalkylaminocarbonyl, heteroarylaminocarbonyl, heteroarylalkylaminocarbonyl, arylalkylaminocarbonyl, N-hydroxyalkyl(N-alkyl)aminocarbonyl, cycloheteroalkylaminocarbonyl, cycloheteroalkylalkylaminocarbonyl, N-aryl(N-alkyl)aminocarbonyl, N-arylalkyl(N-cyanoalkyl) aminocarbonyl, dialkylaminoalkylaminocarbonyl, dialkylaminocarbonyl, alkyl-, arylalkyl- or aryl-cycloheteroalkylaminocarbonyl, N-dialkylaminoalkyl(N-alkyl or N-arylalkyl)aminocarbonyl, N-heteroarylalkyl(N-alkyl)aminocarbonyl, N-arylalkyl(N-alkyl)aminocarbonyl, N-dialkylamino(N-arylalkyl)aminocarbonyl, N-hydroxyalkyl(N-arylalkyl)aminocarbonyl, aminoalkyloxycarbonyl, cycloheteroalkylcarbonyl, N=N=N, alkylsulfonyl, aminosulfonyl, heteroarylaminosulfonyl, and/or any of the substituents for alkyl set out herein.

Unless otherwise indicated, the term "lower alkoxy", "alkoxy", "aryloxy" or "aralkoxy" as employed herein alone or as part of another group includes any of the above alkyl, aralkyl or aryl groups linked to an oxygen atom.

Unless otherwise indicated, the term "substituted amino" as employed herein alone or as part of another group refers to amino substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl or thioalkyl. These substituents may optionally be further substituted with a carboxylic acid and/or any of the substituents for alkyl as set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, alkoxy, alkylthio, halo, trifluoromethyl or hydroxy.

Unless otherwise indicated, the term "lower alkylthio", alkylthio", "arylthio" or "aralkylthio" as employed herein alone or as part of another group includes any of the above alkyl, aralkyl or aryl groups linked to a sulfur atom.

Unless otherwise indicated, the term "acyl" as employed herein by itself or part of another group, as defined herein, refers to an organic radical linked to a carbonyl

group; examples of acyl groups include any of the R groups attached to a carbonyl, such as alkanoyl, alkenoyl, aroyl, aralkanoyl, heteroaroyl, cycloalkanoyl, cycloheteroalkanoyl and the like.

Unless otherwise indicated, the term "lower alkylamino", "alkylamino", "acylamino", "arylamino", or "arylalkylamino" as employed herein alone or as part of another group includes any of the above alkyl, aryl or arylalkyl acyl groups linked to a nitrogen atom. The term "acylamino", for example, includes the group
—NHC(O)alkyl.

Unless otherwise indicated, the term "cycloheteroalkyl" as used herein alone or as part of another group refers to a 5-, 6- or 7-membered saturated or partially unsaturated ring which includes 1 to 2 hetero atoms such as nitrogen, oxygen and/or sulfur, linked through a carbon atom or a heteroatom, where possible, optionally via the linker $(CH_2)_p$ (where p is 0, 1, 2 or 3), such as

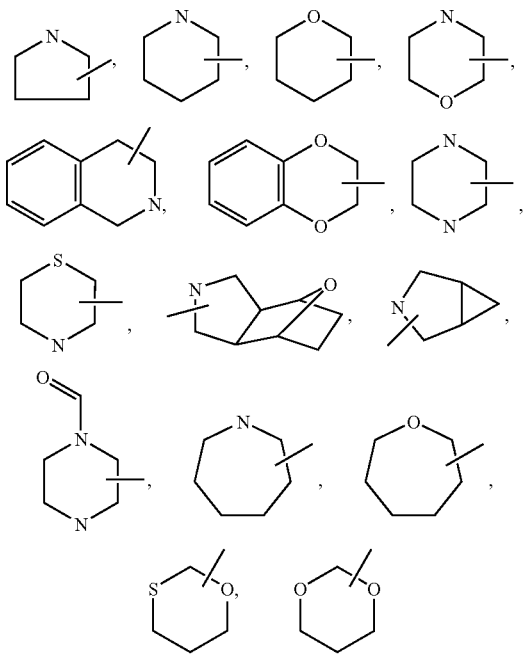

and the like. The above groups may include 1 to 4 substituents such as alkyl, halo, oxo and/or any of the substituents for alkyl or aryl set out herein. In addition, any of the cycloheteroalkyl rings can be fused to a cycloalkyl, aryl, heteroaryl or cycloheteroalkyl ring.

Unless otherwise indicated, the term "heteroaryl" as used herein alone or as part of another group refers to a 5-, 6- or 7-membered aromatic ring which includes 1, 2, 3 or 4 hetero atoms such as nitrogen, oxygen or sulfur, and such rings fused to an aryl, cycloalkyl, heteroaryl or cycloheteroalkyl ring (e.g. benzothiophenyl, indolyl), and includes possible N-oxides, linked through a carbon atom or a heteroatom, where possible, optionally via the linker $(CH_2)_q$ (where q is 0, 1, 2 or 3). The heteroaryl group may optionally include 1 to 4 substituents such as any of the substituents for alkyl or aryl set out above. Examples of heteroaryl groups include the following:

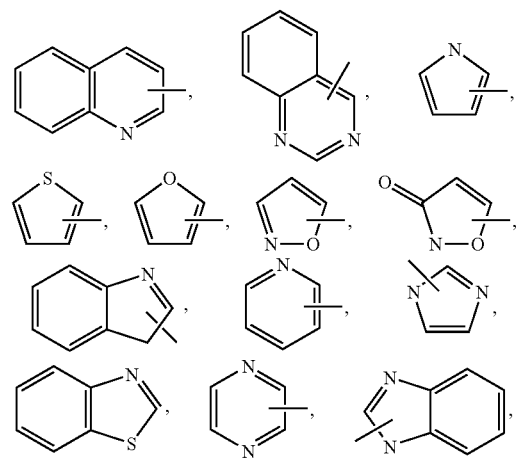

-continued

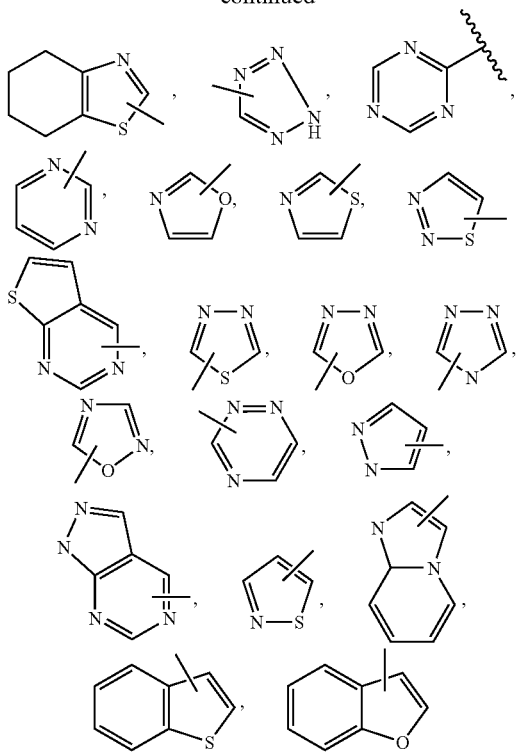

and the like.

The term "cycloheteroalkylalkyl" as used herein alone or as part of another group refers to cycloheteroalkyl groups as defined above linked through a C atom or heteroatom to a $(CH_2)_p$ chain.

The term "heteroarylalkyl" or "heteroarylalkenyl" as used herein alone or as part of another group refers to a heteroaryl group as defined above linked through a C atom or heteroatom to a —$(CH_2)_q$— chain, alkylene or alkenylene as defined above.

The term "polyhaloalkyl" as used herein refers to an "alkyl" group as defined above which includes from 2 to 9, preferably from 2 to 5, halo substituents, such as F or Cl, preferably F, such as $CF_3CH_2$, $CF_3$ or $CF_3CF_2CH_2$.

The term "polyhaloalkyloxy" as used herein refers to an "alkoxy" or "alkyloxy" group as defined above which includes from 2 to 9, preferably from 2 to 5, halo substituents, such as F or Cl, preferably F, such as $CF_3CH_2O$, $CF_3O$ or $CF_3CF_2CH_2O$.

The term 'homochiral' refers to a compound of high enantiomeric purity (greater than 95% enantiomeric excess). The term 'homochiral' does not define or imply the absolute stereochemical assignment of the compound to which it refers.

The term "prodrug" denotes a compound which, upon administration to a subject, undergoes chemical conversion by metabolic or chemical processes to yield a compound of the formula (I), and/or a salt and/or solvate thereof. For example, compounds containing a carboxy group can form physiologically hydrolyzable esters which serve as prodrugs by being hydrolyzed in the body to yield formula (I) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula (I) include $C_{1-6}$alkylbenzyl, 4-methoxybenzyl, indanyl, phthalyl, methoxymethyl, $C_{1-6}$alkanoyloxy-$C_{1-6}$alkyl, e.g. acetoxymethyl, pivaloyloxymethyl or propionyloxymethyl, $C_{1-6}$alkoxycarbonyloxy-$C_{1-6}$alkyl, e.g. methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Prodrug ester examples include the following groups: (1-alkanoyloxy)alkyl such as,

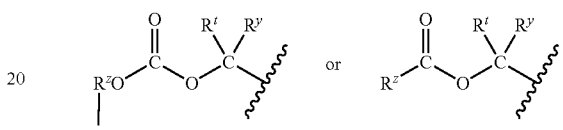

wherein $R^z$, $R^t$ and $R^y$ are H, alkyl, aryl or arylalkyl; however, $R^zO$ cannot be HO.

Further, examples of prodrug esters include

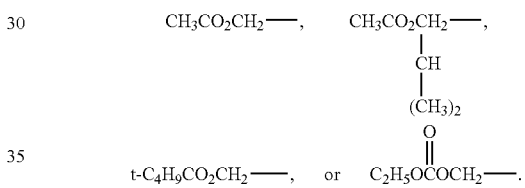

Other examples of suitable prodrug esters include

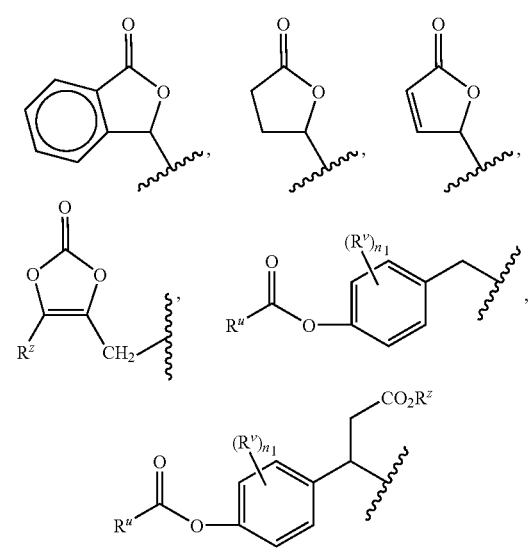

wherein $R^z$ can be H, alkyl (such as methyl or t-butyl), arylalkyl (such as benzyl) or aryl (such as phenyl); $R^v$ is H, alkyl, halogen or alkoxy, $R^u$ is alkyl, aryl, arylalkyl or alkoxyl, and n1 is 0, 1 or 2.

For further examples of prodrug derivatives (including prodrug esters), see:

a) *Design of Prodrugs*, edited by H. Bundgaard, (Elsevier, 1985) and *Methods in Enzymology*, Vol. 42, p. 309-396, edited by K. Widder, et al. (Acamedic Press, 1985);

b) A Textbook of Drug Design and Development, edited by Krosgaard-Larsen and H. Bundgaard, Chapter 5, "Design and Application of Prodrugs," by H. Bundgaard, pp. 113-191 (1991); and c) H. Bundgaard, *Advanced Drug Delivery Reviews*, 8, 1-38 (1992).

The term "tautomer" refers to compounds of the formula (I) and salts thereof that may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention.

The terms pharmaceutically acceptable "salt" and "salts" refer to basic salts formed with inorganic and organic bases. Such salts include ammonium salts; alkali metal salts, such as lithium, sodium and potassium salts (which are preferred); alkaline earth metal salts, such as calcium and magnesium salts; salts with organic bases, such as amine like salts (e.g., dicyclohexylamine salt, benzathine, N-methyl-D-glucamine, and hydrabamine salts); and salts with amino acids like arginine, lysine and the like; and zwitterions, the so-called "inner salts". Nontoxic, pharmaceutically acceptable salts are preferred, although other salts are also useful, e.g., in isolating or purifying the product.

The term pharmaceutically acceptable "salt" and "salts" also includes acid addition salts. These are formed, for example, with strong inorganic acids, such as mineral acids, for example sulfuric acid, phosphoric acid or a hydrohalic acid such as HCl or HBr, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as (C1-C4) alkyl or arylsulfonic acids which are unsubstituted or substituted, for example by halogen, for example methanesulfonic acid or p-toluenesulfonic acid.

All stereoisomers of the compounds of the instant invention are contemplated, either in admixture or in pure or substantially pure form. The compounds of the present invention can have asymmetric centers at any of the carbon atoms including any one or the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic or fractional crystallization.

The inventive compounds may be in the free or solvate (e.g. hydrate) form.

Combinations

Where desired, the compounds of structure I may be used in combination with one or more other types of therapeutic agents such as immunosuppressants, anticancer agents, antiviral agents, anti-inflammatory agents, anti-fungal agents, antibiotics, anti-vascular hyperproliferation agents, anti-depressive agents, hypolipidemic agents or lipid-lowering agents or lipid modulating agents, antidiabetic agents, anti-obesity agents, antihypertensive agents, platelet aggregation inhibitors, and/or anti-osteoporosis agents, which may be administered orally in the same dosage form, in a separate oral dosage form or by injection.

The immunosuppressants which may be optionally employed in combination with compounds of formula I of the invention include cyclosporins, for example cyclosporin A, mycophenolate, interferon-beta, deoxyspergolin, FK-506 or Ant.-IL-2.

The anti-cancer agents which may be optionally employed in combination with compounds of formula I of the invention include azathiprine, 5-fluorouracil, cyclophosphamide, cisplatin, methotrexate, thiotepa, carboplatin, and the like.

The anti-viral agents which may be optionally employed in combination with compounds of formula I of the invention include abacavir, aciclovir, ganciclovir, zidanocin, vidarabine, and the like.

The anti-inflammatory agents which may be optionally employed in combination with compounds of formula I of the invention include non-steroidal anti-inflammatory drugs (NSAIDs) such as ibuprofen, cox-2 inhibitors such as celecoxib, rofecoxib, aspirin, naproxen, ketoprofen, diclofenac sodium, indomethacin, piroxicam, steroids such as prednisone, dexamethasone, hydrocortisone, triamcinolone diacetate, gold compounds, such as gold sodium thiomalate, TNF-α inhibitors such as tenidap, anti-TNF antibodies or soluble TNF receptor, and rapamycin (sirolimus or Rapamune) or derivatives thereof, infliximab (Remicade® Centocor, Inc.). CTLA-4Ig, LEA29Y, antibodies such as anti-ICAM-3, anti-IL-2 receptor (Anti-Tac), anti-CD45RB, anti-CD2, anti-CD3 (OKT-3), anti-CD4, anti-CD80, anti-CD86, monoclonal antibody OKT3, agents blocking the interaction between CD40 and CD154 (a.k.a. "gp39"), such as antibodies specific for CD40 and/or CD154, fusion proteins such as etanercept, fusion proteins constructed from CD40 and/or CD154gp39 (e.g. CD40Ig and CD8gp39), inhibitors, such as nuclear translocation inhibitors, of NF-kappa B function, such as deoxyspergualin (DSG).

The anti-fungal agents which may be optionally employed in combination with compounds of formula I of the invention include fluconazole, miconazole, amphotericin B, and the like.

The antibiotics which may be optionally employed in combination with compounds of formula I of the invention include penicillin, tetracycline, amoxicillin, ampicillin, erythromycin, doxycycline, vancomycin, minocycline, clindamycin or cefalexin.

The anti-vascular hyperproliferation agents which may be optionally employed with compounds of formula I of the invention include methotrexate, leflunomide, FK506 (tacrolimus, Prograf), The hypolipidemic agent or lipid-lowering agent or lipid modulating agents which may be optionally employed in combination with the compounds of formula I of the invention may include 1, 2, 3 or more MTP inhibitors, HMG CoA reductase inhibitors, squalene synthetase inhibitors, fibric acid derivatives, ACAT inhibitors, lipoxygenase inhibitors, cholesterol absorption inhibitors, ileal Na$^+$/bile acid cotransporter inhibitors, upregulators of LDL receptor activity, bile acid sequestrants, and/or nicotinic acid and derivatives thereof.

MTP inhibitors employed herein include MTP inhibitors disclosed in U.S. Pat. No. 5,595,872, U.S. Pat. No. 5,739,135, U.S. Pat. No. 5,712,279, U.S. Pat. No. 5,760,246, U.S. Pat. No. 5,827,875, U.S. Pat. No. 5,885,983 and U.S. application Ser. No. 09/175,180 filed Oct. 20, 1998, now U.S. Pat. No. 5,962,440. Preferred are each of the preferred MTP inhibitors disclosed in each of the above patents and applications.

All of the above U.S. patents and applications are incorporated herein by reference.

Most preferred MTP inhibitors to be employed in accordance with the present invention include preferred MTP inhibitors as set out in U.S. Pat. Nos. 5,739,135 and 5,712,279, and U.S. Pat. No. 5,760,246.

The most preferred MTP inhibitor is 9-[4-[4-[[2-(2,2,2-trifluoroethoxy)benzoyl]amino]-1-piperidinyl]butyl]-N-(2,2,2-trifluoroethyl)-9H-fluorene-9-carboxamide

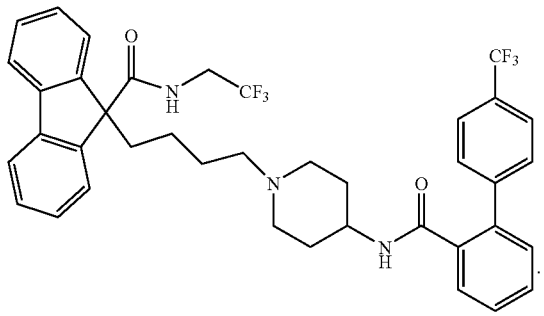

The hypolipidemic agent may be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, itavastatin (Nissan/Sankyo's nisvastatin (NK-104)) disclosed in U.S. Pat. No. 5,011,930, Shionogi-Astra/Zeneca visastatin (ZD-4522) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propanephosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0,142,146 A2, and quinoline and pyridine derivatives disclosed in U.S. Pat. Nos. 5,506,219 and 5,691,322.

In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller et al, *J. Med. Chem., Vol.* 31, No. 10, pp 1869-1871 (1988), including isoprenoid (phosphinyl-methyl)phosphonates as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., *Current Pharmaceutical Design,* 2, 1-40 (1996).

In addition, other squalene synthetase inhibitors suitable for use herein include the terpenoid pyrophosphates disclosed by P. Ortiz de Montellano et al, J. Med. Chem., 1977, 20, 243-249, the farnesyl diphosphate analog A and presqualene pyrophosphate (PSQ-PP) analogs as disclosed by Corey and Volante, *J. Am. Chem. Soc.,* 98, 1291-1293 (1976), phosphinylphosphonates reported by McClard, R. W. et al, *J. Am. Chem. Soc.,* 1987, 109, 5544 (1987), and cyclopropanes reported by Capson, T. L., PhD dissertation, Dept. Med. Chem. U of Utah, Abstract, Table of Contents, pp 16, 17, 40-43, 48-51, Summary (June, 1987).

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (Secholex®, Policexide®) and cholestagel (Sankyo/Geltex), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid (niacin), acipimox, acifran, neomycin, p-aminosalicylic acid, aspirin, poly(diallylmethylamine) derivatives such as disclosed in U.S. Pat. No. 4,759,923, quaternary amine poly (diallyldimethylammonium chloride) and ionenes such as disclosed in U.S. Pat. No. 4,027,009, and other known serum cholesterol lowering agents.

The hypolipidemic agent may be an ACAT inhibitor such as disclosed in, Drugs of the Future 24, 9-15 (1999), (Avasimibe); "The ACAT inhibitor, CI-1011 is effective in the prevention and regression of aortic fatty streak area in hamsters", Nicolosi et al, *Atherosclerosis* (Shannon, Irel). 137(1), 77-85 (1998) "The pharmacological profile of FCE 27677: a novel ACAT inhibitor with potent hypolipidemic activity mediated by selective suppression of the hepatic secretion of ApoB100-containing lipoprotein", Ghiselli, Giancarlo, *Cardiovasc. Drug Rev.* (1998), 16(1), 16-30; "RP 73163: a bioavailable alkylsulfinyl-diphenylimidazole ACAT inhibitor", Smith, C., et al, *Bioorg. Med. Chem. Lett.* 6(1), 47-50 (1996); "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., *Inflammation: Mediators Pathways* 173-98 (1995), Publisher: CRC, Boca Raton, Fla.; "ACAT inhibitors: potential anti-atherosclerotic agents", Sliskovic et al, *Curr. Med. Chem.* 1(3), 204-25 1994); "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl] ureas with enhanced hypocholesterolemic activity", Stout et al, *Chemtracts: Org. Chem.* 8(6), 359-62 (1995), or TS-962 (Taisho Pharmaceutical Co. Ltd).

The hypolipidemic agent may be an upregulator of LD2 receptor activity such as MD-700 (Taisho Pharmaceutical Co. Ltd) and LY295427 (Eli Lilly).

The hypolipidemic agent may be a cholesterol absorption inhibitor preferably Schering-Plough's ezetimibe (SCH58235) and SCH48461 as well as those disclosed in *Atherosclerosis* 115, 45-63 (1995) and *J. Med. Chem.* 41, 973 (1998).

The hypolipidemic agent may be an ileal $Na^+$/bile acid cotransporter inhibitor such as disclosed in *Drugs of the Future*, 24, 425-430 (1999).

The lipid-modulating agent may be a cholesteryl ester transfer protein (CETP) inhibitor such as Pfizer's CP 529,414 (WO/0038722 and EP 818448) and Pharmacia's SC-744 and SC-795.

The ATP citrate lyase inhibitor which may be employed in the combination of the invention may include, for example, those disclosed in U.S. Pat. No. 5,447,954.

Preferred hypolipidemic agents are pravastatin, lovastatin, simvastatin, atorvastatin, fluvastatin, cerivastatin, itavastatin and visastatin and ZD-4522.

The above-mentioned U.S. patents are incorporated herein by reference. The amounts and dosages employed will be as indicated in the Physician's Desk Reference and/or in the patents set out above.

The compounds of formula I of the invention will be employed in a weight ratio to the hypolipidemic agent (were present), within the range from about 500:1 to about 1:500, preferably from about 100:1 to about 1:100.

The dose administered must be carefully adjusted according to age, weight and condition of the patient, as well as the route of administration, dosage form and regimen and the desired result.

The dosages and formulations for the hypolipidemic agent will be as disclosed in the various patents and applications discussed above.

The dosages and formulations for the other hypolipidemic agent to be employed, where applicable, will be as set out in the latest edition of the Physicians' Desk Reference.

For oral administration, a satisfactory result may be obtained employing the MTP inhibitor in an amount within the range of from about 0.01 mg to about 500 mg and preferably from about 0.1 mg to about 100 mg, one to four times daily.

A preferred oral dosage form, such as tablets or capsules, will contain the MTP inhibitor in an amount of from about 1 to about 500 mg, preferably from about 2 to about 400 mg, and more preferably from about 5 to about 250 mg, one to four times daily.

For oral administration, a satisfactory result may be obtained employing an HMG CoA reductase inhibitor, for example, pravastatin, lovastatin, simvastatin, atorvastatin, fluvastatin or cerivastatin in dosages employed as indicated in the Physician's Desk Reference, such as in an amount within the range of from about 1 to 2000 mg, and preferably from about 4 to about 200 mg.

The squalene synthetase inhibitor may be employed in dosages in an amount within the range of from about 10 mg to about 2000 mg and preferably from about 25 mg to about 200 mg.

A preferred oral dosage form, such as tablets or capsules, will contain the HMG CoA reductase inhibitor in an amount from about 0.1 to about 100 mg, preferably from about 0.5 to about 80 mg, and more preferably from about 1 to about 40 mg.

A preferred oral dosage form, such as tablets or capsules will contain the squalene synthetase inhibitor in an amount of from about 10 to about 500 mg, preferably from about 25 to about 200 mg.

The hypolipidemic agent may also be a lipoxygenase inhibitor including a 15-lipoxygenase (15-LO) inhibitor such as benzimidazole derivatives as disclosed in WO 97/12615, 15-LO inhibitors as disclosed in WO 97/12613, isothiazolones as disclosed in WO 96/38144, and 15-LO inhibitors as disclosed by Sendobry et al "Attenuation of diet-induced atherosclerosis in rabbits with a highly selective 15-lipoxygenase inhibitor lacking significant antioxidant properties", *Brit. J Pharmacology* 120, 1199-1206 (1997), and Cornicelli et al, "15-Lipoxygenase and its Inhibition: A Novel Therapeutic Target for Vascular Disease", *Current Pharmaceutical Design*, 5, 11-20 (1999).

The compounds of formula I and the hypolipidemic agent may be employed together in the same oral dosage form or in separate oral dosage forms taken at the same time.

The compositions described above may be administered in the dosage forms as described above in single or divided doses of one to four times daily. It may be advisable to start a patient on a low dose combination and work up gradually to a high dose combination.

The preferred hypolipidemic agent is pravastatin, simvastatin, lovastatin, atorvastatin, fluvastatin or cerivastatin as well as niacin and/or cholestagel.

The other antidiabetic agent which may be optionally employed in combination with the compound of formula I may be 1, 2, 3 or more antidiabetic agents or antihyperglycemic agents including insulin secretagogues or insulin sensitizers, or other antidiabetic agents preferably having a mechanism of action different from the compounds of formula I of the invention, which may include biguanides, sulfonyl ureas, glucosidase inhibitors, PPAR γ agonists, such as thiazolidinediones, aP2 inhibitors, dipeptidyl peptidase IV (DP4) inhibitors, SGLT2 inhibitors, and/or meglitinides, as well as insulin, and/or glucagon-like peptide-1 (GLP-1).

The other antidiabetic agent may be an oral antihyperglycemic agent preferably a biguanide such as metformin or phenformin or salts thereof, preferably metformin HCl.

Where the antidiabetic agent is a biguanide, the compounds of structure I will be employed in a weight ratio to biguanide within the range from about 0.001:1 to about 10:1, preferably from about 0.01:1 to about 5:1.

The other antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the □-cells, with glyburide and glipizide being preferred, which may be administered in the same or in separate oral dosage forms.

The compounds of structure I will be employed in a weight ratio to the sulfonyl urea in the range from about 0.01:1 to about 100:1, preferably from about 0.02:1 to about 5:1.

The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of structure I will be employed in a weight ratio to the glucosidase inhibitor within the range from about 0.01:1 to about 100:1, preferably from about 0.05:1 to about 10:1.

The compounds of structure I may be employed in combination with a PPAR γ agonist such as a thiazolidinedione oral anti-diabetic agent or other insulin sensitizers (which has an insulin sensitivity effect in NIDDM patients) such as troglitazone (Warner-Lambert's Rezulin®, disclosed in U.S. Pat. No. 4,572,912), rosiglitazone (SKB), pioglitazone (Takeda), Mitsubishi's MCC-555 (disclosed in U.S. Pat. No. 5,594,016), Glaxo-Welcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), N,N-2344 (Dr. Reddy/NN), or YM-440 (Yamanouchi), preferably rosiglitazone and pioglitazone.

The compounds of structure I will be employed in a weight ratio to the thiazolidinedione in an amount within the range from about 0.01:1 to about 100:1, preferably from about 0.05 to about 10:1.

The sulfonyl urea and thiazolidinedione in amounts of less than about 150 mg oral antidiabetic agent may be incorporated in a single tablet with the compounds of structure I.

The compounds of structure I may also be employed in combination with a antihyperglycemic agent such as insulin or with glucagon-like peptide-1 (GLP-1) such as GLP-1(1-36) amide, GLP-1(7-36) amide, GLP-1(7-37) (as disclosed in U.S. Pat. No. 5,614,492 to Habener, the disclosure of which is incorporated herein by reference), as well as AC2993 (Amylin) and LY-315902 (Lilly), which may be administered via injection, intranasal, inhalation or by transdermal or buccal devices.

Where present, metformin, the sulfonyl ureas, such as glyburide, glimepiride, glipyride, glipizide, chlorpropamide and gliclazide and the glucosidase inhibitors acarbose or miglitol or insulin (injectable, pulmonary, buccal, or oral) may be employed in formulations as described above and in amounts and dosing as indicated in the Physician's Desk Reference (PDR).

Where present, metformin or salt thereof may be employed in amounts within the range from about 500 to about 2000 mg per day which may be administered in single or divided doses one to four times daily.

Where present, the thiazolidinedione anti-diabetic agent may be employed in amounts within the range from about 0.01 to about 2000 mg/day which may be administered in single or divided doses one to four times per day.

Where present insulin may be employed in formulations, amounts and dosing as indicated by the Physician's Desk Reference.

Where present GLP-1 peptides may be administered in oral buccal formulations, by nasal administration or parenterally as described in U.S. Pat. Nos. 5,346,701 (TheraTech), 5,614,492 and 5,631,224 which are incorporated herein by reference.

The other antidiabetic agent may also be a PPAR α/γ dual agonist such as AR-H039242 (Astra/Zeneca), GW-409544 (Glaxo-Wellcome), KRP297 (Kyorin Merck) as well as those disclosed by Murakami et al, "A Novel Insulin Sensitizer Acts As a Coligand for Peroxisome Proliferation-Activated Receptor Alpha (PPAR alpha) and PPAR gamma. Effect on PPAR alpha Activation on Abnormal Lipid Metabolism in Liver of Zucker Fatty Rats", *Diabetes* 47, 1841-1847 (1998).

The antidiabetic agent may be an SGLT2 inhibitor such as disclosed in U.S. application Ser. No. 09/679,027, filed Oct. 4, 2000 employing dosages as set out therein. Preferred are the compounds designated as preferred in the above application.

The antidiabetic agent may be an aP2 inhibitor such as disclosed in U.S. application Ser. No. 09/391,053, filed Sep. 7, 1999, and in U.S. application Ser. No. 09/519,079, filed Mar. 6, 2000 employing dosages as set out herein. Preferred are the compounds designated as preferred in the above application.

The antidiabetic agent may be a DP4 inhibitor such as disclosed in U.S. application Ser. No. 09/788,173 filed Feb. 16, 2001, WO99/38501, WO99/46272, WO99/67279 (PROBIODRUG), WO99/67278 (PROBIODRUG), WO99/61431 (PROBIODRUG), NVP-DPP728A (1-[[[2-[(5-cyanopyridin-2-yl)amino]ethyl]amino]acetyl]-2-cyano-(S)-pyrrolidine) (Novartis) (preferred) as disclosed by Hughes et al, *Biochemistry,* 38(36), 11597-11603, (1999), TSL-225 (tryptophyl-1,2,3,4-tetrahydro-isoquinoline-3-carboxylic acid (disclosed by Yamada et al, *Bioorg. & Med. Chem. Lett.* 8 1537-1540 (1998), 2-cyanopyrrolidides and 4-cyanopyrrolidides as disclosed by Ashworth et al, *Bioorg. & Med. Chem. Lett.*, Vol. 6, No. 22, pp 1163-1166 and 2745-2748 (1996) employing dosages as set out in the above references.

The meglitinide which may optionally be employed in combination with the compound of formula I of the invention may be repaglinide, nateglinide (Novartis) or KAD1229 (PF/Kissei), with repaglinide being preferred.

The compound of formula I will be employed in a weight ratio to the meglitinide, PPAR γ agonist, PPAR α/γ dual agonist, aP2 inhibitor, DP4 inhibitor or SGLT2 inhibitor within the range from about 0.01:1 to about 100:1, preferably from about 0.05 to about 10:1.

The other type of therapeutic agent which may be optionally employed with a compound of formula I may be 1, 2, 3 or more of an anti-obesity agent including a beta 3 adrenergic agonist, a lipase inhibitor, a serotonin (and dopamine) reuptake inhibitor, an aP2 inhibitor, a thyroid receptor agonist and/or an anorectic agent.

The beta 3 adrenergic agonist which may be optionally employed in combination with a compound of formula I may be AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, with AJ9677, L750,355 and CP331648 being preferred.

The lipase inhibitor which may be optionally employed in combination with a compound of formula I may be orlistat or ATL-962 (Alizyme), with orlistat being preferred.

The serotonin (and dopoamine) reuptake inhibitor which may be optionally employed in combination with a compound of formula I may be sibutramine, topiramate (Johnson & Johnson) or axokine (Regeneron), with sibutramine and topiramate being preferred.

The thyroid receptor agonist which may be optionally employed in combination with a compound of formula I may be a thyroid receptor ligand as disclosed in WO97/21993 (U. Cal SF), WO99/00353 (KaroBio), GB98/284425 (KaroBio), and U.S. Provisional Application 60/183,223 filed Feb. 17, 2000, with compounds of the KaroBio applications and the above U.S. provisional application being preferred.

The anorectic agent which may be optionally employed in combination with a compound of formula I may be dexamphetamine, phentermine, phenylpropanolamine or mazindol, with dexamphetamine being preferred.

The various anti-obesity agents described above may be employed in the same dosage form with the compound of formula I or in different dosage forms, in dosages and regimens as generally known in the art or in the PDR.

The antihypertensive agents which may be employed in combination with the compound of formula I of the invention include ACE inhibitors, angiotensin II receptor antagonists, NEP/ACE inhibitors, as well as calcium channel blockers, β-adrenergic blockers and other types of antihypertensive agents including diuretics.

The angiotensin converting enzyme inhibitor which may be employed herein includes those containing a mercapto (—S—) moiety such as substituted proline derivatives, such as any of those disclosed in U.S. Pat. No. 4,046,889 to Ondetti et al mentioned above, with captopril, that is, 1-[(2S)-3-mercapto-2-methylpropionyl]-L-proline, being preferred, and mercaptoacyl derivatives of substituted prolines such as any of those disclosed in U.S. Pat. No. 4,316,906 with zofenopril being preferred.

Other examples of mercapto containing ACE inhibitors that may be employed herein include rentiapril (fentiapril, Santen) disclosed in Clin. Exp. Pharmacol. Physiol. 10:131 (1983); as well as pivopril and YS980.

Other examples of angiotensin converting enzyme inhibitors which may be employed herein include any of those disclosed in U.S. Pat. No. 4,374,829 mentioned above, with N-(1-ethoxycarbonyl-3-phenylpropyl)-L-alanyl-L-proline, that is, enalapril, being preferred, any of the phosphonate substituted amino or imino acids or salts disclosed in U.S. Pat. No. 4,452,790 with (S)-1-[6-amino-2-[[hydroxy-(4-phenylbutyl)phosphinyl]oxy]-1-oxohexyl]-L-proline or (ceronapril) being preferred, phosphinylalkanoyl prolines disclosed in U.S. Pat. No. 4,168,267 mentioned above with fosinopril being preferred, any of the phosphinylalkanoyl substituted prolines disclosed in U.S. Pat. No. 4,337,201, and the phosphonamidates disclosed in U.S. Pat. No. 4,432,971 discussed above.

Other examples of ACE inhibitors that may be employed herein include Beecham's BRL 36,378 as disclosed in European Patent Application Nos. 80822 and 60668; Chugai's MC-838 disclosed in C.A. 102:72588v and *Jap. J. Pharmacol.* 40:373 (1986); Ciba-Geigy's CGS14824 (3-([1-ethoxycarbonyl-3-phenyl-(1S)-propyl]amino)-2,3,4,5-tetrahydro-2-oxo-1-(3S)-benzazepine-1 acetic acid HCl) disclosed in U.K. Patent No. 2103614 and CGS16,617 (3(S)-[[(1S)-5-amino-1-carboxypentyl]amino]-2,3,4,5-tetrahydro-2-oxo-1H-1-benzazepine-1-ethanoic acid) disclosed in U.S. Pat. No. 4,473,575; cetapril (alacepril, Dainippon) disclosed in Eur. Therap. Res. 39:671 (1986); 40:543 (1986); ramipril (Hoechsst) disclosed in Euro. Patent No. 79-022 and *Curr. Ther. Res.* 40:74 (1986); Ru 44570 (Hoechst) disclosed in *Arzneimittelforschung* 34:1254 (1985), cilazapril (Hoffman-LaRoche) disclosed in *J. Cardiovasc. Pharmacol.* 9:39 (1987); R 31-2201 (Hoffman-LaRoche) disclosed in *FEBS Lett.* 165:201 (1984); lisinopril (Merck), indalapril (delapril) disclosed in U.S. Pat. No. 4,385,051; indolapril (Schering) disclosed in *J. Cardiovasc. Pharmacol.* 5:643, 655 (1983), spirapril (Schering) disclosed in *Acta. Pharmacol. Toxicol.* 59 (Supp. 5):173 (1986); perindopril (Servier) disclosed in *Eur. J. clin. Pharmacol.* 31:519 (1987); quinapril (Warner-Lambert) disclosed in U.S. Pat. No. 4,344,949 and CI925 (Warner-Lambert) ([3S-[2[R(*)R(*)]]3R(*)]-2-[2-[[1-(ethoxy-carbonyl)-3-phenylpropyl]amino]-1-oxopropyl]-1,2,3,4-tetrahydro-6,7-dimethoxy-3-isoquinolinecarboxylic acid HCl)disclosed in *Pharmacologist* 26:243, 266 (1984), WY-44221 (Wyeth) disclosed in *J. Med. Chem.* 26:394 (1983).

Preferred ACE inhibitors are captopril, fosinopril, enalapril, lisinopril, quinapril, benazepril, fentiapril, ramipril and moexipril.

NEP/ACE inhibitors may also be employed herein in that they possess neutral endopeptidase (NEP) inhibitory activity and angiotensin converting enzyme (ACE) inhibitory activity. Examples of NEP/ACE inhibitors suitable for use herein include those disclosed in U.S. Pat. Nos. 5,362,727, 5,366,973, 5,225,401, 4,722,810, 5,223,516, 4,749,688, U.S. Pat. No. 5,552,397, U.S. Pat. No. 5,504,080, U.S. Pat. No. 5,612,359,U.S. Pat. No. 5,525,723, European Patent Application 0599,444, 0481,522, 0599,444, 0595,610, European Patent Application 0534363A2, 534,396 and 534,492, and European Patent Application 0629627A2.

Preferred are those NEP/ACE inhibitors and dosages thereof which are designated as preferred in the above patents/applications which U.S. patents are incorporated herein by reference; most preferred are omapatrilat, BMS 189,921 ([S-(R*,R*)]-hexahydro-6-[(2-mercapto-1-oxo-3-phenylpropyl)amino]-2,2-dimethyl-7-oxo-1H-azepine-1-acetic acid (gemopatrilat)) and CGS 30440.

The angiotensin II receptor antagonist (also referred to herein as angiotensin II antagonist or AII antagonist) suitable for use herein includes, but is not limited to, irbesartan, losartan, valsartan, candesartan, telmisartan, tasosartan or eprosartan, with irbesartan, losartan or valsartan being preferred.

A preferred oral dosage form, such as tablets or capsules, will contain the ACE inhibitor or AII antagonist in an amount within the range from abut 0.1 to about 500 mg, preferably from about 5 to about 200 mg and more preferably from about 10 to about 150 mg.

For parenteral administration, the ACE inhibitor, angiotensin II antagonist or NEP/ACE inhibitor will be employed in an amount within the range from about 0.005 mg/kg to about 10 mg/kg and preferably from about 0.01 mg/kg to about 1 mg/kg.

Where a drug is to be administered intravenously, it will be formulated in conventional vehicles, such as distilled water, saline, Ringer's solution or other conventional carriers.

It will be appreciated that preferred dosages of ACE inhibitor and AII antagonist as well as other antihypertensives disclosed herein will be as set out in the latest edition of the Physician's Desk Reference (PDR).

Other examples of preferred antihypertensive agents suitable for use herein include omapatrilat (Vanlev®) amlodipine besylate (Norvasc®), prazosin HCl (Minipress®), verapamil, nifedipine, nadolol, diltiazem, felodipine, nisoldipine, isradipine, nicardipine, atenolol, carvedilol, sotalol, terazosin, doxazosin, propranolol, and clonidine HCl (Catapres®).

Diuretics which may be employed in combination with compounds of formula I include hydrochlorothiazide, torasemide, furosemide, spironolactono, and indapamide.

Antiplatelet agents which may be employed in combination with compounds of formula I of the invention include aspirin, clopidogrel, ticlopidine, dipyridamole, abciximab, tirofiban, eptifibatide, anagrelide, and ifetroban, with clopidogrel and aspirin being preferred.

The antiplatelet drugs may be employed in amounts as indicated in the PDR. Ifetroban may be employed in amounts as set out in U.S. Pat. No. 5,100,889.

Antiosteoporosis agents suitable for use herein in combination with the compounds of formula I of the invention include parathyroid hormone or bisphosphonates, such as MK-217 (alendronate) (Fosamax®).

Dosages employed for the above drugs will be as set out in the Physician's Desk Reference.

Pharmaceutical Formulations

The pharmaceutical composition of the invention includes a pharmaceutically acceptable carrier, adjuvant or vehicle that may be administered to a subject, together with a compound of the present invention, and which does not destroy the pharmacological activity thereof. Pharmaceutically acceptable carriers, adjuvants and vehicles that may be used in the pharmaceutical compositions of the present invention include, but are not limited to, the following: ion exchangers, alumina, aluminum stearate, lecithin, self-emulsifying drug delivery systems ("SEDDS") such as d(-tocopherol polyethyleneglycol 1000 succinate), surfactants used in pharmaceutical dosage forms such as Tweens or other similar polymeric delivery matrices, serum proteins such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as $\alpha$-, $\beta$- and $\gamma$-cyclodextrin, or chemically modified derivatives such as hydroxyalkylcyclodextrins, including 2- and 3-hydroxypropyl-$\beta$-cyclodextrins, or other solubilized derivatives may also be used to enhance delivery of the modulators of the present invention.

The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the invention may be administered by any suitable means, for example, orally, such as in the form of tablets, capsules, granules or powders; sublingually; buccally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The compounds of the invention may, for example, be administered in a form suitable for immediate release or extended release. Immediate release or extended release may be achieved by the use of suitable pharmaceutical compositions including the compounds of the invention, or, particularly in the case of extended release, by the use of devices such as subcutaneous implants or osmotic pumps. The compounds of the invention may also be administered liposomally.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The present compounds may also be delivered through the oral cavity by sublingual and/or buccal administration. Molded tablets, compressed tablets or freeze-dried tablets are exemplary forms which may be used. Exemplary compositions include those formulating the compound(s) of the invention with fast dissolving diluents such as mannitol, lactose, sucrose and/or cyclodextrins. Also included in such formulations may be high molecular weight excipients such as celluloses (Avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

Exemplary compositions for rectal administration include suppositories which may contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human of from about 0.1 to 500 mg/kg of body weight of active compound per day, or between 5 and 2000 mg per day which may be administered in a single dose or in the form of individual divided doses, such as from 1 to 5 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like.

A typical capsule for oral administration contains compounds of structure I (250 mg), lactose (75 mg) and magnesium stearate (15 mg). The mixture is passed through a 60 mesh sieve and packed into a No. 1 gelatin capsule.

A typical injectable preparation is produced by aseptically placing 250 mg of compounds of structure I into a vial, aseptically freeze-drying and sealing. For use, the contents of the vial are mixed with 2 mL of physiological saline, to produce an injectable preparation.

The compounds of formula I of the invention are glucocorticoid receptor modulators as shown either by their ability to bind glucocorticoid receptors in GR binding assays, or by their ability to inhibit AP-1 activity as indicated in cellular transrespressional assays, and cause none to minimal transactivation as indicated in cellular transscriptional assays.

Compounds of the invention, including the compounds described in the examples hereof, have been tested in at least one of the assay(s) described below and have glucocorticoid receptor (GR)/Dexamethasone (Dex) inhibition activity (>95% at 10 µM) and/or AP-1 inhibition activity ($EC_{50}$ at less than 15 µM).

Identical and/or similar assays are described in copending provisional application No. 60/396,907, filed Jul. 18, 2002 which is incorporated in its entirety herein by reference.

GR (Dex) Binding Assay

In order to measure the binding of compounds to Site I on the glucocorticoid receptor a commercially available kit was used (Glucocorticoid receptor competitor assay kit, Panvera Co., Madison, Wis.). Briefly, a cell lysate containing recombinantly expressed human full-length glucocorticoid receptor was mixed with a fluorescently labeled glucocorticoid (4 nM FITC-dexamethasone) plus or minus test molecule. After one hour at room temperature, the fluorescence polarization (FP) of the samples were measured. The FP of a mixture of receptor, fluorescent probe (i.e. FITC-dexamethasone) and 1 mM dexamethasone represented background fluorescence or 100% inhibition, whereas, the FP of the mixture without dexamethasone was taken to be 100% binding. The percentage inhibition of test molecules were then compared to the sample with 1 mM dexamethasone and expressed as % relative binding activity with dexamethasone being 100% and no inhibition is 0%. Test molecules were analyzed in the concentration range from 0.1 nM to 40 µM.

Site I binding assays for any NHR (Nuclear Hormone Receptor) are conducted similarly to the above. An appropriate cell lysate or purified NHR is used as the source of the NHR. The fluorescent probe and unlabeled competitor are appropriate for the specific NHR, i.e. are ligands for the specific NHR.

Cellular Transrepressional Assay

To measure the ability of test molecules to inhibit AP-1 induced transcriptional activity we utilized an A549 cell which was stably transfected with a plasmid containing 7xAP-1 DNA binding sites (pAP-1-Luc plasmid, Stratagene Co. La Jolla, Calif.) followed by the gene for luciferase. Cells were activated with 10 ng/ml of phorbol myristic acid (PMA) plus or minus test molecules for 7 hours. After 7 hours a luciferase reagent was added to measure luciferase enzymatic activity in the cell. After a 10 minute incubation of luciferase reagent with cells, luminescence was measured in a TopCount luminescence counter. Repression of AP-1 activity was calculated as the percentage decrease in the signal induced by PMA alone. Test molecules were analyzed in the concentration range from 0.1 nM to 40 µM. $EC_{50}$s were determined by using standard curve fitting methods such as Excel fit (Microsoft Co.). An $EC_{50}$ is the test molecule concentration at which there is a 50% repression of the maximal inhibition of transcription, i.e. a 50% reduction of AP-1 activity.

Other reporters and cell lines also may be used in a cellular transrepressional assay. A similar assay is performed in which NF-κB activity is measured. A plasmid containing NF-κB DNA binding sites is used, such as pNF-kB-Luc, (Stratagene, LaJolla Calif.), and PMA or another stimulus, such as TNF-α or lipopolysaccharide, is used to activate the NF-κB pathway. NF-κB assays similar to that described in Yamamoto K., et al., *J Biol Chem Dec* 29; 270(52):31315-20 (1995) may be used.

The cellular transrepressional assays described above may be used to measure transrepression by any NHR. One of skill in the art will understand that assays may require the addition of components, such as a stimulus (eg. PMA, lipopolysaccharide, TNF-α, etc) which will induce transcription mediated by AP-1 or NF-κB. Additionally, AR mediated transrepression may be measured by the assay described in Palvimo J J, et al. *J Biol Chem Sep* 27; 271(39):24151-6 (1996), and PR mediated transrepression may be measured by the assay described in Kalkhoven E., et al. *J Biol Chem Mar* 15; 271(11):6217-24 (1996).

Preparations

The preparations set out below are for the synthesis of reagents that were not obtained from commercial sources and were employed for the preparation of compounds of formula I of the invention. All chemical structures in the tables and schemes are racemic unless specified otherwise.

General Procedure: Purification by Reverse-Phase Preparative HPLC

Reverse-phase preparative high performance liquid chromatography ("HPLC") was performed with Shimadzu 8A liquid chromatographs using YMC S5 ODS columns (20× 100, 20×250, or 30×250 millimeter ("mm")). Gradient elution was performed with methanol/water mixtures in the presence of 0.1% trifluoroacetic acid ("TFA").

Analytical HPLC Methods Employed in Characterization of Examples

Analytical HPLC was performed on Shimadzu LC10AS liquid chromatographs using either of the following methods:

Method A:

Linear gradient of 0 to 100% solvent B over 4 minutes ("min"), with 1 min hold at 100% B.

Ultraviolet ("UV") visualization at 220 nanometers ("nm")

Column: YMC S5 ODS Ballistic 4.6×50 mm

Flow rate: 4 milliliters ("ml")/min

Solvent A: 0.2% phosphoric acid, 90% water, 10% methanol ("MeOH")

Solvent B: 0.2% phosphoric acid, 90% methanol, 10% water

Method B:

Linear gradient of 0 to 100% solvent B over 2 min, with 1 min hold at 100% B.

UV visualization at 220 nm

Column: Phenomenex 4.6×30 mm

Flow rate: 5 ml/min

Solvent A: 0.1% trifluoroacetic acid, 90% water, 10% methanol

Solvent B: 0.1% trifluoroacetic acid, 90% methanol, 10% water

Preparation 1

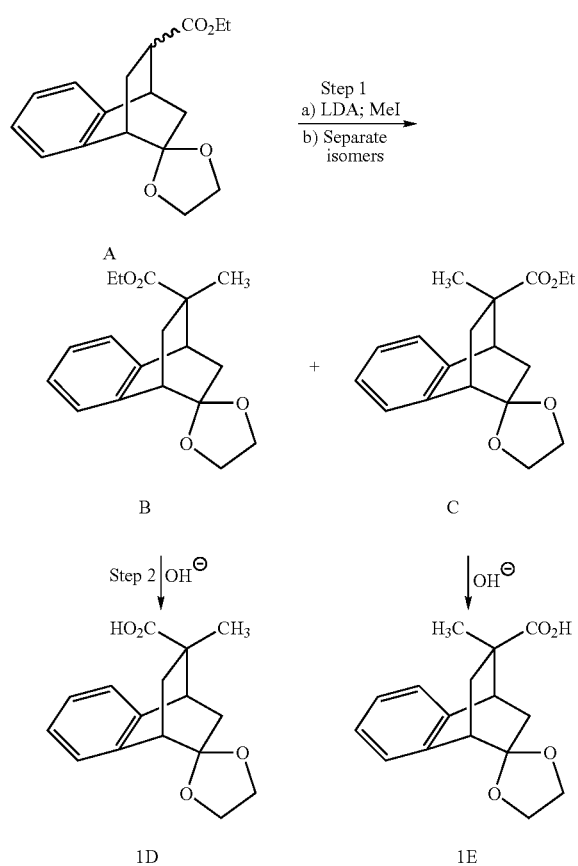

The mixture of diastereomeric esters A was prepared in the manner described in J. Barrish et al., *Bioorganic and Medicinal Chemistry*, 1(4), 309 (1993).

Step 1

To a solution of a mixture of diastereomeric esters 1A [5.92 grams ("g"), 20.6 millimoles ("mmol")] in tetrahydrofuran ("THF", 150 mL) at −78° C. under nitrogen was added a solution of lithium diisopropyl amide (1.8 M in heptane, THF, ethylbenzene, 12.6 mL) dropwise via syringe. Upon completion of addition, the reaction mixture was warmed over a 35 min period to −55° C. where it stirred for 30 min. At the conclusion of this period, methyl iodide (3.2 mL, 5.15 mmol) was added via syringe. The resulting mixture was stirred for ten minutes and then quenched with a saturated aqueous ammonium chloride solution (20 mL). The reaction mixture was allowed to warm to above 0° C. Once at the prescribed temperature, the reaction mixture was partitioned between ethyl acetate (200 mL) and water (100 mL). The organic layer was separated, washed sequentially with aqueous HCl (1 N), saturated aqueous sodium bicarbonate and brine, dried over sodium sulfate, and concentrated in vacuo to yield a residue. The residue (6.37 g) was subjected to flash column chromatography (silica, 15% ethyl acetate in hexanes, then 20% ethyl acetate in hexanes) to provide the separated isomers. Isomer 1B was first to elute (1.59 g, 26% yield) and was obtained as a white solid. Isomer 1C (2.54 g, 41% yield) eluted second and was obtained as an oil. A mixed fraction (1.1 g, 18%) containing nearly equal parts of isomers 1B and 1C was also obtained.

1B: Mass Spectrometry ("MS") (E+) m/z: 303 (MH$^+$); Proton nuclear magnetic resonance ("$^1$H NMR") in chloroform ("CDCl$_3$") δ 7.10 (m, 4H), 3.80-3.95 (m, 6H), 3.20 (dd, 1H), 2.92 (dd, 1H), 2.35 (dd, 1H), 2.27 (dd, 1H), 1.81 (dd, 1H), 1.65 (dd, 1H), 1.40 (s, 3H), 1.02 (t, 3H). NMR spectral data: s=singlet; d=doublet; m=multiplet; br=broad; t=triplet.

1C: MS (E+) m/z: 325 (M+Na$^+$); $^1$H NMR (CDCl$_3$) δ 7.09-7.18 (m, 4H), 4.18 (q, 2H), 3.75-3.93 (m, 4H), 3.20 (dd, 1H), 2.97 (dd, 1H), 2.91 (dd, 1H), 1.96 (dd, 1H), 1.70 (dd, 1H), 1.23 (t, 3H), 1.07 (dd, 1H), 0.76 (s, 3H).

Step 2

A solution of isomer 1B of Step 1 (0.90 g, 2.98 mmol) in a mixture of THF (8.6 mL), water (2.9 mL) and methanol (2.9 mL) was treated with lithium hydroxide monohydrate (749 milligrams ("mg"), 17.86 mmol) and heated at 80° C. in a sealed reaction vessel for 24 h. After this time, the reaction mixture was then concentrated to yield a residue. The residue was partitioned between dichloromethane and aqueous sodium hydroxide (1 N). The aqueous layer was separated, cooled in an ice bath and acidified to approximately pH 2 via the dropwise addition of concentrated hydrochloric acid ("HCl"). The resulting cloudy mixture was washed with ethyl acetate. The organic layer was separated, washed with an aqueous saturated sodium chloride solution ("brine"), dried over sodium sulfate, and concentrated to provide product 1D (540 mg, 66% yield) as a white solid. MS (E+) m/z: 275 (MH$^+$); $^1$H NMR in deuterated methanol ("CD$_3$OD") δ 6.98-7.00 (m, 4H), 3.72-3.98 (m, 4H), 3.13 (dd, 1H), 2.90 (dd, 1H), 2.26 (dd, 1H), 2.18 (dd, 1H), 1.75 (dd, 1H), 1.54 (dd, 1H), 1.36 (s, 3H).

A stirred solution of isomer 1C of Step 1 (2.28 g, 7.55 mmol) in a mixture of THF (23 mL), water (7.8 mL) and methanol (7.8 mL) was treated with lithium hydroxide monohydrate (1.9 g, 45.3 mmol) and heated to 80° C. in a sealed reaction vessel where it stirred for 24 h. At the conclusion of this period, the reaction mixture was worked up following the same procedure set forth above for the preparation of product 1D to provide product 1E (2.0 g, 97% yield) as a white, crystalline solid. MS (E+) m/z: 275 (MH$^+$); $^1$H NMR (CD$_3$OD) δ 7.04-7.07 (m, 4H), 3.68-3.85 (m, 4H), 3.09 (dd, 1H), 2.88 (dd, 1H), 2.84 (dd, 1H), 2.05 (dd, 1H), 1.55 (dd, 1H), 0.94 (dd, 1H), 0.68 (s, 3H).

Preparation 2

The racemic mixture of carboxylic acid 1E (413 mg) of Preparation 1 was separated by chiral HPLC (Chiralpak AD, 50×500 mm, 9:1:0.01 hexanes:isopropanol:TFA, isocratic, 50 mL/min, observed at 220 nm). Enantiomer A eluted first and was obtained as a white solid (173 mg, 42%). Enantiomer B eluted second and was obtained as a white solid (141 mg, 34%). Chiral analytical liquid chromatography ("LC") (Chiralpak AD, 250×4.6 mm, 9:1:0.01 hexanes:isopropanol: TFA, isocratic, 1 mL/min, observed at 220 nm) of enantiomer A showed >99% ee, retention time ("Rt")=5.7 min. Chiral analytical LC (same conditions as for enantiomer A) of enantiomer B revealed >99% ee, retention time=7.7 min.

Preparation 3

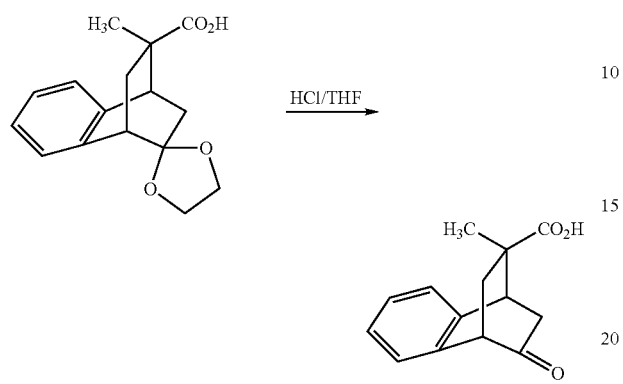

A stirred solution of the product 1E of Preparation 1 (40 mg, 0.15 mmol) in THF (2 mL) and 1N HCl (2 mL) was heated to 60° C. where it stirred for 16 h. At the conclusion of this period, the reaction mixture was concentrated in vacuo and diluted with ethyl acetate. The organic layer was dried over sodium sulfate and concentrated to provide the title compound as a solid (33 mg, 95% yield). MS (E+) m/z: 231 (MH+); LC retention time (Method A): 2.73 min.

Preparation 4

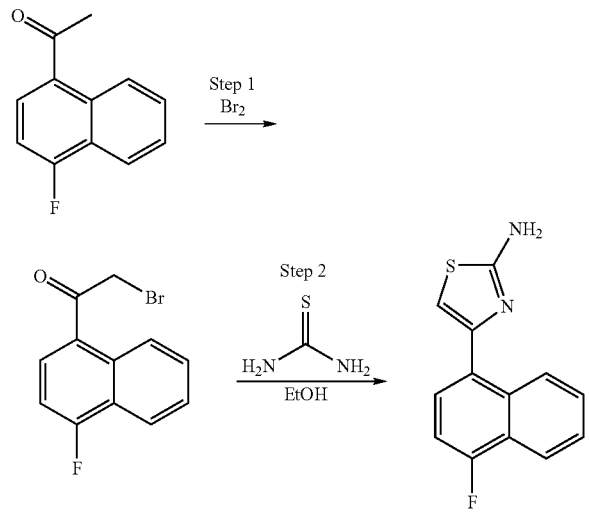

Step 1

To a stirred solution of 4'-fluoro-1'-acetonaphthone (28.69 mmol, 5.4 g) in 1,4-dioxane (18.0 mL) at 0° C. was added bromine (35.13 mmol, 5.61 g). Upon completion of addition, the reaction mixture was allowed to warm to room temperature ("rt") where it stirred for 3 hours. After this time, the reaction mixture was concentrated in vacuo to yield 7.66 g (yield ("Y"): 100%) of the product of Step 1.

Step 2

To a stirred solution of the product of Step 1 (28.69 mmol, 7.66 g) in ethyl alcohol ("EtOH", 20 mL) at room temperature was added thiourea (36.13 mmol, 2.75 g). Upon completion of addition, the mixture was stirred for one hour ("hr" or "h") at which time a precipitate formed. Water (100 mL) was added, and the resulting solid was collected by vacuum filtration. The solid was washed with water (3×100 mL) followed by dichloromethane (3×100 mL) and then dried in vacuo to yield 5.5 g (Y: 75%) of the title compound. MS (E+) m/z: 245 (MH+).

Preparation 5

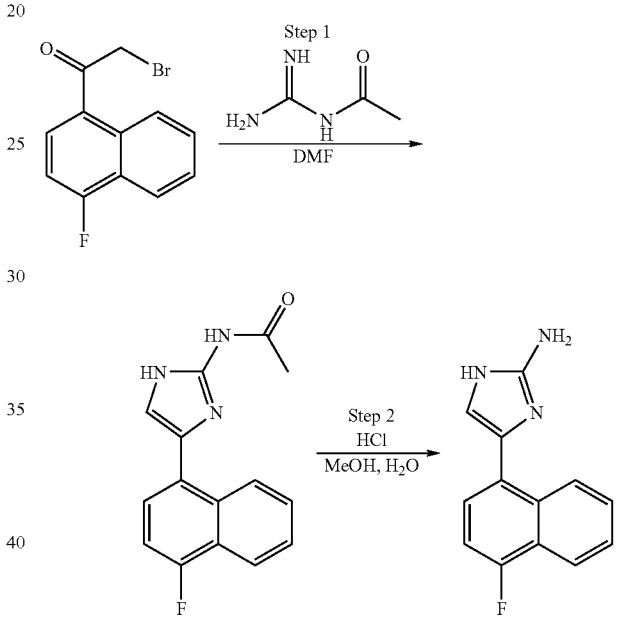

Step 1

To a solution of the product of Preparation 1, Step 1 (18.73 mmol, 5.0 g) in dimethylformamide ("DMF", 15 mL) at room temperature was added 1-acetylguanidine (57.43 mmol, 5.80 g). After 5 hours at room temperature, the reaction mixture was diluted with water (100 mL) and extracted with ethyl acetate (3×100 mL). The organic phases were concentrated in vacuo to yield a residue. The residue was chromatographed on silica gel (eluted with 5% methanol in dichloromethane) to provide 2.0 g (Y: 39%) of the product of step 1. MS (E+) m/z: 270 (MH+).

Step 2

To a solution of the product of Step 1 (7.43 mmol, 2.0 g) in methanol (17 mL) was added water (8.5 mL) and 12 N HCl (12.0 mL). Upon completion of addition, the reaction mixture was heated to reflux where it stirred for one hour. After this time, the reaction mixture was concentrated in vacuo to approximately 15 mL. The resulting solution was purified and neutralized by cation exchange solid phase extraction ("SPE") to provide 1.66 g (Y: 99%) of the title compound 2a. MS (E+) m/z: 228 (MH⁺).

Preparation 6

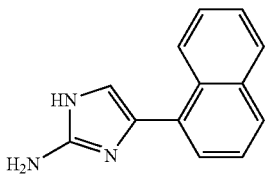

The title compound was prepared in the manner of the title compound of Preparation 5.

Preparation 7

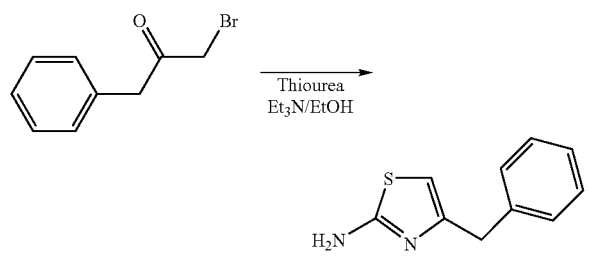

To a stirred solution of 1-bromo-3-phenyl-2-propanone (2.2 g, 10 mmol) (prepared in the manner described in Choi et al., *Org. Lett.* 2003, vol. 5, no. 4, 411-414), in EtOH (100 mL) was added thiourea (1.0 g, 13 mmol). Upon completion of addition, the reaction was heated to reflux where it stirred for 20 h. After this time, the reaction mixture was concentrated in vacuo and partitioned between water and ethyl acetate ("EtOAc"). The aqueous layer was washed with EtOAc (3×). The combined organic extracts were dried over magnesium sulfate ("MgSO₄"), filtered, and concentrated by rotary evaporation. The resulting solid was purified by silica gel chromatography using 10% MeOH/EtOAc as the eluent to yield 2.1 g of a pale yellow solid (95% yield). MS found: (M+H)⁺=191. ¹H-NMR (CDCl3) δ 7.2-7.35 m (5H), 6.01 (s, 1H), 4.8-5.3 (bs, 2H), 3.86 (s, 2H).

Preparation 8

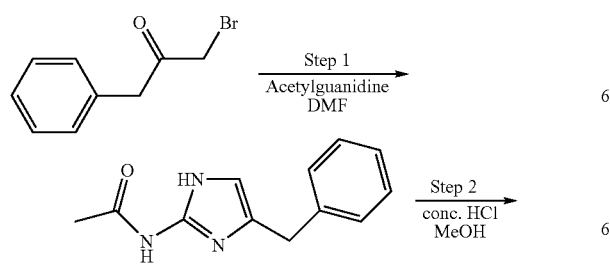

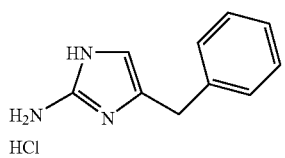

Step 1

A solution of 1-bromo-3-phenyl-2-propanone (9.6 g, 48 mmol) (prepared in the manner described in Choi et al., *Org. Lett.* 2003, vol. 5, no. 4, 411-414) in DMF (50 mL) was added dropwise at 0° C. to a solution of acetylguanidine (10 g, 100 mmol) in DMF (50 mL). Upon completion of addition, the reaction mixture was warmed to rt where it stirred for 20 h. After this time, the reaction mixture was concentrated in vacuo to yield a residue. The residue was triturated in EtOAc/hexanes (2:1). The resulting solid was collected by filtration, washed with EtOAc, and dried in vacuo to yield 1.25 g of an off-white solid (13% yield). MS found: (M+H)⁺=216. ¹H-NMR (DMSO) δ 11.1 bs (1H), 10.9 bs (1H), 7.0-7.18 m (5H), 6.32 (s, 1H), 3.61 (s, 2H), 1.90 (s, 3H).

Step 2

A stirred solution of the product of Step 1 (1.25 g, 5.8 mmol) in 30 mL of a solution of conc. HCl and MeOH (1:2) was heated to reflux where it stirred for 4 hr. At the conclusion of this period, the reaction mixture was concentrated by rotary evaporation and the resulting solid dried in vacuo to yield 1.2 g of a pale yellow solid as the HCl salt (100% yield). MS found: (M+H)⁺=174.

Preparation 9

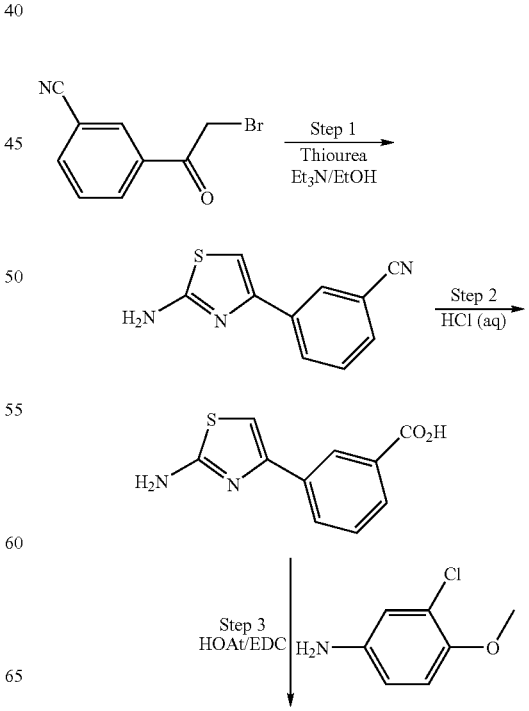

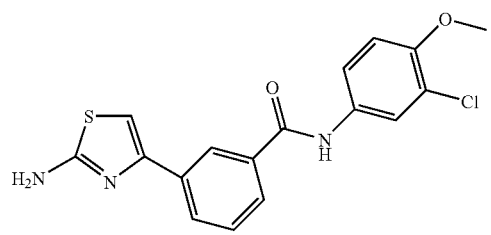

Step 1

To a stirred solution of 3-(2-bromoacetyl)benzonitrile (15.0 g, 66.6 mmol) (prepared in the manner described in Tanaka et al., *J. Med. Chem.* 1998, 41, 2390-2410) in EtOH (220 mL) was added triethylamine (9.3 mL, 66.6 mmol) and thiourea (6.6 g, 86.6 mmol). Upon completion of addition, the reaction was stirred at rt for 20 h. After this time, the reaction was concentrated in vacuo and partitioned between water and EtOAc. The aqueous layer was washed with EtOAc (3×). The combined organic extracts were washed with saturated ("sat.") sodium bicarbonate ("NaHCO₃"), dried over MgSO₄, filtered, and concentrated by rotary evaporation. The resulting solid was recrystallized from EtOAc and hexane to provide 7.78 g of pale yellow solid in a first batch and 1.87 g of a second batch (72% yield combined). MS found: $(M+H)^+$=202. $^1$H-NMR (DMSO) δ 8.21 s (1H), 8.14 (dd, 1H), 7.72 (dd, 1H), 7.60 (app t, 1H), 7.27 (s, 1H), 7.19 (s, 2H).

Step 2

The product of Step 1 (6.73 g, 33.5 mmol) was suspended in 110 mL of concentrated HCl and heated to reflux while stirring for 4 hr. The homogeneous solution was cooled in an ice bath to form crystals which were filtered, washed with water and dried in vacuo to provide 6.89 g (94% yield) of product. MS found: $(M+H)^+$=221.

Step 3

To a solution of 2-amino-4-(3-carboxyphenyl)-thiazole (6.89 g, 31.3 mmol) in 100 mL of DMF was added triethylamine (8.8 mL, 63 mmol), 1-hydroxy-7-azabenzotriazole ("HOAt") (4.26 g, 31.3 mmol), and 3-ethyl-3'-(dimethylamino)propylcarbodiimide hydrochloride (or 1-(3-dimethylaminopropyl)-3-ethylcarbodiimide hydrochloride) ("EDC") (6.0 g, 31.3 mmol). Upon completion of addition, the reaction mixture was stirred at rt for 25 min and then a solution of 3-chloro-4-anisidine (5.92 g, 37.6 mmol) in 50 mL DMF and 8.8 mL triethylamine was added in one portion. The resulting reaction mixture was stirred for 24 h, concentrated by rotary evaporation, and extracted from brine with three portions of EtOAc. The combined organic phases were dried over MgSO₄ to yield crude product. The crude product was concentrated in vacuo, dissolved in a minimum amount of EtOAc and triturated with hexane. The resulting solid was filtered and trituration was repeated twice to provide a total of 5.7 g (51% yield) of pure product. MS found: $(M+H)^+$=360. $^1$H-NMR (DMSO) δ 10.3 (s, 1H), 8.35 (s, 1H), 8.00 (d, 1H), 7.95 (d, 1H), 7.80 (d, 1H), 7.69 (d, 1H), 7.52 (t, 1H), 7.16 (m, 4H), 3.85 (s, 3H).

Preparation 10

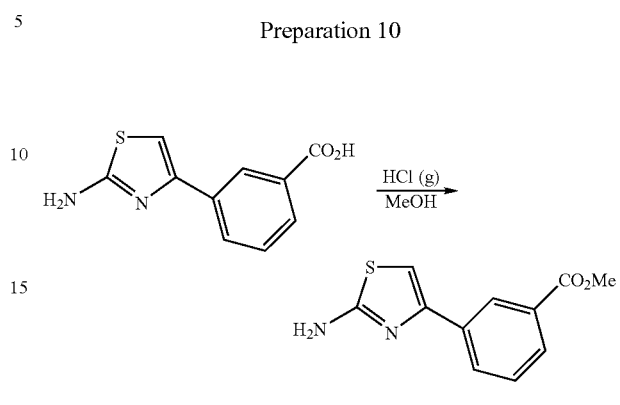

HCl gas was bubbled through anhydrous methanol (25 mL) at 0° C. for 15 min. The gas flow was then ceased and the carboxylic acid of Step 2 of Preparation 9 (500 mg, 2.27 mmol) was added. Upon completion of addition, the reaction mixture was stirred at room temperature for 20 h. At the conclusion of this period, the reaction mixture was concentrated to yield a residue. The residue was purified by flash column chromatography on silica (gradient of 5% methanol, 1% conc. ammonium hydroxide, 94% dichloromethane to 12% methanol, 1% conc. ammonium hydroxide, 87% dichloromethane over 15 min) to provide the title compound as a solid (540 mg, 99% yield). MS (E+) m/z: 218 (MH⁺); LC retention time (Method A): 1.71 min.

Preparation 11

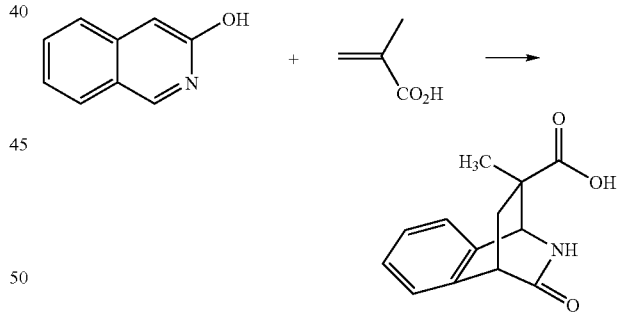

In a sealed reaction vessel, a mixture of 3-hydroxy isoquinoline (10 g, 69 mmol) and methacrylic acid (11.7 mL, 138 mmol) in toluene (150 mL) was heated at 170° C. for 3.5 h. At the conclusion of this period, the volatiles were removed under reduced pressure and the residual oil was triturated with diethyl ether to yield a solid (7 g). The solid was filtered, and the filtrate was concentrated and triturated from diethyl ether to provide a second crop a solid (3 g). The solids were combined, taken up in hot ethanol, and filtered. The filtrate was concentrated to yield a reddish-yellow solid. The reddish-yellow solid was suspended in a solution of 10% ethyl acetate in diethyl ether, and filtered to provide the title compound as a pale yellow solid (6.45 g, 40% yield). MS (E+) m/z: 232

(MH+). 1H NMR (CD3OD) δ 7.38-7.27 (m, 4H), 4.81 (s, 1H), 3.71 (dd, 1H), 2.96 (dd, 1H), 1.32 (dd, 1H), 0.94 (s, 3H).

Preparation 12

The racemic carboxylic acid of Preparation 11 (750 mg) was resolved into separated enantiomers by chiral preparative HPLC (Chiralpak AD, 50×500 mm, 50 mL/min, 19.9% 1:1 ethanol:methanol in 80% heptane with 0.1% TFA, isocratic, observed at 220 nm). Enantiomer A eluted at 33-38 min, while enantiomer B eluted at 80-90 min. Enantiomer A was obtained as a white solid (217 mg) with ee>99% (AD, 4.6×50 mm, 1 mL/min, 19.9% 1:1 ethanol:methanol in 80% heptane with 0.1% TFA, retention time=7.97 min). Enantiomer B was obtained as a white solid (137 mg) with ee>99% (AD, 4.6×50 mm, 1 mL/min, 19.9% 1:1 ethanol:methanol in 80% heptane with 0.1% TFA, retention time=16 min).

Preparation 13

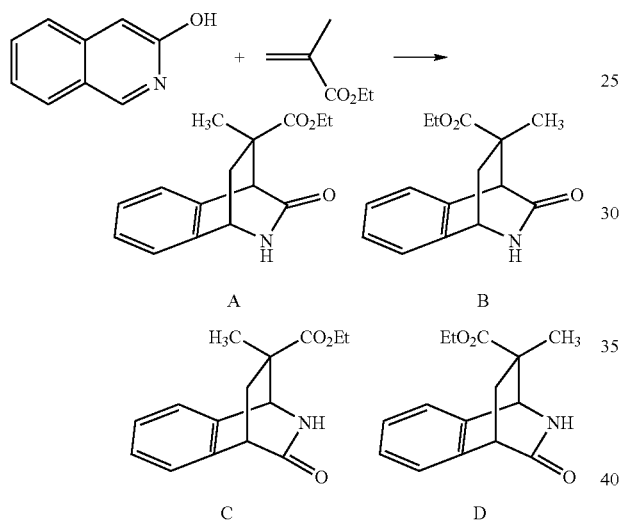

In a sealed reaction vessel, a stirred mixture of 3-hydroxy-isoquinoline (500 mg, 3.44 mmol) and ethyl methacrylate (1.29 mL, 10.3 mmol) in toluene (10 mL) was heated to 170° C. where it stirred for 16 h. After this time, the reaction mixture was concentrated to yield crude product. The crude product was purified by preparative HPLC to provide a fraction containing isomers A and B in a 3:1 ratio (A:B) as an oil (284 mg, 32% yield). MS (E+) m/z: 260 (MH+); LC retention time (Method A): 2.41 min (broad).

A second fraction containing isomers C and D in a 5:1 ratio (C:D) was obtained as a solid (502 mg, 56%). MS (E+) m/z: 260 (MH+); LC retention time (Method A): 2.70 min (broad).

Preparation 14

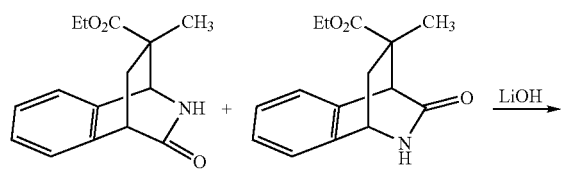

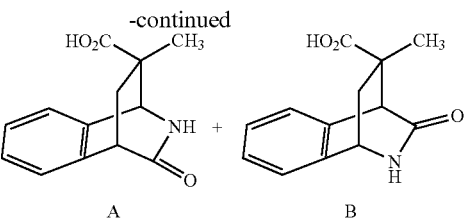

To a stirred solution of the fraction of Preparation 13 containing isomers A and B (10 mg, 0.039 mmol) in a mixture of THF (0.2 mL), methanol (0.7 mL) and water (0.7 mL) was added lithium hydroxide monohydrate (6.5 mg, 0.15 mmol). Upon completion of addition, the reaction mixture was heated to 70° C. where it stirred for 6 h. At the conclusion of this period, the reaction mixture was partitioned between aqueous HCl (1 N) and ethyl acetate. The organic layer was separated, dried over sodium sulfate and concentrated to provide the product as a mixture of A and B (8 mg, 89% yield). MS (E+) m/z: 232 (MH+); LC retention time (Method A): 1.43 min.

Preparation 15

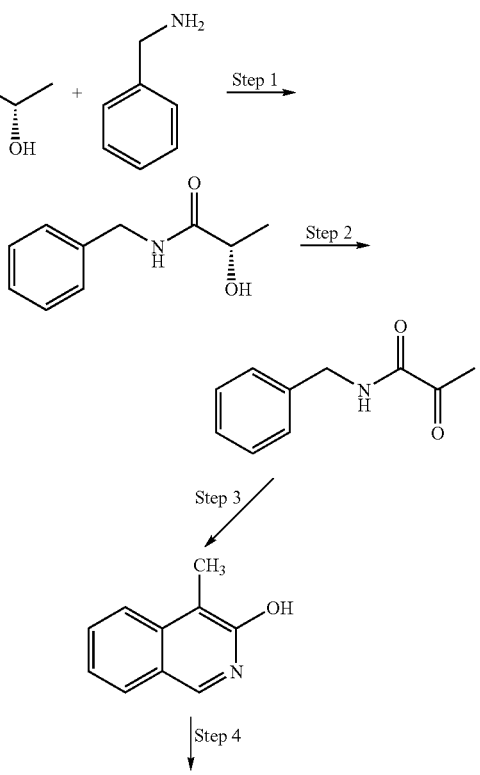

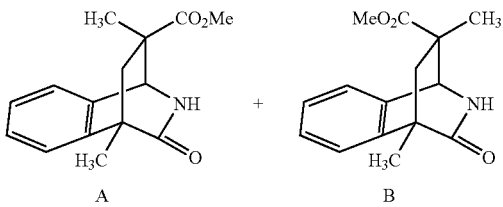

Step 1

A stirred mixture of (S)-methyl lactate (20 g, 192 mmol) and benzylamine (21 mL, 192 mmol) was heated at 130° C. for 1.5 h. At the conclusion of this period, the methanol was removed under reduced pressure to yield a residue. The residue was azeotroped to dryness from toluene to provide the product as an oil (34 g, 99% yield). MS (E+) m/z: 180 (MH+); LC retention time (Method A): 1.53 min (broad).

Step 2

A solution of the product of Step 1 (20.9 g, 117 mmol) in dichloromethane (600 mL) was stirred at room temperature and Dess-Martin periodinane (49.5 g, 117 mmol) was added. Upon completion of addition, the reaction mixture was stirred at room temperature for 30 min and then poured into a stirred aqueous saturated sodium bicarbonate (500 mL) solution. The organic layer was separated, dried over magnesium sulfate and concentrated to provide a residue. The residue was purified by filtration over a plug of silica (30% ethyl acetate in hexanes) to provide the product as an oil (15.1 g, 73% yield). MS (E+) m/z: 178 (MH+); LC retention time (Method A): 1.52 min. $^1$H NMR (CDCl$_3$) δ 7.37-7.23 (m, 5H), 4.47 (d, 2H), 2.52 (s, 3H).

Step 3

The product of Step 2 (8.11 g, 45.8 mmol) was cooled to 0° C. in an ice bath and concentrated sulfuric acid (58 mL) was added dropwise. Upon completion of addition, the ice bath was removed, and the reaction mixture was allowed to warm to room temperature where it stirred for 3 h. After this time, the reaction mixture was slowly poured over ice. The resulting slurry was cooled in an ice bath and rendered basic (pH 10) by the dropwise addition of aqueous ammonium hydroxide (28%). The resulting bright yellow precipitate was collected via filtration with a Buchner funnel, washed with water, and then dried on the pump to provide the title compound (5.58 g, 77% yield).). MS (E+) m/z: 160 (MH+); LC retention time (Method A): 1.81 min.

Step 4

A mixture of the product of Step 3 (656 mg, 4 mmol) and methyl methacrylate (1.32 mL, 12 mmol) in toluene (20 mL) was heated to 170° C. where it stirred for 48 h. At the conclusion of this period, the reaction mixture was cooled to room temperature and concentrated under reduced pressure to provide crude material. A portion (350 mg) of the crude material was purified by preparative HPLC to provide the separated product isomers.

Isomer A (95 mg); MS (E+) m/z: 260 (MH+); LC retention time (Method A): 2.77 min.

Isomer B (54 mg); MS (E+) m/z: 260 (MH+); LC retention time (Method A): 2.53 min.

Preparation 16

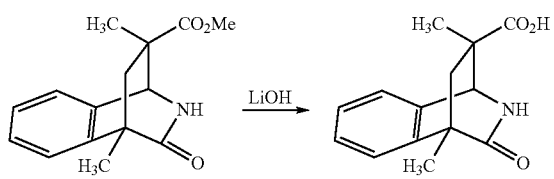

To a stirred mixture of Isomer A of Preparation 15 (25 mg, 0.1 mmol) in THF (2.5 mL) and water (2.5 mL) was added 1N aqueous LiOH (1 mL). Upon completion of addition, the reaction mixture was stirred at room temperature for 18 h. At the conclusion of this period, the reaction mixture was concentrated in vacuo to provide an aqueous mixture. The aqueous mixture was acidified with 1 N HCl and extracted with ethyl acetate (3×5 mL). The combined organic extracts were dried over sodium sulfate and concentrated in vacuo to provide the title compound as a white solid (22 mg, 90% yield). MS (E+) m/z: 246 (MH+); LC retention time (Method A): 2.62 min.

The above procedure was used to prepare the following carboxylic acid using Isomer B of Preparation 15.

| Preparation | Structure |
|---|---|
| 17 | ![structure] |

Preparation 18

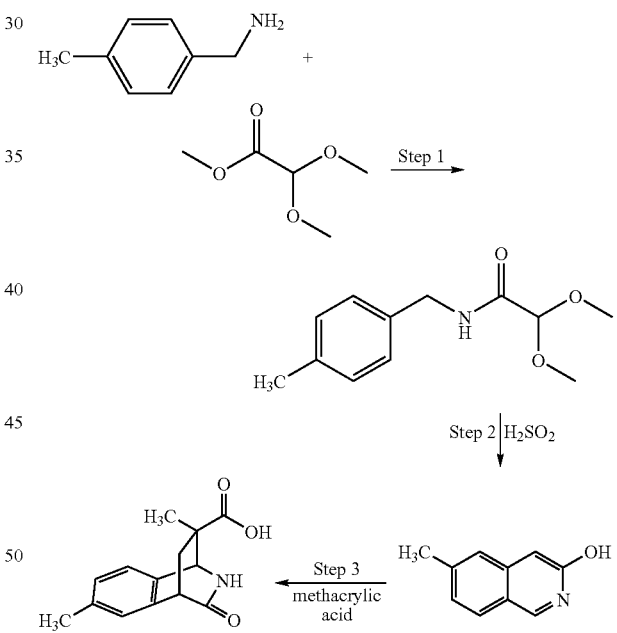

Step 1

Preparation of substituted 3-hydroxy isoquinolines were carried out in the manner described in Fukumi, H.; Kurihara, H.; Heterocycles., 1978, 9(9), 1197-1205. Thus, a mixture of 4-methyl benzylamine (5.54 g, 45.7 mmol) and methyl dimethoxyacetate (6.17 mL, 50.3 mmol) was heated to 130° C. where it stirred for 4 h. After this time, the volatiles were removed under reduced pressure to provide a residue. The residue was azeotroped to dryness from toluene to provide the product, which was used directly in the next step without further purification. MS (E+) m/z: 224 (MH+); LC retention time (Method A): 2.49 min.

Step 2

The neat product of Step 1 was stirred and cooled to 0° C. in an ice bath. Once at the prescribed temperature, concentrated sulfuric acid (26 mL) was added dropwise. Upon completion of addition, the reaction mixture was stirred for 30 min. After this time, the ice bath was removed and the reaction mixture was allowed to warm to room temperature where it stirred for one hour. At the conclusion of this period, the reaction mixture was worked-up and the product isolated in the manner of Step 3, Preparation 15 (4.93 g, 68% yield for two steps). MS (E+) m/z: 160 (MH+); LC retention time (Method A): 1.64 min.

Step 3

The title compound was prepared from the product of step 2 in the manner of Preparation 11. MS (E+) m/z: 246 (MH+); LC retention time (Method A): 2.66 min.

Preparation 19

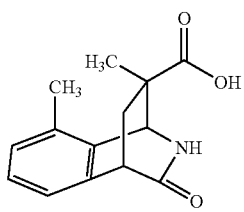

The title compound was prepared in the manner of Preparation 18 using 2-methyl benzyl amine instead of 4-methyl benzyl amine. MS (E+) m/z: 472 (MH+); LC retention time (Method A): 3.93 min.

Preparation 20

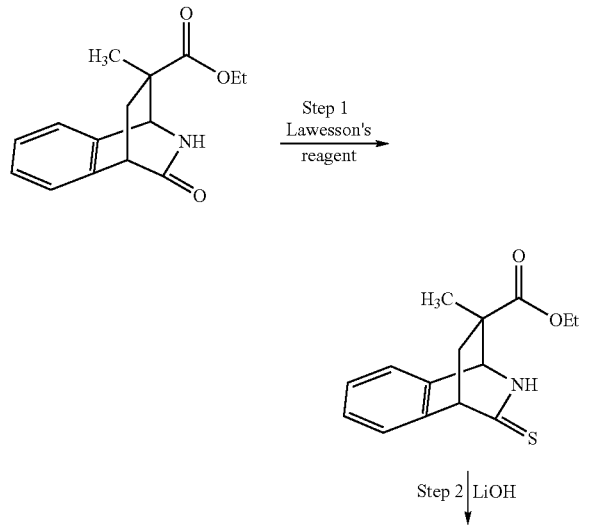

-continued

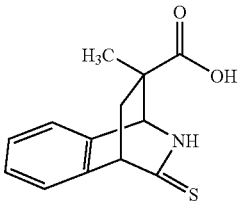

Step 1

A mixture of the product containing isomers C and D of Preparation 13 (665 mg, 2.57 mmol) and Lawesson's reagent (1.14 g, 2.82 mmol) in toluene (25 mL) was heated to 95° C. where it stirred for 1 h. At the conclusion of this period, the reaction mixture was cooled to room temperature, and the crystalline precipitate removed by filtration over celite. The filtrate was concentrated to yield a crude residue. The crude residue was adsorbed on silica and purified by flash column chromatography on silica gel (30% ethyl acetate in hexanes) to provide the title compound as a solid (702 mg, 99%). MS (E+) m/z: 276 (MH+); LC retention time (Method A): 2.88 min.

Step 2

A mixture of the product of Step 1 (170 mg, 0.66 mmol) and lithium hydroxide monohydrate (165 mg, 3.94 mmol) in THF (3 mL), water (1 mL) and methanol (1 mL) was heated to 80° C. where it stirred for 7 h. After this time, the reaction mixture was partitioned between dichloromethane and 1N aqueous sodium hydroxide. The aqueous layer was acidified with the dropwise addition of concentrated HCl and then washed with ethyl acetate. The organic layer was separated, dried over sodium sulfate and concentrated to provide the title compound as a solid (154 mg, 94% yield). MS (E+) m/z: 248 (MH+); LC retention time (Method A): 2.51 min.

Preparation 21

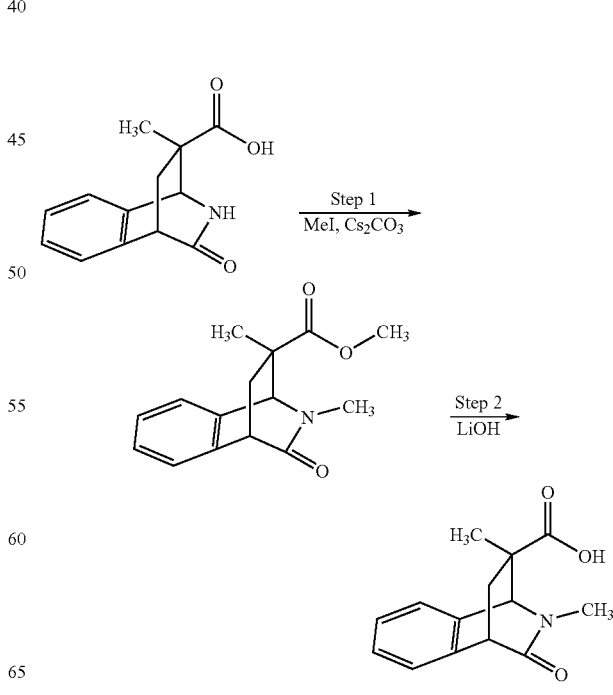

Step 1

A mixture of the carboxylic acid of Preparation 11 (50 mg, 0.216 mmol), iodomethane (0.054 mL, 0.86 mmol), and cesium carbonate (350 mg, 1.08 mmol) in acetone (1.5 mL) was heated to 60° C. where it stirred for 6 h. At the conclusion of this period, the reaction mixture was partitioned between ethyl acetate and 1 N HCl. The organic layer was separated, washed with a saturated aqueous sodium bicarbonate solution and brine, dried over sodium sulfate, and concentrated to provide the product as a solid (53 mg, 95% yield). MS (E+) m/z: 260 (MH$^+$); LC retention time (Method A): 2.53 min.

Step 2

A solution of the title compound of Step 1 (53 mg, 0.20 mmol) in THF (1 mL) and aqueous lithium hydroxide (1.0 M, 1 mL) was stirred at room temperature for 6.5 h. After this time, the reaction mixture was concentrated in vacuo to remove the THF, and the resulting aqueous mixture was partitioned between ethyl acetate and 1 N HCl. The organic layer was separated, washed with brine, dried over sodium sulfate, and then concentrated under reduced pressure to provide the title compound as a solid (46 mg, 94% yield). MS (E+) m/z: 246 (MH$^+$); LC retention time (Method A): 2.39 min.

The following compounds were prepared following the two steps described above for the title compound of Preparation 21.

| Preparation | Structure |
|---|---|
| 22 | 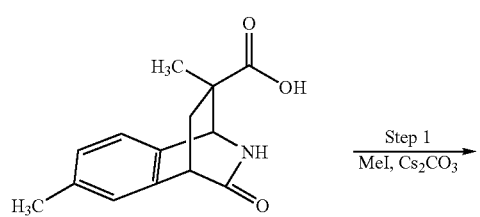 |
| 23 | 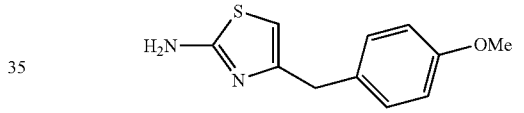 |

Preparation 24

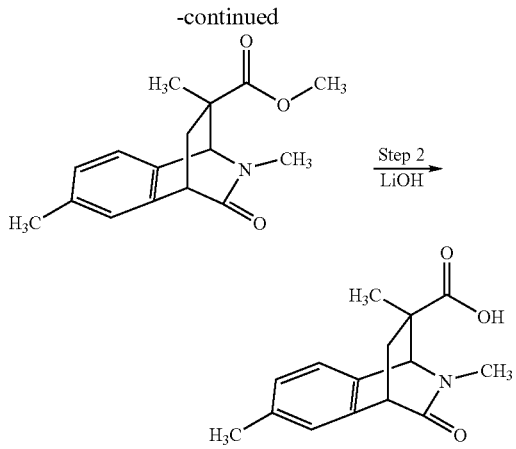

The title compound was prepared in the manner of Preparation 21 using the carboxylic acid product of Preparation 18 instead of the carboxylic acid product of Preparation 11. MS (E+) m/z: 260 (MH$^+$); LC retention time (Method A): 2.79 min.

Preparation 25

(a) Applying the method of Mazzocchi et al (*Synth. Commun.* 1986, 309-312) a cuprate was prepared from 4-methoxyphenylmagnesium bromide (20 mmol, 40 mL of 0.5 M THF solution) and CuBr (574 mg, 2.0 mmol) in 50 mL anhydrous ether. The cuprate was treated with epichlorohydrin (1.94 g, 21 mmol) and stirred at −40 C for 20 hr. The reaction was quenched with water, extracted 2×Et$_2$O, and the ethereal extracts were dried over MgSO$_4$. The solution was filtered, concentrated by rotary evaporator, and chromatographed on SiO$_2$ using 25% EtOAc in hexanes to give 888 mg (22%) of the chlorohydrin 25a as a yellow oil. $^1$H-NMR (400 MHz, CDCl$_3$): δ 7.18 (d, 2H), 6.88 (d, 2H), 4.0 (m, 1H), 3.82 (s, 3H), 3.65 (dd, 1H), 3.52 (dd, 1H), 2.83 (d, 2H).

(b) The intermediate alcohol 25a (888 mg, 4.44 mmol) was taken up in dichloromethane (40 mL) and treated with Dess-Martin periodinane (1.88 g, 4.44 mmol). The reaction was allowed to warm to rt and was complete by TLC monitoring after 4 hr. The reaction mixture was concentrated by rotary evaporation and the crude residue was purified on SiO$_2$ (dichloromethane as eluent) to give 762 mg (86% Y) of chloromethylketone 25b.

(c) This intermediate was taken up in 15 mL of EtOH and treated with a solution of thiourea (302 mg, 3.82 mmol) in 5 mL EtOH. The reaction was concentrated in vacuo and a solid formed on standing to give pure 25c, 208 mg (80%) as a yellow solid. MS found: (M+H)⁺=221.

Preparation 26

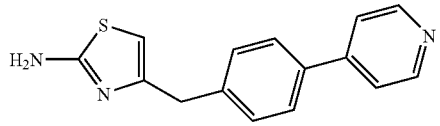

(a) To a solution of commercially available 4-bromophenylacetone (25 g, 117 mmol) in 30 mL of acetic acid and 15 mL of 48% HBr was added a solution of bromine (40 g, 217 mmol) in 50 mL of acetic acid. After 4 hr, acetone (150 mL) was added and the reaction mixture was stirred for 3 d. The reaction was concentrated by rotary evaporator, diluted with brine, and extracted 2×DCM. The DCM extracts were dried over MgSO$_4$. The solution was filtered, concentrated by rotary evaporator, and chromatographed on SiO$_2$ using DCM to give 20.8 g (98%) of a dark oil 26a. $^1$H-NMR (400 MHz, CDCl$_3$): δ 7.49 (d, 2H), 7.12 (d, 2H), 3.94 (s, 2H), 3.92 (s, 2H).

(b) To a solution of 26a (116 mmol) in 200 mL of EtOH was added thiourea (9.0 g, 118 mmol) all at once. The reaction was heated at reflux for 4 hr. The reaction was concentrated by rotary evaporator and the crude residue was dissolved in EtOAc and extracted 3×1N HCl. The aqueous extracts were basified with 1N NaOH and then extracted 2×EtOAC. EtOAc extracts were dried over MgSO$_4$, and solid was triturated in 10% hexanes in EtOAc. Solid was collected and dried in vacuo to give 18 g (57%) of pure 26b. MS found: (M+H)⁺=270.

(c) Charged a flask with 26b (8.07 g, 30 mmol), 4-pyridineboronic acid (6.1 g, 50 mmol), tetrakis(triphenylphosphine)palladium(0) (3.5 g, 3.0 mmol), 30 mL of 2M K$_2$CO$_3$, and 200 mL of DMF. The reaction mixture was degassed by bubbling nitrogen through for 15 min then heated at 100 C overnight. The reaction mixture was diluted in EtOAc and extracted 3×1N HCl. The aqueous extracts were basified with 1N NaOH and then allowed to stand in refrigerator for 2 hr. Solid was collected and dried in vacuo to give 5.4 g (68%) of pure 26c. MS found: (M+H)⁺=268.

Preparation 27

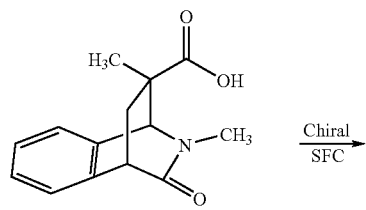

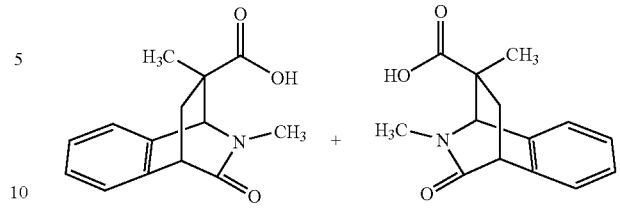

The racemic carboxylic acid product of Preparation 21 (160 mg) was separated by chiral supercritical fluid chromatography (SFC) [OD-H column (3×25 cm), CO$_2$:EtOH:TFA (85:15:0.1) as eluent, 60 mL/min, observed at 220 nm].

Enantiomer A eluted between 5.7 min and 7.0 min, while Enantiomer B eluted between 7.8 min and 9.6 min.

Enantiomer A (68 mg); LC retention time (Method A): 2.37 min.

Enantiomer B (65 mg); LC retention time (Method A): 2.37 min.

Preparation 28

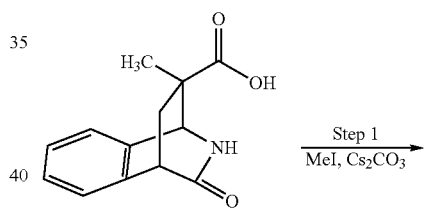

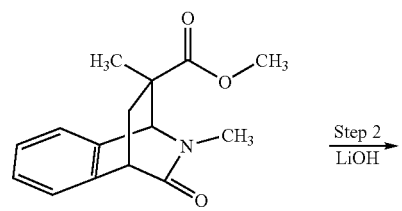

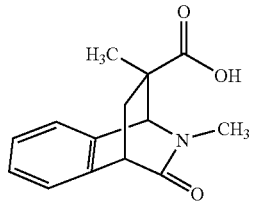

Enantiomer B of Preparation 12 was subjected to the same 2-step procedure described for the preparation of the racemic product of Preparation 21 to give the product acid as a single enantiomer of undetermined absolute stereochemistry. LC retention time (Method A): 2.42 min.

The following Examples illustrate embodiments of the inventive compounds and starting materials, and are not intended to limit the scope of the claims.

EXAMPLE 1

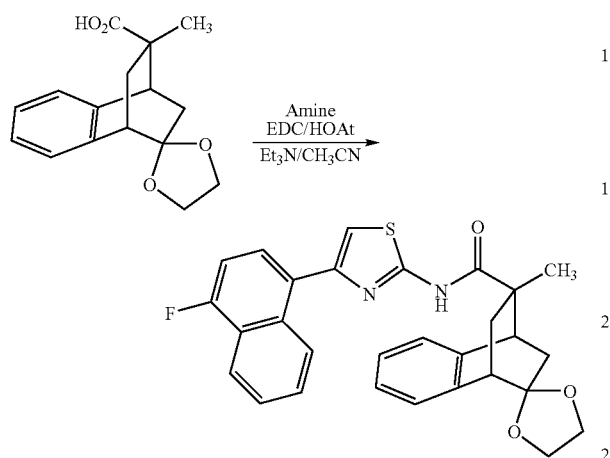

A stirred solution of the acid 1D of Preparation 1 (52 mg, 0.19 mmol), the aminothiazole product of Preparation 4 (56 mg, 0.23 mmol), HOAt (31 mg, 0.23 mmol), EDC (44 mg, 0.23 mmol) and triethylamine (0.066 mL, 0.48 mmol) in acetonitrile (0.6 mL) was heated to 85° C. where it stirred for 5 h. At the conclusion of this period, the reaction mixture was partitioned between ethyl acetate and aqueous HCl (1 N). The organic layer was separated, washed with a saturated aqueous sodium bicarbonate solution and brine, dried over sodium sulfate and concentrated to provide a crude material. The crude material was purified by preparative thin layer chromatography ("TLC", 40% ethyl acetate in hexanes, 200 cm×200 cm, 0.5 mm $SiO_2$) to provide the title compound (20 mg, 21% yield). MS (E+) m/z: 501 (MH$^+$); $^1$H NMR (CDCl$_3$) δ 9.05 (br s, 1H), 8.21 (d, 1H), 8.10 (d, 1H), 7.47-7.53 (m, 3H), 7.05-7.15 (m, 5H), 6.94 (s, 1H), 3.83-3.91 (m, 4H), 2.29-2.36 (m, 2H), 1.94 (dd, 1H), 1.64 (dd, 1H), 1.46 (s, 3H).

EXAMPLE 2

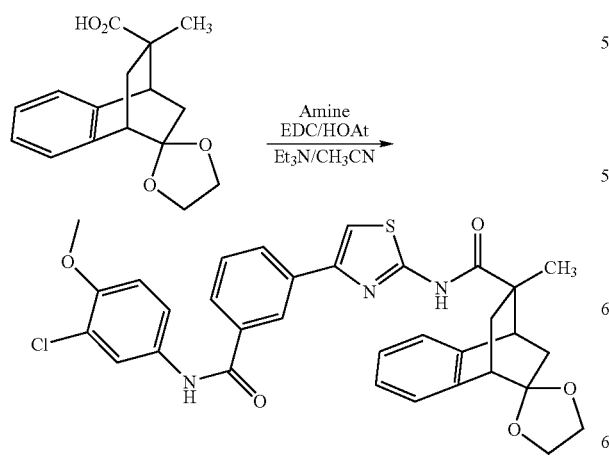

The title compound was prepared in the manner of Example 1 using the carboxylic acid 1D of Preparation 1 and amine of Preparation 9. MS (E+) m/z: 617 (MH$^+$); $^1$H NMR (CD$_3$OD) δ 8.53 (dd, 1H), 8.14 (dd, 1H), 7.89 (m, 2H), 7.63 (dd, 1H), 7.55 (dd, 1H), 7.39 (s, 1H), 7.08-7.18 (m, 5H), 3.90 (s, 3H), 3.80-3.95 (m, 4H), 3.54 (dd, 1H), 3.13 (dd, 1H), 2.57 (dd, 1H), 2.48 (dd, 1H), 1.95 (dd, 1H), 1.73 (dd, 1H), 1.60 (s, 3H).

EXAMPLE 3

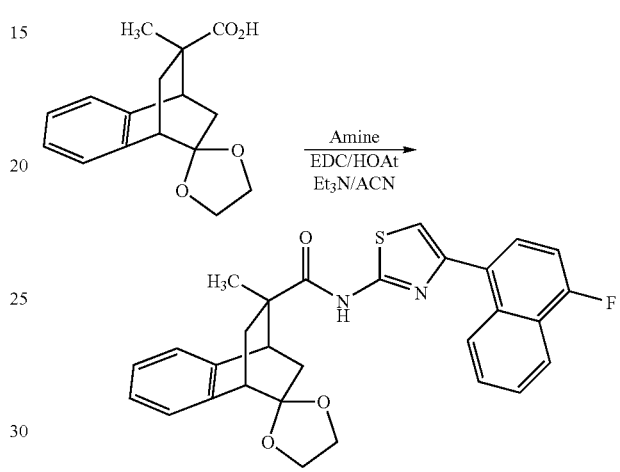

A stirred solution of the acid 1E of Preparation 1 (41 mg, 0.15 mmol), the aminothiazole of Preparation 4 (40 mg, 0.165 mmol), HOAt (24 mg, 0.18 mmol), EDC (35 mg, 0.18 mmol), and triethylamine (0.052 mL, 0.38 mmol) in acetonitrile (0.5 mL) was heated to 85° C. where it stirred for 3.25 h. At the conclusion of this period, the reaction mixture was partitioned between ethyl acetate and aqueous HCl (1 N). The organic layer was separated, washed with a saturated aqueous sodium bicarbonate solution and brine, dried over sodium sulfate and concentrated to provide a crude material. The crude material was purified by preparative TLC (40% ethyl acetate in hexanes, 200 cm×200 cm, 0.5 mm $SiO_2$) to provide the title compound (22 mg, 29% yield). MS (E+) m/z: 501 (MH$^+$); $^1$H NMR (CDCl$_3$) δ 10.07 (s, 1H), 8.28 (d, 1H), 8.11 (d, 1H), 7.45-7.57 (m, 3H), 7.08-7.19 (m, 5H), 7.03 (s, 1H), 3.82-3.95 (m, 4H), 3.20 (dd, 1H), 3.04 (dd, 1H), 2.87 (dd, 1H), 2.19 (dd, 1H), 1.73 (dd, 1H), 1.25 (dd, 1H), 0.91 (s, 3H).

EXAMPLE 4

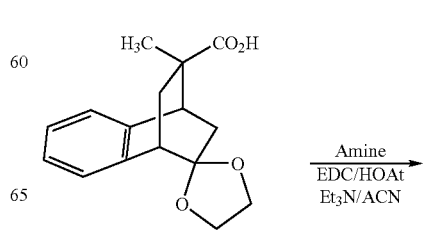

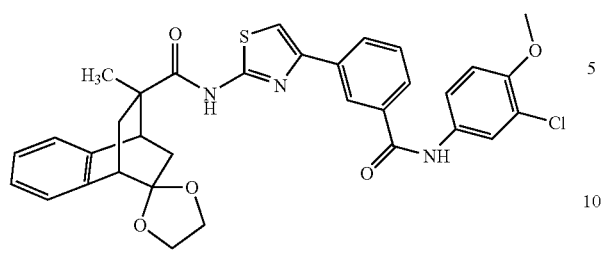

The title compound was prepared in the manner of Example 2 using carboxylic acid 1E of Preparation 1 and the amine product of Preparation 9. MS (E+) m/z: 617 (MH+); LC retention time (Method B): 2.21 min.

EXAMPLE 5

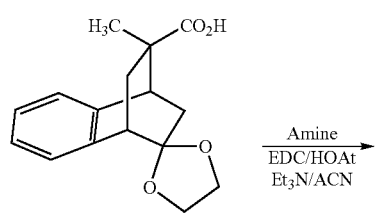

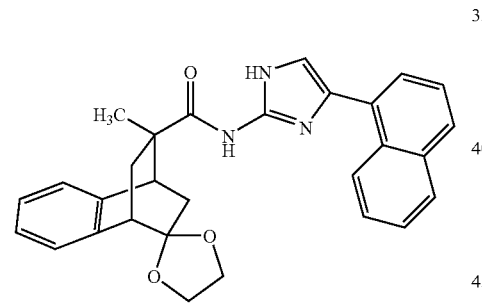

The title compound was prepared in the manner of Example 3 as a single enantiomer using the homochiral carboxylic acid Enantiomer A of Preparation 2 and the amine of Preparation 6. MS (E+) m/z: 466 (MH+); LC retention time (Method B): 1.73 min.

EXAMPLE 6

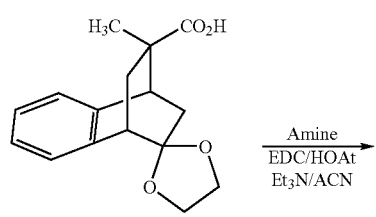

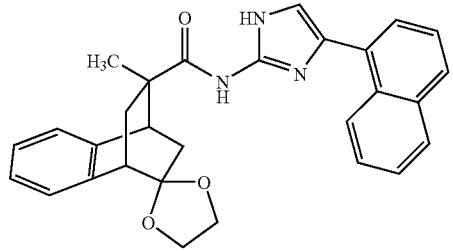

The title compound was prepared in the manner of Example 3 as a single enantiomer using the homochiral carboxylic acid Enantiomer B of Preparation 2 and the amine product of Preparation 6. MS (E+) m/z: 466 (MH+); LC retention time (Method B): 1.73 min.

EXAMPLE 7

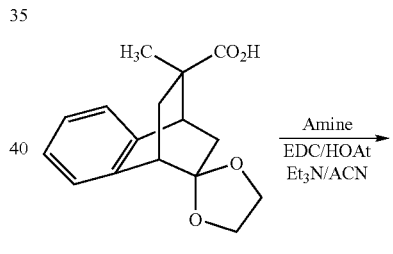

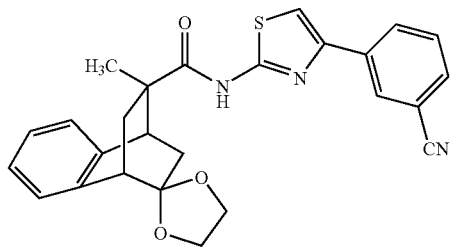

The title compound was prepared in the manner of Example 3 using the carboxylic acid 1E of Preparation 1 and the product from Step 1 of Preparation 9. MS (E+) m/z: 458 (MH+); LC retention time (Method B): 1.88 min.

EXAMPLE 8

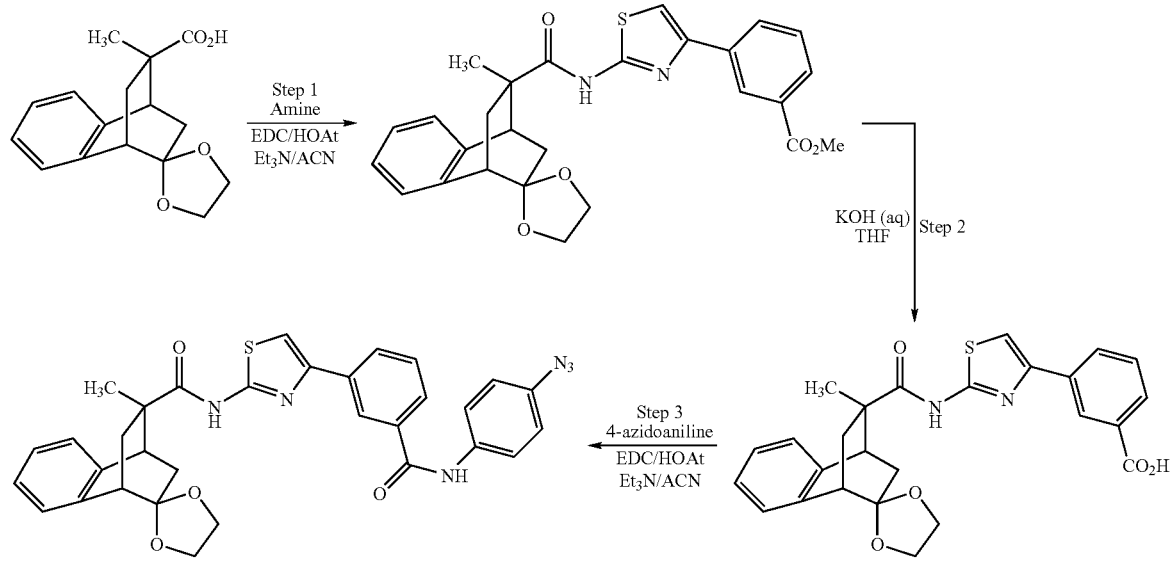

Step 1

The title compound was prepared in the manner of Example 3 using the carboxylic acid 1E of Preparation 1 and the product of Preparation 10. MS (E+) m/z: 491 (MH+); LC retention time (2 min grad.): 1.96 min.

Step 2

A solution of the product of Step 1 (37 mg, 0.076 mmol) in a mixture of THF and 1N aqueous KOH (1:1, 1 mL) was stirred at room temperature for 5 h. At the conclusion of this period, the reaction mixture was acidified with the dropwise addition of 1N HCl and washed with ethyl acetate. A white precipitate gradually formed in the organic layer, which was concentrated and dried under high vacuum to provide the title compound as a solid (34 mg, 94% yield). MS (ES−) m/z: 475 (M−H); LC retention time (Method B): 2.03 min.

Step 3

A solution of the product of Step 2 (17 mg, 0.036 mmol), EDC (8.6 mg, 0.045 mmol), HOAt (6.0 mg, 0.045 mmol), triethylamine (0.012 mL, 0.09 mmol) and 4-azidoaniline hydrochloride (8.0 mg, 0.045 mmol) was stirred at room temperature for 16 h. At the conclusion of this period, the reaction mixture was partitioned between ethyl acetate and 1N HCl. The organic layer was separated, washed with a saturated aqueous sodium bicarbonate solution and brine, dried over sodium sulfate, and concentrated to yield a residue. The residue was purified by preparative thin layer chromatography on silica (20 cm×20 cm, 40% ethyl acetate in hexanes) to provide the product as a solid (18 mg, 84% yield). MS (E+) m/z: 593 (M+H); LC retention time (Method A): 4.13 min. $^1$H NMR (CD$_3$OD) δ 8.49 (dd, 1H), 8.12 (dd, 1H), 7.83 (dd, 1H), 7.70 (d, 2H), 7.47-7.49 (m, 2H), 7.15-7.20 (m, 4H), 7.04 (d, 2H), 3.83-3.94 (m, 4H), 3.38 (dd, 1H), 3.03 (dd, 1H), 2.99 (dd, 1H), 2.08 (dd, 1H), 1.64 (dd, 1H), 1.15 (dd, 1H), 0.82 (s, 3H).

EXAMPLE 9

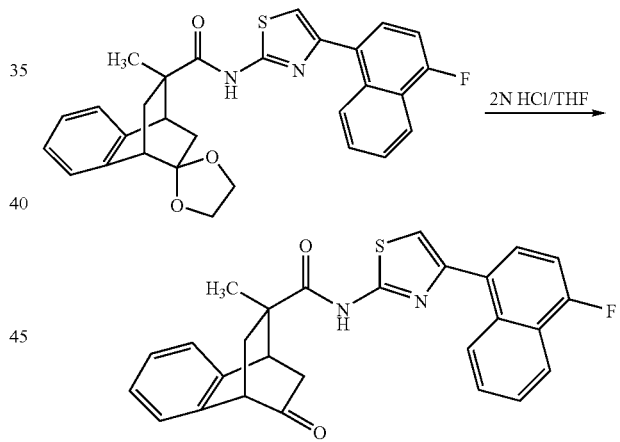

A mixture of the title compound of Example 3 (17 mg, 0.037 mmol) in a mixture of THF (0.3 mL) and aqueous HCl (2 N, 0.35 mL) was heated to 60° C. where it stirred for 8 h. At the conclusion of this period, the reaction mixture was partitioned between ethyl acetate and brine. The organic layer was separated, dried over sodium sulfate, and concentrated to provide a crude residue. The crude residue was purified by preparative TLC (100 cm×200 cm, 0.5 mm silica, 40% ethyl acetate in hexanes) to provide the title product as an oil (5 mg, 30% yield). MS (E+) m/z: 457 (M+H); LC retention time (Method A): 4.13 min. $^1$H NMR (CDCl$_3$) δ 8.20 (dd, 2H), 8.15 (dd, 1H), 7.55-7.48 (m, 3H), 7.24-7.13 (m, 5H), 7.07 (s, 1H), 3.60 (dd, 1H), 3.47 (dd, 1H), 3.07 (dd, 1H), 2.45 (dd, 1H), 2.09 (dd, 1H), 1.51 (dd, 1H), 1.02 (s, 3H).

The following examples (10-15) were prepared in the manner of Example 9 using the title compounds of Examples 4, 8, 1, 2, 5, and 6, respectively.
| Ex. # | Structure | Rt (min) | M/z (MH)+ |
|---|---|---|---|
| *10 | 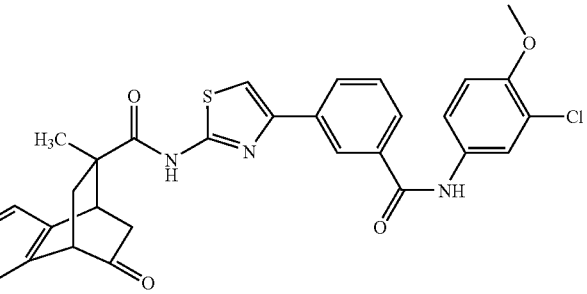 | 4.01 | 573 |
| *11 | 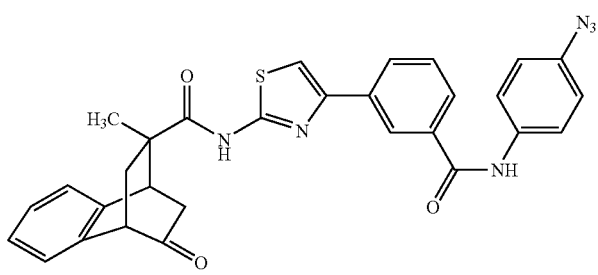 | 4.08 | 549 |
| *12 | 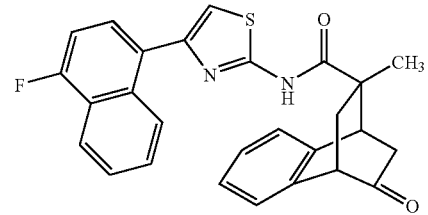 | 3.98 | 457 |
| *13 | 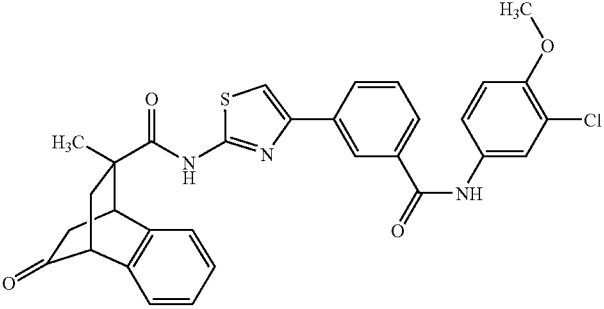 | 3.79 | 573 |
| **14 | 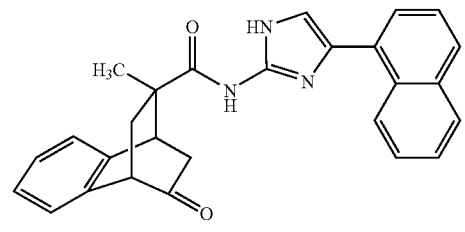  homochiral | 1.72 | 422 |

-continued

| Ex. # | Structure | Rt (min) | M/z (MH)+ |
|---|---|---|---|
| **15 | homochiral | 1.72 | 422 |

"*"analyzed by Analytical LC Method A
"**"analyzed by Analytical LC Method B

EXAMPLE 16

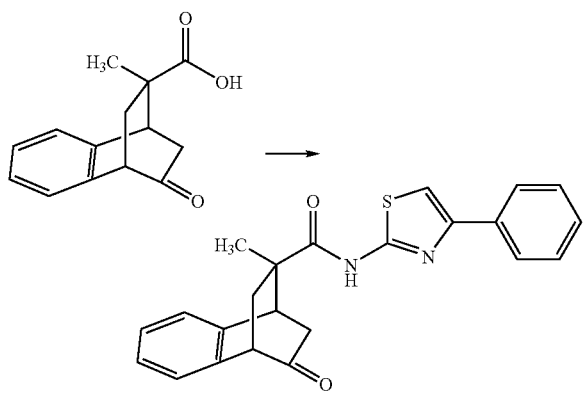

A mixture of the carboxylic acid of Preparation 3 (15 mg, 0.06 mmol), triethylamine (0.023 mL, 0.16 mmol), HOAt (11 mg, 0.08 mmol), EDC (15 mg, 0.08 mmol) and 4-phenyl-thiazol-2-ylamine (14 mg, 0.08 mmol) in acetonitrile (1 mL) was heated to 80° C. where it stirred for 3 h. After this time, the reaction mixture was purified by reverse phase preparative HPLC to provide the product (16 mg, 69% yield). MS(E+) m/z: 389 (M+H); LC retention time (Method A): 4.31 min.

The following examples 17-25 were prepared in the manner of Example 16, including analysis by Analytical LC Method A, using commercially available amines.

| Ex. # | Structure | Rt (min) | M/z (MH)+ |
|---|---|---|---|
| 17 | 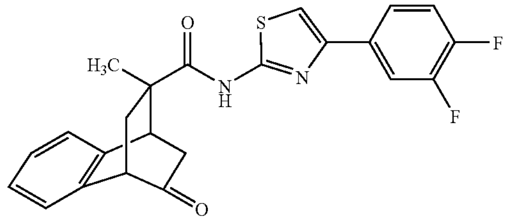 | 4.34 | 525 |
| 18 | 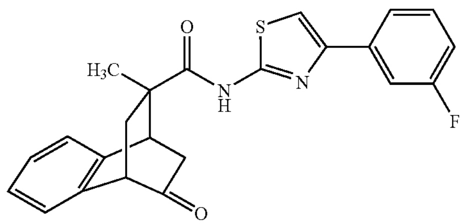 | 4.37 | 407 |

-continued
| Ex. # | Structure | Rt (min) | M/z (MH)+ |
|---|---|---|---|
| 19 | 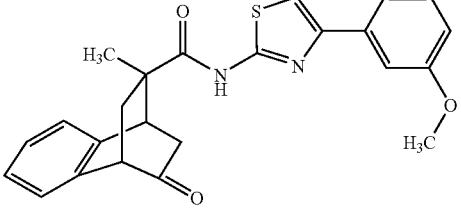 | 4.34 | 419 |
| 20 | 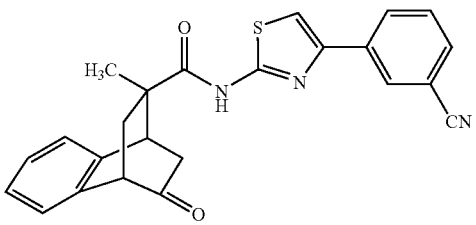 | 4.18 | 414 |
| 21 | 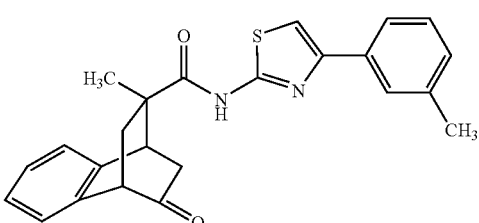 | 4.41 | 403 |
| 22 | 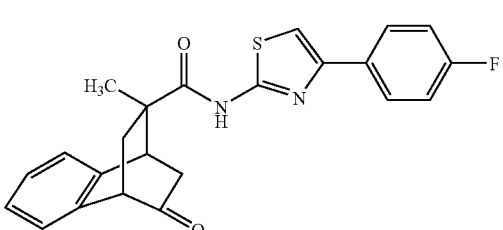 | 4.34 | 407 |
| 23 | 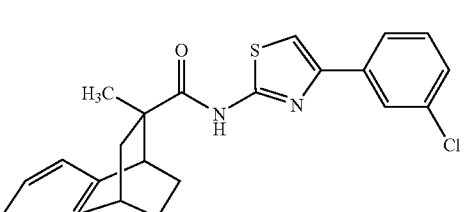 | 4.56 | 424 |
| 24 | 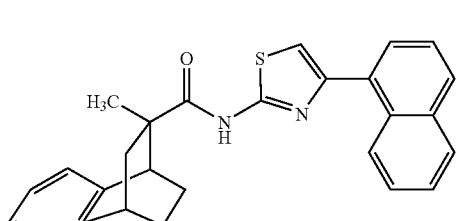 | 4.57 | 439 |

-continued

| Ex. # | Structure | Rt (min) | M/z (MH)+ |
|---|---|---|---|
| 25 | 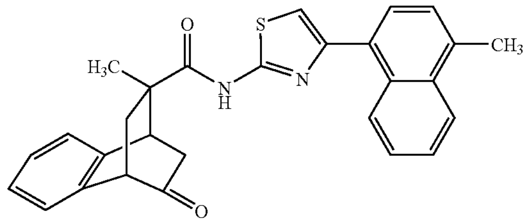 | 4.72 | 453 |

EXAMPLE 26

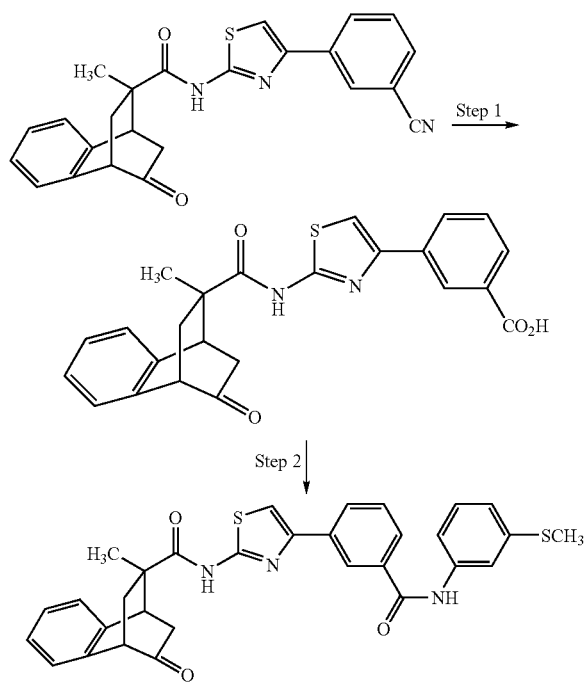

Step 1

A suspension of the title compound of Example 20 (110 mg, 0.27 mmol) in 3 N HCl was heated to 170° C. in a Personal Chemistry™ microwave reactor system and held for 20 min. At the conclusion of this period, the reaction mixture was cooled to room temperature, and then diluted with ethyl acetate. The organic layer was separated, washed with water, dried over sodium sulfate, and concentrated to provide the title compound as a solid (112 mg, 97%). MS (E+) m/z: 433 (M+H); LC retention time (Method A): 3.34 min.

Step 2

The title compound was prepared following the procedure described for the preparation of the title compound of Example 16 using the product of Step 1 and m-thiomethyl aniline. MS (E+) m/z: 554 (M+H); LC retention time (Method A): 4.54 min.

The following examples 27-33 were prepared in the manner of Step 2, Example 26, including analysis by Analytical LC Method A, using the product of Step 1 of Example 26 and commercially available amines.

| Ex. # | Structure | Rt (min) | M/z (MH)+ |
|---|---|---|---|
| 27 | 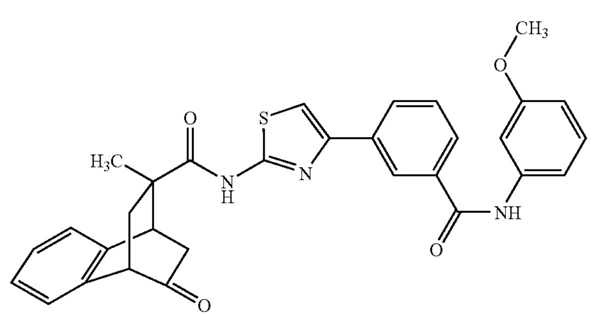 | 4.54 | 538 |

-continued
| Ex. # | Structure | Rt (min) | M/z (MH)+ |
|---|---|---|---|
| 28 | 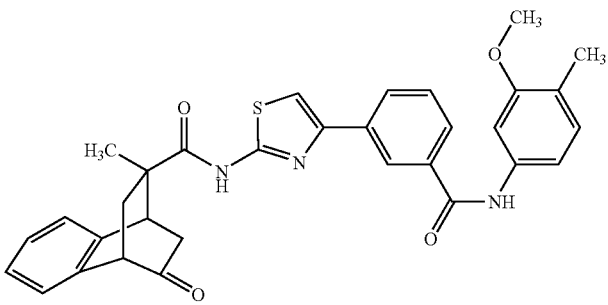 | 4.55 | 552 |
| 29 | 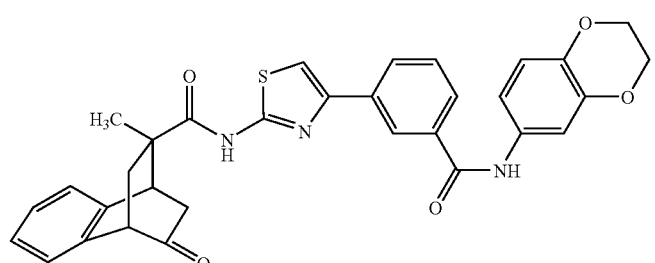 | 4.19 | 566 |
| 30 | 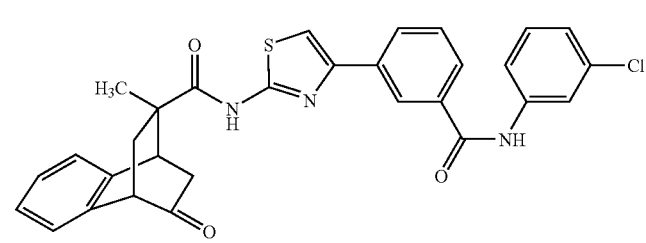 | 4.58 | 543 |
| 31 | 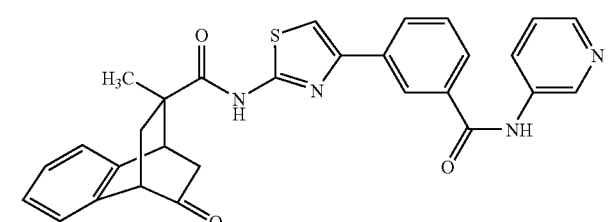 | 3.68 | 509 |
| 32 | 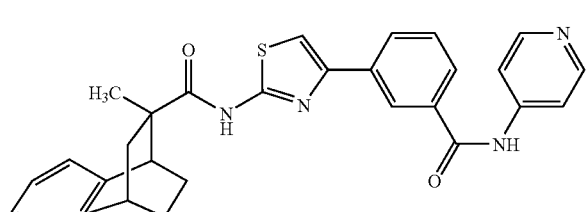 | 3.50 | 509 |
| 33 | 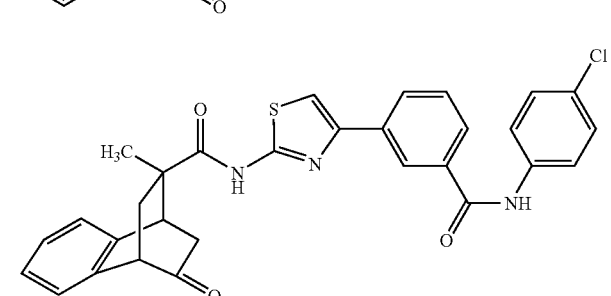 | 4.56 | 543 |

EXAMPLE 34

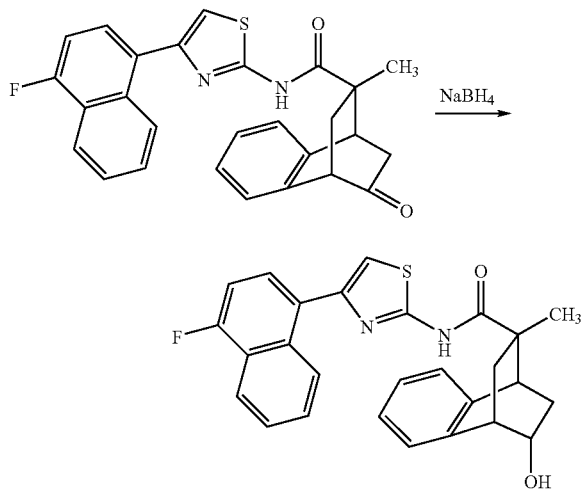

A stirred solution of the product of Example 12 (13 mg, 0.029 mmol) in methanol (0.5 mL) was cooled to 0° C. and sodium borohydride (3.3 mg, 0.09 mmol) was added. Upon completion of addition, the solution was stirred at 0° C. for 20 min and then concentrated to provide a residue. The residue was taken up in 1 mL 1 N HCl, and the resulting mixture was washed with ethyl acetate. The organic layer was separated, washed with a saturated sodium bicarbonate solution and brine, dried over sodium sulfate, and concentrated to provide a residue. The residue was purified by preparative TLC on silica (0.5 mm, 200×200 cm, 40% ethyl acetate in hexanes). The top eluting band was collected to provide the title compound (3.7 mg, 30%). MS (E+) m/z: 459 (M+H); LC retention time (Method A): 3.96 min.

EXAMPLE 35

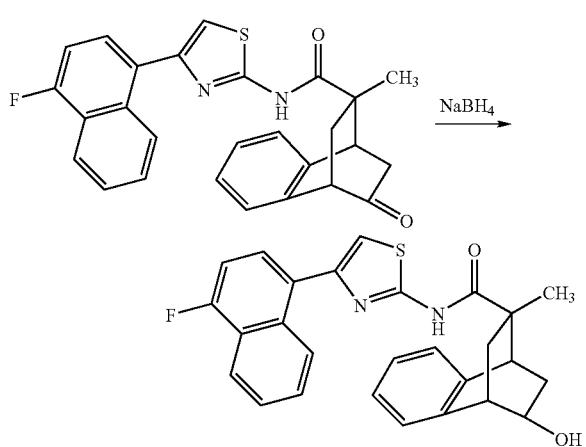

The bottom eluting band of the preparative TLC obtained during the purification of the title compound of example 34 was collected to provide the title compound (6.10 mg, 46%). MS (E+) m/z: 459 (M+H); LC retention time (Method A): 3.88 min.

EXAMPLE 36

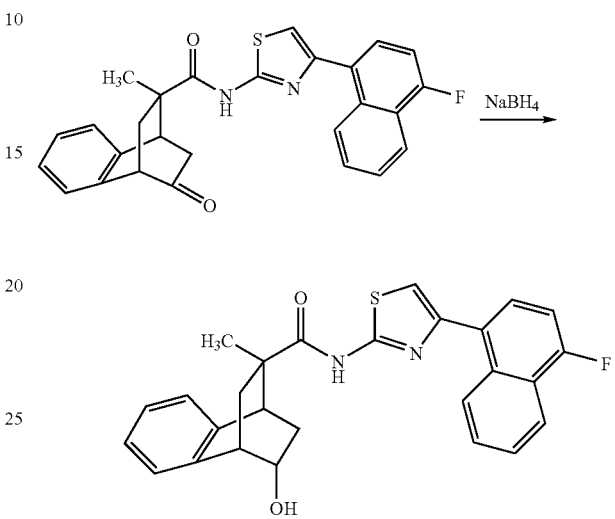

This compound was prepared in the manner of Example 34 using the product of Example 9 (16 mg, 0.029 mmol), methanol (0.5 mL) and sodium borohydride (4 mg, 0.11 mmol). Similar to Example 34, the top eluting band of the preparative TLC obtained during purification of the crude material was collected to provide the title compound (2.7 mg, 20%). MS (E+) m/z: 459 (M+H); LC retention time (Method A): 4.11 min.

EXAMPLE 37

Similar to Example 35, the bottom eluting band of the preparative TLC obtained during the purification of the title compound of Example 36 was collected to provide the title compound (5.0 mg, 38%). MS (E+) m/z: 459 (M+H); LC retention time (Method A): 4.16 min.

EXAMPLE 38

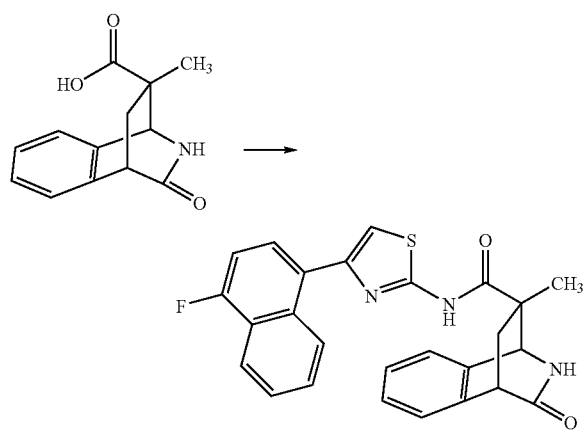

A mixture of the carboxylic acids of Preparation 14 (8 mg, 0.035 mmol, triethylamine (0.012 mL, 0.088 mmol), 1-hydroxybenzotriazole ("HOBt") monohydrate (5.7 mg, 0.042 mmol), EDC (8 mg, 0.042 mmol), and the amine of Preparation 4 (9.5 mg, 0.039 mmol) in DMF (0.35 mL) was heated to 80° C. where it stirred for 10 min. At the conclusion of this period, the reaction mixture was partitioned between ethyl acetate and 1 N HCl. The organic layer was separated, washed with a saturated aqueous sodium bicarbonate solution and brine, and then dried over sodium sulfate to provide crude product. The crude product was purified by preparative TLC on silica (200 cm×200 cm, 0.5 mm silica, 5% methanol/dichloromethane) to provide the title compound as a solid (3.0 mg, 20%). MS (E+) m/z: 458 (M+H); LC retention time (Method A): 3.84 min.

EXAMPLE 39

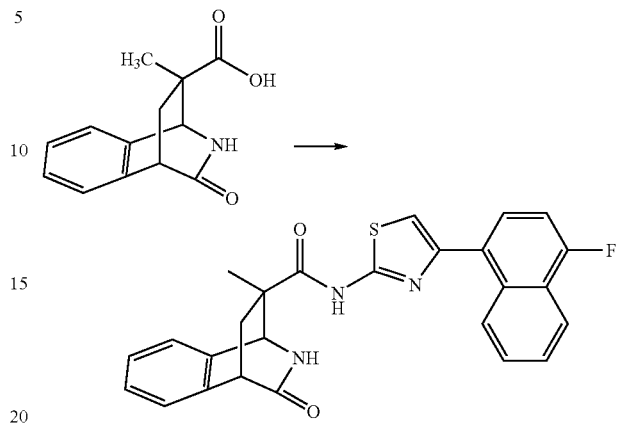

A mixture of the carboxylic acid of Preparation 11 (112 mg, 0.48 mmol), triethylamine (0.17 mL, 1.2 mmol), HOBt monohydrate (78 mg, 0.58 mmol), EDC (111 mg, 0.58 mmol), and the amine of Preparation 4 (129 mg, 0.53 mmol) in DMF (3 mL) was heated to 70° C. where it stirred for 1.5 h. After this time, the reaction mixture was partitioned between ethyl acetate and 1N aqueous HCl. The organic layer was washed sequentially with a saturated aqueous sodium bicarbonate solution and brine, dried over sodium sulfate, and concentrated to provide a residue. The residue was purified by flash column chromatography on silica (50% ethyl acetate in hexanes to 60% ethyl acetate in hexanes) to provide the title compound as a tan-colored solid (80 mg, 37% yield). MS (E+) m/z: 458 (M+H); LC retention time (Method A): 3.81 min.

The following examples 40-46 were prepared in the manner of Example 38 using the carboxylic acids of Preparations 17, 16, and 11, amines of Preparations 4, 7, and 25, and commercially available 4-(naphthalen-1-yl)thiazol-2-amine.

| Ex. # | Structure | Rt (min) | M/z (MH)+ |
|---|---|---|---|
| *40 | 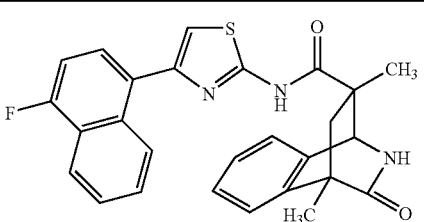 | 3.99 | 472 |
| *41 | 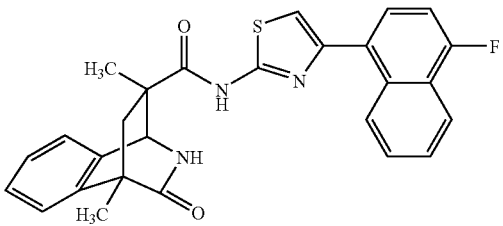 | 3.98 | 472 |

-continued
| Ex. # | Structure | Rt (min) | M/z (MH)+ |
|---|---|---|---|
| *42 | 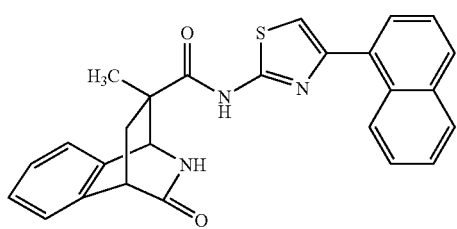 | 3.68 | 440 |
| *43 | 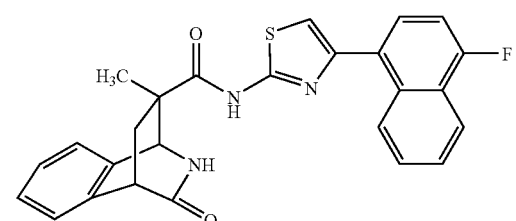 homochiral | 3.80 | 458 |
| *44 | 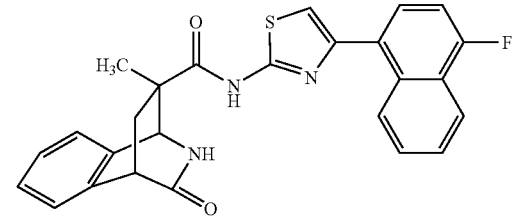 homochiral | 3.80 | 458 |
| 45 | 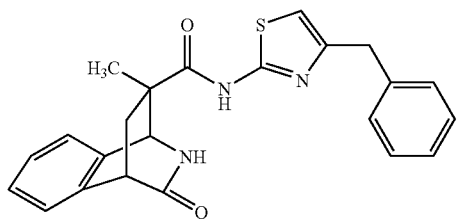 | | 404 |
| *46 | 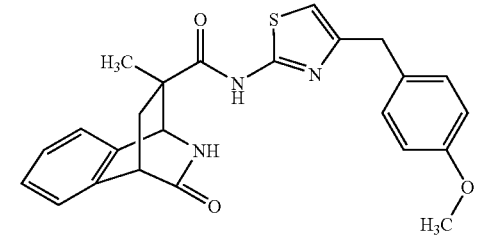 | 3.31 | 434 |
"*"analyzed by Analytical LC Method A

EXAMPLE 47

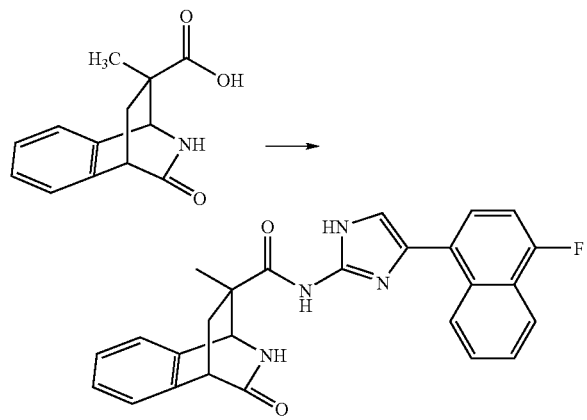

A mixture of the carboxylic acid of Preparation 11 (30 mg, 0.13 mmol), amine of Preparation 5 (42 mg, 0.16 mmol), benzotriazole-1-yl-oxy-tris-dimethylamino)-phosphonium ("BOP reagent", 88 mg, 0.20 mmol) and diisopropyl ethyl amine (0.11 mL, 0.65 mmol) in DMF (0.26 mL) was heated to 70° C. where it stirred for 15 h. At the conclusion of this period, the reaction mixture was purified by preparative HPLC to provide the product as a white solid (30 mg, 42% yield). MS (E+) m/z: 441 (M+H); LC retention time (Method A): 2.65 min.

The following examples 48-49 were prepared in the manner of Example 46, including analysis by Analytical LC Method A, using the homochiral carboxylic acids, Enantiomers A and B, respectively, of Preparation 12 and amine of Preparation 6.

| Ex. # | Structure | Rt (min) | M/z (MH)+ |
|---|---|---|---|
| 48 | 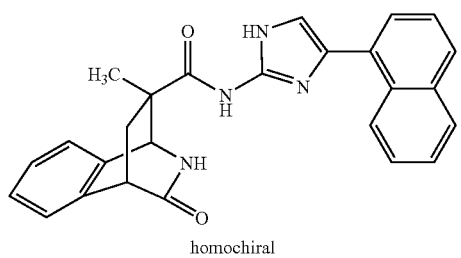<br>homochiral | 2.48 | 423 |
| 49 | 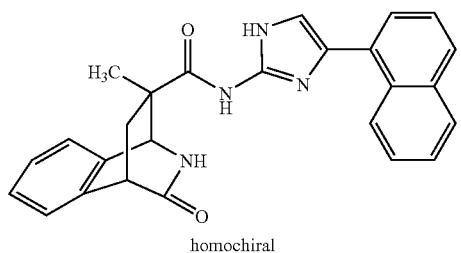<br>homochiral | 2.48 | 423 |

The following Examples 50-51 were prepared in the manner of Example 39, including analysis by Analytical LC Method A, using the carboxylic acids of Preparations 16, Enantiomer B of Preparation 12 and the amine of Preparation 9.

| Ex. # | Structure | Rt (min) | M/z (MH)+ |
|---|---|---|---|
| 50 | 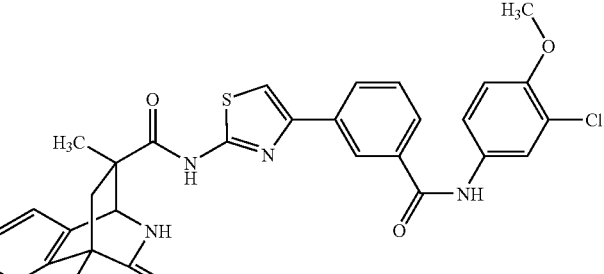 | 3.87 | 588 |
| 51 | 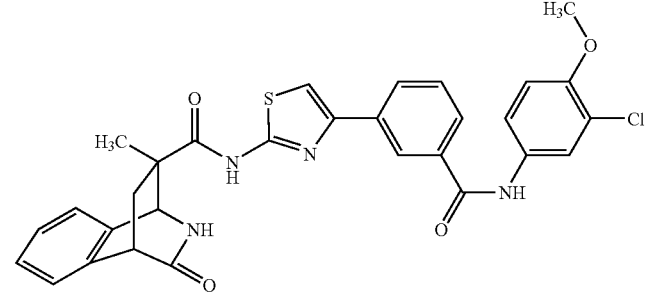 homochiral | 3.68 | 573 |

EXAMPLE 52

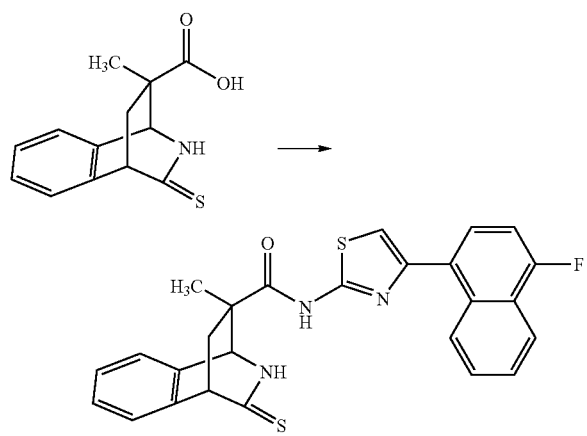

A mixture of the thiolactam product of Preparation 20 (32 mg, 0.13 mmol), triethylamine (0.045 mL, 0.33 mmol), HOAt (21 mg, 0.16 mmol), EDC (31 mg, 0.16 mmol) and the amine of Preparation 5 (167 mg, 0.69 mmol) in acetonitrile (0.5 mL) was heated to 85° C. where it stirred for 1 h. After this time, the reaction mixture was partitioned between ethyl acetate and 1 N aqueous HCl. The organic layer was separated, washed with a saturated aqueous sodium bicarbonate solution and brine, dried over sodium sulfate and concentrated to provide a residue. The residue was purified by preparative TLC on silica (200 cm×200 cm, 0.5 mm, 1:1 ethyl acetate:hexanes). The title compound was obtained as a white solid (18 mg, 29%). MS (E+) m/z: 474 (M+H); LC retention time (Method A): 3.91 min.

The following examples 53-54 were prepared in the manner of Example 52, including analysis by Analytical LC Method A.

| Ex. # | Structure | Rt (min) | M/z (MH)+ |
|---|---|---|---|
| 53 | 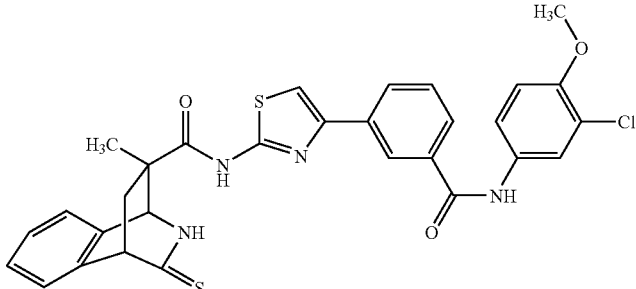 | 3.74 | 589 |
| 54 | 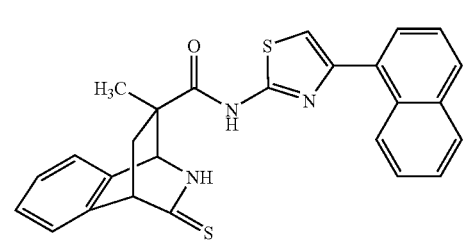 | 3.74 | 456 |

EXAMPLE 55

EXAMPLE 56

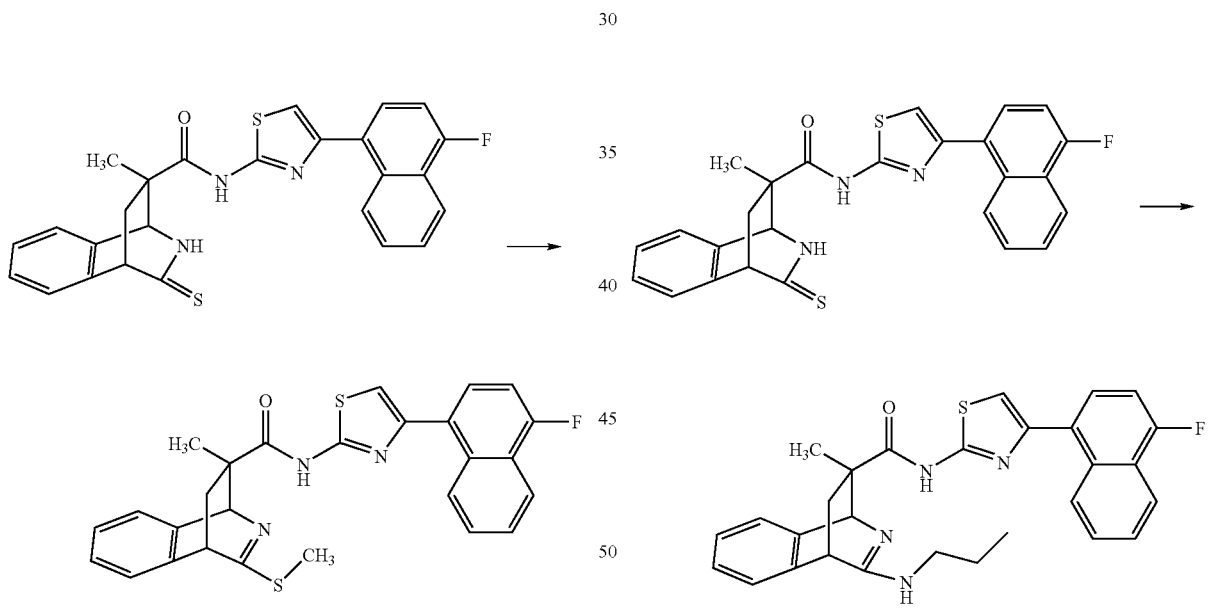

To a stirred solution of the title compound of Example 52 (20 mg, 0.042 mmol) in THF (0.4 mL) was added potassium carbonate (7 mg, 0.05 mmol) followed by methyl iodide (0.008 mL, 0.13 mmol). Upon completion of addition, the reaction mixture was stirred at room temperature for 48 h, and then partitioned between ethyl acetate and 1 N HCl. The organic layer was separated, washed with a saturated aqueous sodium bicarbonate solution and brine, dried over sodium sulfate and concentrated to provide the title compound as a sticky solid (20 mg, 98% yield). MS (E+) m/z: 488 (M+H); LC retention time (Method A): 3.75 min.

A solution of the title compound of Example 52 (7 mg, 0.015 mmol) and n-propylamine (0.006 mL, 0.074 mmol) in THF (0.2 mL) was heated to 55° C. Once at the prescribed temperature, mercuric chloride (5 mg, 0.02 mmol) was added causing a precipitate to be formed immediately. Upon completion of addition, the mixture was stirred at 55° C. for 1 h during which time a black precipitate was formed. At the conclusion of this period, the reaction mixture was filtered through a syringe-tip disposable filter (0.45 um, PTFE) and purified by reverse phase preparative HPLC to provide the product as a colorless oil TFA salt (6.7 mg, 73% yield). MS (E+) m/z: 499 (M+H); LC retention time (Method A): 3.31 min.

EXAMPLE 57

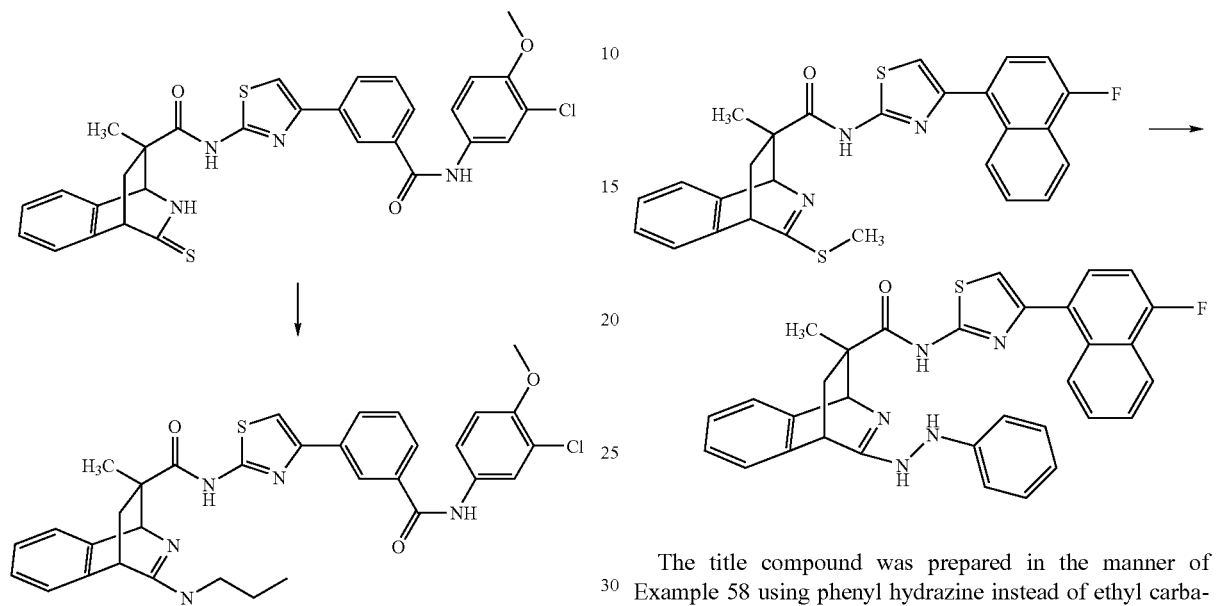

The title compound was prepared in the manner of Example 56 using the title compound of Example 53 instead of the title compound of Example 52. MS (E+) m/z: 625(M+H); LC retention time (Method A): 3.19 min.

EXAMPLE 58

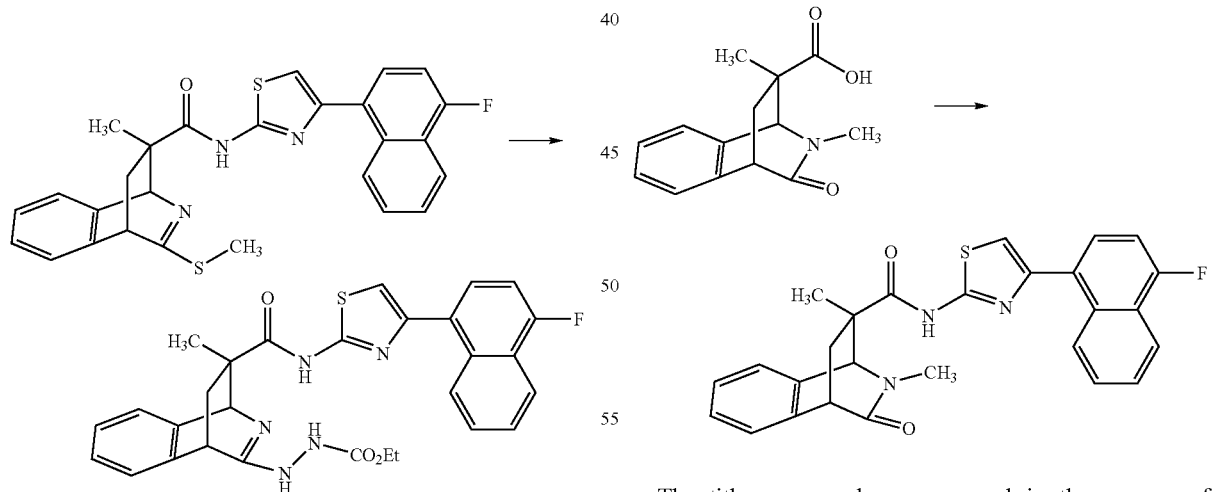

A mixture of the title compound of Example 55 (9 mg, 06018 mmol) and ethyl carbazate (4 mg, 0.036 mmol) in ethanol (0.25 mL) was heated to 80° C. where it stirred for 1 h. At the conclusion of this period, the solvent was removed under a nitrogen stream to provide a residue. The residue partitioned between ethyl acetate and water. The organic layer was separated, dried over sodium sulfate and concentrated to provide a residue. This residue was purified by reverse phase preparative HPLC, and the product was freeze-dried from water/acetonitrile to provide a white amorphous solid TFA salt (6 mg, 51% yield). MS (E+) m/z: 544(M+H); LC retention time (Method A): 3.21 min.

EXAMPLE 59

The title compound was prepared in the manner of Example 58 using phenyl hydrazine instead of ethyl carbazate. MS (E+) m/z: 548 (M+H); LC retention time (Method A): 3.41 min.

EXAMPLE 60

The title compound was prepared in the manner of Example 39 using the carboxylic acid of Preparation 21 and amine of Preparation 4. MS (E+) m/z: 472 (M+H); LC retention time (Method A): 3.95 min.

The following examples 61-66 were prepared in the manner of Example 60, including analysis by Analytical LC Method A, using the carboxylic acids of Preparations 21-23 and Preparation 28 and amines of Preparations 4, 5, 7, 9, 25, and 26.

| Ex. # | Structure | Rt (min) | M/z (MH)+ |
|---|---|---|---|
| 61 | 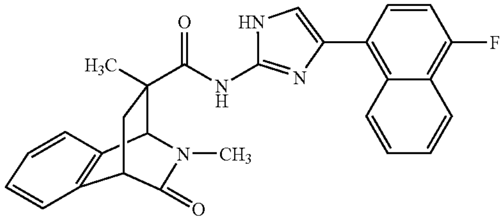 | 2.80 | 455 |
| 62 | 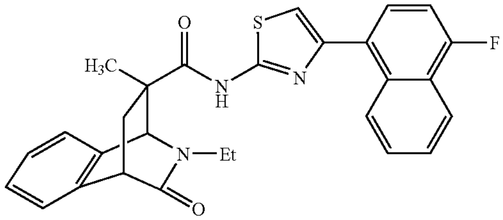 | 4.01 | 486 |
| 63 | 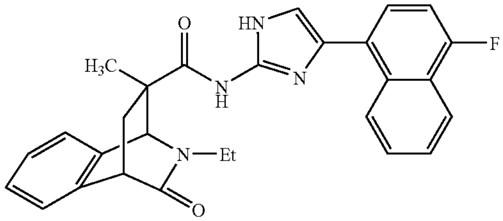 | 2.96 | 469 |
| 64 | 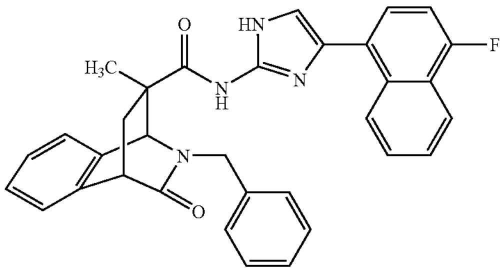 | 3.26 | 531 |
| 65 | homochiral | 3.83 | 587 |
| 66 | 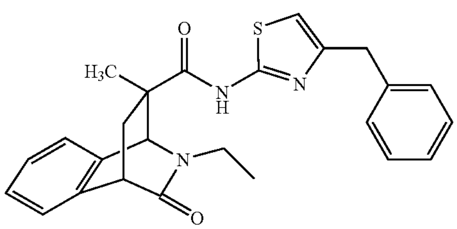 | 3.66 | 432 |

| Ex. # | Structure | Rt (min) | M/z (MH)+ |
|---|---|---|---|
| 67 | 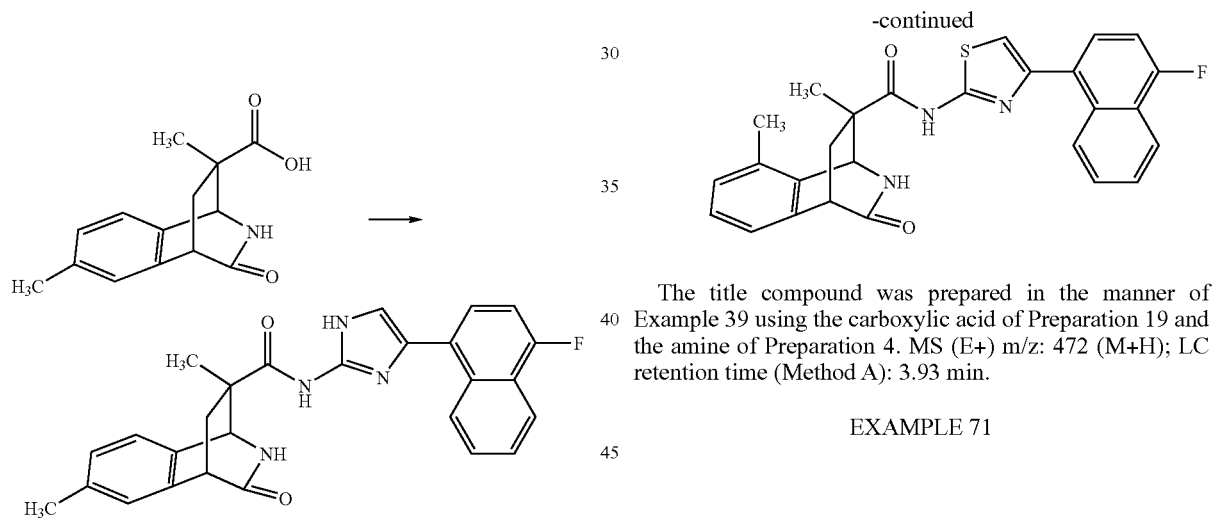 | 3.56 | 462 |
| 68 | 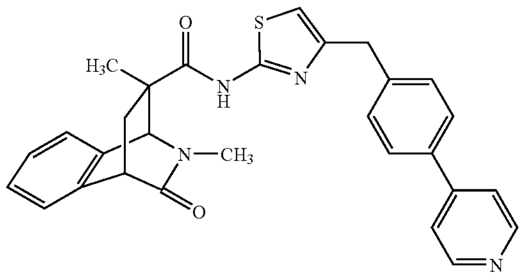 | 2.58 | 495 |

EXAMPLE 69

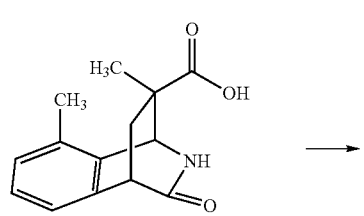

The title compound was prepared in the manner of Example 47 using the carboxylic acid of Preparation 18 and the amine of Preparation 5. MS (E+) m/z: 455 (M+H); LC retention time (Method A): 2.87 min.

EXAMPLE 70

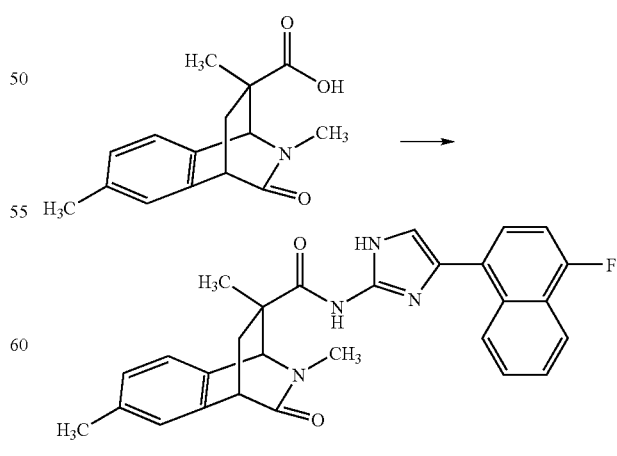

The title compound was prepared in the manner of Example 39 using the carboxylic acid of Preparation 19 and the amine of Preparation 4. MS (E+) m/z: 472 (M+H); LC retention time (Method A): 3.93 min.

EXAMPLE 71

The title compound was prepared in the manner of Example 47 using the carboxylic acid of Preparation 24 and the amine of Preparation 5. MS (E+) m/z: 469 (M+H); LC retention time (Method A): 3.02 min.

EXAMPLE 72

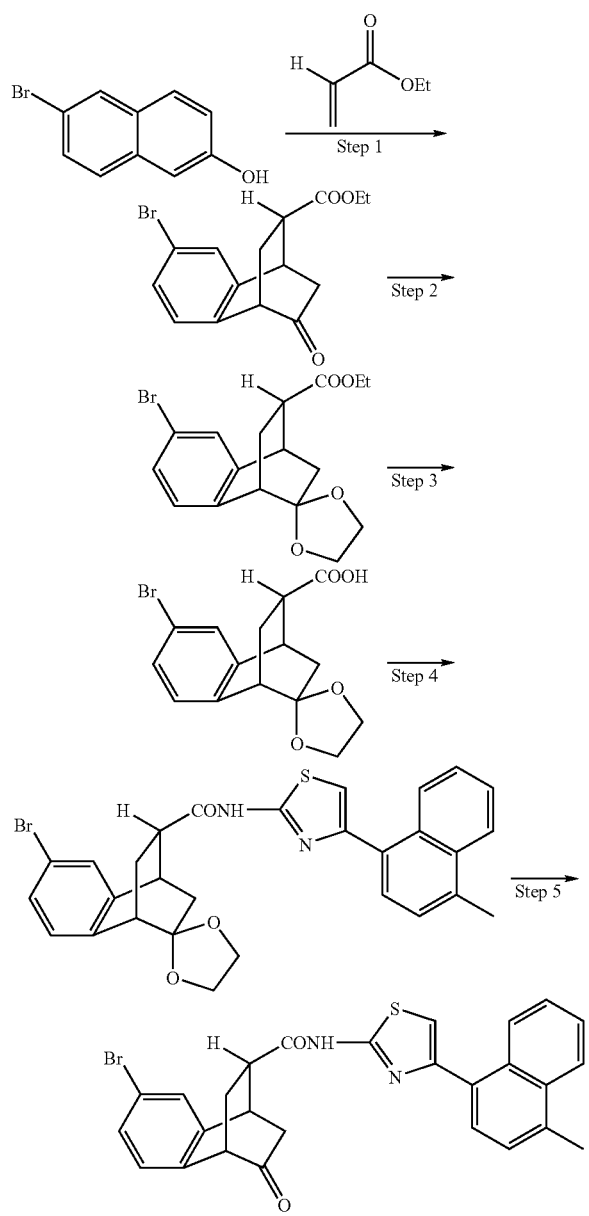

Step 1

The title compound was prepared in the manner described in J. Barrish et al., *Bioorganic and Medicinal Chemistry*, 1993, 1, 309-325 via the Diels-Alder reaction of 6-bromonaphthalen-2-ol (10 g, 44.8 mmol) and ethyl acrylate (9.42 ml, 86.9 mmol). The title compound (1.13 g, 7.8% yield) was isolated from a mixture of 4 isomeric products.

Step 2

The title compound was prepared in an analogous manner to the procedure described in described in J. Barrish et al., *Bioorganic and Medicinal Chemistry*, 1993, 1, 309-325 using the title compound of Step 1 (298.5 mg, 0.924 mmol) and ethane-1,2-diol to provide 275.2 mg (81% yield) of the title compound.

Step 3

The title compound was prepared in the manner of Step 2, Preparation 1, using the title compound of Step 2 (275.2 mg) to provide 129 mg (51% yield) of the title compound.

Step 4

The title compound was prepared in the manner of Example 1 using the title compound of Step 3 (129 mg) and 4-(4-methylnaphthalen-1-yl)thiazol-2-amine (101 mg).

Step 5

The title compound was prepared in the manner of Example 9 using the title compound of Step 4 to afford 17.5 mg of the title compound. LC/MS: m/z 516.98, 518.98 (M+1); HPLC retention time: 4.27 min (Method: 10-90% aqueous $CH_3OH$/0.1% $H_3PO_4$, 2.0 min gradient with 2 min hold; Column: Shimadzu VP-ODS; C-18 Ballistic, 4.6×50 mm (5 micron); 4.0 mL/min flow rate; and 220 nm detection wavelength.).

EXAMPLE 73

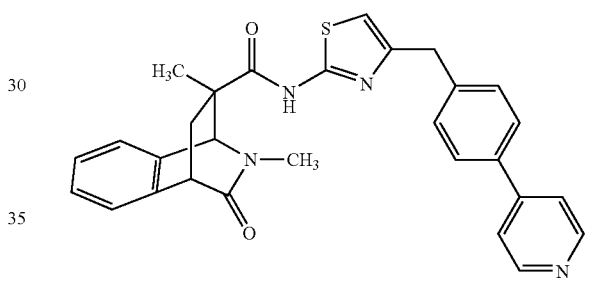

The title compound (homochiral) was prepared following the same procedure described above for the preparation of the title compound of example 68 using Enantiomer A carboxylic acid of Preparation 27. MS (E+) m/z: 495 (M+H); LC retention time (Method A): 2.60 min.

EXAMPLE 74

The title compound (homochiral enantiomer of the title compound of example 73) was prepared following the same procedure described above for the preparation of the title compound of example 73 using Enantiomer B carboxylic acid of Preparation 27. MS (E+) m/z: 495 (M+H); LC retention time (Method A): 2.60 min.

What is claimed is:

1. A compound of formula I:

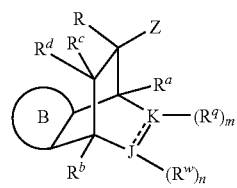

or all stereoisomers thereof, or a pharmaceutically acceptable salt thereof, wherein the compound of formula I is limited to formula BB as follows:

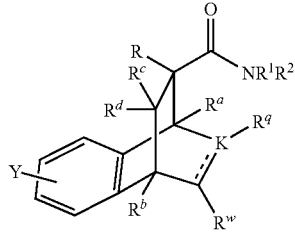

K is C;
Y is hydrogen, alkyl, aryl, arylalkyl, heteroaryl, heteroarylalkyl, halo, or alkoxy;
$R^1$ is

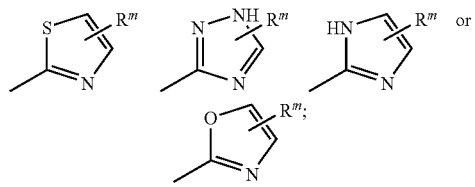

$R^m$ at each occurrence is independently selected from hydrogen, halogen, nitro, cyano, hydroxyl, alkoxy, —$CO_2$(alkyl), —C(O)N(alkyl)$_2$, alkyl, heteroarylalkyl, arylalkyl, aryl, and heteroaryl;

$R^2$ is elected from hydrogen, alkyl, alkenyl, alkynyl, alkoxy, amino, cycloalkyl, cycloalkylalkyl, aryl, heteroaryl, heteroarylalkyl, cycloheteroalkyl, cycloalkenyl, monoalkylaminoalkyl, dialkylaminoalkyl, cycloheteroalkylalkyl, hydroxyaryl, aryloxyalkyl, alkoxyalkyl, hydroxyalkyl, or a heterocyclic ring;

R is independently selected from hydrogen, alkyl, alkenyl, alkynyl, alkoxy, cyano, aryl, arylalkyl, aryloxy, heteroaryl, cycloheteroalkyl, heteroarylalkyl, cycloheteroalkylalkyl, cycloalkyl, cycloalkylalkyl, cyanoalkyl, aminoalkyl, hydroxyalkyl, aryloxyalkyl, hydroxyaryl or $NR^1R^2$, wherein $R^1$ and $R^2$ are the same or different and are independently selected from hydrogen, alkyl, alkenyl, alkynyl, alkoxy, amino, cycloalkyl, cycloalkylalkyl, aryl, heteroaryl, heteroarylalkyl, cycloheteroalkyl, cycloalkenyl, monoalkylaminoalkyl, dialkylaminoalkyl, cycloheteroalkylalkyl, hydroxyaryl, aryloxyalkyl, alkoxyalkyl, hydroxyalkyl, or a heterocyclic ring;

$R^a$ is hydrogen, halo, alkyl, alkenyl, alkynyl, alkoxy, aryl, aryloxy, heteroaryl, cycloheteroalkyl, heteroarylalkyl, cycloheteroalkylalkyl, cyano, heteroarylaminocarbonyl, cycloheteroalkylcarbonyl, cyanoalkyl, alkylaminoalkyl, hydroxyalkyl, hydroxyaryl, alkoxyalkyl, aryloxyalkyl, nitro, amino, CHO, $CO_2$ alkyl, $CONR^eR^f$, $CH_2NR^gR^h$, $CO_2H$, $CH_2OH$, $CH_2NRH$, $NR^gR^h$, $NHCH_2R^g$, $NHCHR^gR^h$, $NHCOR^e$, $NHCONR^eR^f$ or $NHSO_2R^eR^f$;

$R^b$ is hydrogen, alkyl, alkenyl, alkynyl, alkoxy, aryl, aryloxy, heteroaryl, cycloheteroalkyl, heteroarylalkyl, cycloheteroalkylalkyl, cyano, halo, heteroarylaminocarbonyl, cycloheteroalkylcarbonyl, cyanoalkyl, alkylaminoalkyl, hydroxyalkyl, alkoxyalkyl, nitro, amino, CHO, $CO_2$ alkyl, hydroxyaryl, aryloxyalkyl, $CONR^iR^j$, $CH_2NR^kR^l$, $CO_2H$, $CH_2OH$, $CH_2NHR^k$, $NHCH_2R^k$, $NR^kR^l$, $NHCHR^kR^l$, $NHCOR^i$, $NHCONR^iR^j$ or $NHSO_2R^i$;

$R^q$ and $R^w$ are the same or different and are independently selected from hydrogen, halo, hydroxy, alkyl, alkenyl, alkynyl, alkoxy, aryl, arylalkyl, aryloxy, heteroaryl, cycloheteroalkyl, heteroarylalkyl, cycloheteroalkylalkyl, cyano, heteroarylaminocarbonyl, cycloheteroalkylcarbonyl, cyanoalkyl, alkylaminoalkyl, hydroxyalkyl, hydroxyaryl, aryloxyalkyl, nitro, amino, CHO, $CO_2$ alkyl, $CONR^eR^f$, $CH_2NR^gR^h$, $CO_2H$, $CH_2OH$, $CH_2NHR^g$, $NR^gR^h$, $NHCH_2R^g$, $NHCHR^gR^h$, $NHCOR^e$, $NHCONR^eR^f$, $NHSO_2R^eR^f$, =O, =S, $SR^i$, $NHNR^kR^l$, $NHNR^kCO_2R^i$, $NHSO_2R^i$ or a heterocyclic ring;

where $R^e$ and $R^f$ are the same or different and are independently selected from hydrogen, aryl, alkyl, alkenyl, alkynyl, alkoxy, amino, alkoxyalkyl, alkylaminoalkyl, dialkylaminoalkyl, heteroaryl, cycloheteroalkyl, heteroarylalkyl, cycloheteroalkylalkyl, cycloalkyl, or cycloalkylalkyl, and $R^e$ and $R^f$ can be taken together with the nitrogen to which they are attached to form a 5-, 6- or 7-membered heteroaryl or cycloheteroalkyl ring which contains 1, 2 or 3 hetero atoms which can be N, O or S;

$R^g$ and $R^h$ are the same or different and are independently selected from hydrogen, aryl, alkyl, alkenyl, alkynyl, alkoxy, amino, alkoxyalkyl, alkylaminoalkyl, dialkylaminoalkyl, heteroaryl, cycloheteroalkyl, heteroarylalkyl, cycloheteroalkylalkyl, cycloalkyl, or cycloalkylalkyl, and $R^g$ and $R^h$ can be taken together with the nitrogen to which they are attached to form a 5-, 6- or 7-membered heteroaryl ring or cycloheteroalkyl ring which contains 1, 2 or 3 hetero atoms which can be N, O or S;

$R^i$ and $R^j$ are the same or different and are independently selected from hydrogen, aryl, alkyl, alkenyl, alkynyl, alkoxy, amino, alkoxyalkyl, alkylaminoalkyl, dialkylaminoalkyl, heteroaryl, cycloheteroalkyl, heteroarylalkyl, cycloheteroalkylalkyl, cycloalkyl, or cycloalkylalkyl, and $R^i$ and $R^j$ can be taken together with the nitrogen to which they are attached to form a 5-, 6-or 7-membered heteroaryl ring or cycloheteroalkyl ring which contains 1, 2 or 3 hetero atoms which can be N, O or S;

$R^k$ and $R^l$ are the same or different and are independently selected from hydrogen, aryl, alkyl, alkenyl, alkynyl, alkoxy, amino, alkoxyalkyl, alkylaminoalkyl, dialkylaminoalkyl, heteroaryl, cycloheteroalkyl, heteroarylalkyl, cycloheteroalkylalkyl, cycloalkyl, or cycloalkylalkyl, and $R^k$ and $R^l$ can be taken together with the nitrogen to which they are attached to form a 5-, 6- or 7-membered heteroaryl ring or cycloheteroalkyl ring which contains 1, 2 or 3 hetero atoms which can be N, O or S; and $R^c$ and $R^d$ are the same or different and are independently selected from hydrogen, alkyl, alkenyl, alkynyl, alkoxy, aryl, hydroxy, aryloxy, heteroaryl, cycloheteroalkyl, heteroarylalkyl, cycloheteroalkylalkyl, hydroxyaryl, or aryloxyalkyl; or $R^c$ and $R^d$ may optionally be taken together with the carbon to which they are attached to form a 3- to 7-membered ring which may optionally include an O atom or an N atom.

2. A compound as defined in claim 1, or all stereoisomers thereof, or a pharmaceutically acceptable salt thereof, where R is hydrogen, alkyl or hydroxyalkyl;

$R^a$ is selected from hydrogen, halo, alkyl, CN, NO$_2$, NH$_2$, CHO, CO$_2$ alkyl, CONR$^e$R$^f$, NR$^g$R$^h$ or CH$_2$NR$^g$R$^h$;

$R^b$ is selected from hydrogen, halo, alkyl, CN, NO$_2$, NH$_2$, CHO, CO$_2$ alkyl, CONR$^i$R$^j$, NR$^k$R$^l$, or CH$_2$NR$^k$R$^l$;

$R^q$ is hydrogen, halo, alkyl, aryl, arylalkyl, heteroaryl, heteroarylalkyl, CN, NO$_2$, NH$_2$, CHO, CO$_2$alkyl, CONR$^e$R$^f$, NR$^g$R$^h$, or CH$_2$NR$^g$R$^h$;

$R^w$ is hydrogen, hydroxy, alkyl, aryl, arylalkyl, heteroaryl, heteroarylalkyl, cyano, halo, nitro, amino, =O, =S, SR$^i$, CHO, CO$_2$ alkyl, CONR$^i$R$^j$, CH$_2$NR$^k$R$^l$, NR$^k$R$^l$, NHNR$^k$R$^l$, NHNR$^k$CO$_2$R$^i$, or a heterocyclic ring;

$R^c$ and $R^d$ are the same or different and are independently selected from hydrogen, alkyl, or hydroxy; and Y is selected from hydrogen, halo, or alkyl.

3. A compound as defined in claim 2, or all stereoisomers thereof, or a pharmaceutically acceptable salt thereof, wherein R is hydrogen or alkyl; $R^a$ is hydrogen; $R^b$ is independently hydrogen or alkyl; $R^c$ and $R^d$ are each hydrogen; and Y is hydrogen or alkyl.

4. A compound as defined in claim 1 or all stereoisomers thereof, or a pharmaceutically acceptable salt thereof, wherein R is hydrogen, alkyl, or hydroxyalkyl;

$R^b$ is selected from hydrogen, halo, alkyl, CN, NO$_2$, NH$_2$, CHO, CO$_2$ alkyl, CONR$^i$R$^j$, NR$^k$ or CH$_2$NR$^k$R$^l$;

$R^q$ is hydrogen, halo, alkyl, aryl, arylalkyl, heteroaryl, heteroarylalkyl, CN, NO$_2$, NH$_2$, CHO, CO$_2$ alkyl, CONR$^e$R$^f$, NR$^g$R$^h$ or CH$_2$NR$^g$R$^h$;

$R^w$ is hydrogen, hydroxy, alkyl, aryl, arylalkyl, heteroaryl, heteroarylalkyl, cyano, halo, nitro, amino, =O, =S, SR$^i$, CHO, CO$_2$ alkyl, CONR$^i$R$^j$, CH$_2$NR$^k$R$^l$, NR$^k$R$^l$, NHNR$^k$R$^l$, NHNR$^k$CO$_2$R$^i$, or a heterocyclic ring; and Y is selected from hydrogen, halo or alkyl.

5. A compound as defined in claim 4, or all stereoisomers thereof, or a pharmaceutically acceptable salt thereof, wherein R is hydrogen or alkyl;

$R^b$ is selected from hydrogen, halo, alkyl, CN, NO$_2$, NH$_2$, CHO, CO$_2$ alkyl, CONR$^i$R$^j$, NR$^k$R$^l$ or CH$_2$NR$^k$R$^l$;

$R^q$ is hydrogen, halo, alkyl, aryl, arylalkyl, heteroaryl, heteroarylalkyl, CN, NO$_2$, NH$_2$, CHO, CO$_2$ alkyl, CONR$^e$R$^f$, NR$^g$R$^h$ or CH$_2$NR$^g$R$^h$; and $R^w$ is hydrogen, hydroxy, alkyl, aryl, arylalkyl, heteroaryl, heteroarylalkyl, cyano, halo, nitro, amino, =O, =S, SR$^i$, CHO, CO$_2$ alkyl, CONR$^i$R$^j$, CH$_2$NR$^k$R$^l$, NR$^k$R$^l$, NHNR$^k$R$^l$, NHNR$^k$CO$_2$R$^i$, or a heterocyclic ring.

6. A compound as defined in claim 5, or all stereoisomers thereof, or a pharmaceutically acceptable salt thereof, wherein R is alkyl;

$R^b$ is hydrogen or alkyl;

$R^q$ is hydrogen, alkyl, aryl, arylalkyl, heteroaryl, or heteroarylalkyl;

$R^w$ is hydrogen, hydroxy, alkyl, aryl, arylalkyl, heteroaryl, heteroarylalkyl, =O, =S, SR$^i$, NR$^k$R$^l$, NHNR$^k$R$^l$, NHNR$^k$CO$_2$R$^i$, or a heterocyclic ring; and Y is hydrogen or alkyl.

7. A compound having the structure

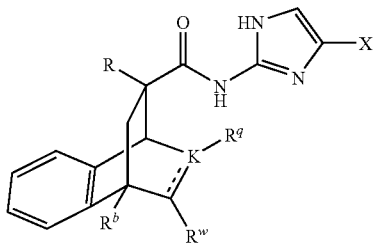

D or all stereoisomers thereof, or a pharmaceutically acceptable salt thereof, where K is C; R is alkyl; $R^b$ is hydrogen or alkyl; $R^q$ is hydrogen, alkyl, or arylalkyl; $R^w$ is hydroxy, =O, =S, SR$^i$, NR$^k$R$^l$, NHNR$^k$R$^l$, NHNR$^k$CO$_2$R$^i$, or a heterocyclic ring; and X is aryl, arylalkyl, alkyl, heteroaryl, or heteroarylalkyl; or

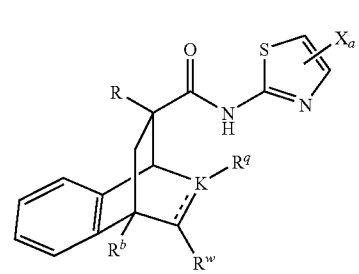

E or all stereoisomers thereof, or a pharmaceutically acceptable salt thereof, where K is C; R is alkyl; $R^b$ is hydrogen or alkyl; $R^q$ is hydrogen, alkyl, or arylalkyl; $R^w$ is hydroxy, =O, =S, SR$^i$, NR$^k$R$^l$, NHNR$^k$R$^l$, NHNR$^k$CO$_2$R$^i$, or a heterocyclic ring; and X$_a$ is aryl, arylalkyl, alkyl, heteroaryl, heteroarylalkyl or halo; or

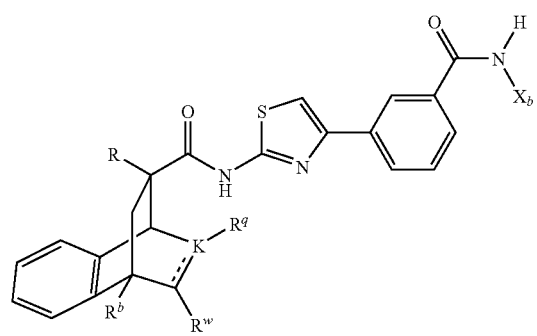

F or all stereoisomers thereof, or a pharmaceutically acceptable salt thereof, where K is C; R is alkyl; $R^b$ is hydrogen or alkyl; $R^q$ is hydrogen, alkyl, or arylalkyl; $R^w$ is hydroxy, =O, =S, SR$^i$, NR$^k$R$^l$, NHNR$^k$R$^l$, NHNR$^k$CO$_2$R$^i$, or a heterocyclic ring; and X$_b$ is aryl, arylalkyl, alkyl, heteroaryl, heteroarylalkyl or halo; or

G

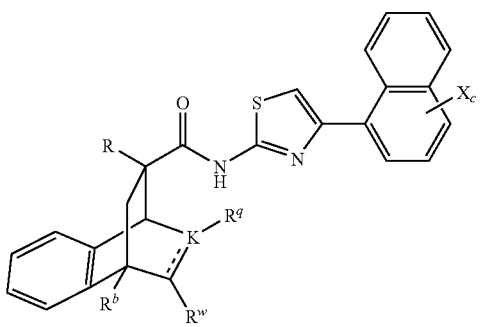

or all stereoisomers thereof, or a pharmaceutically acceptable salt thereof, where K is C;

H

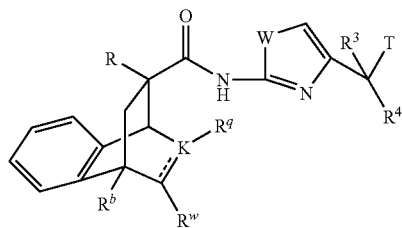

or or all stereoisomers thereof, or a pharmaceutically acceptable salt thereof, where W is S or NH; K is C; R is alkyl; $R^b$ is H, alkyl, nitro, formyl, $CO_2$alkyl, amino, halo, and CN; $R^q$ is hydrogen, alkyl, or arylalkyl; $R^w$ is hydroxy, =O, =S, $SR^i$, $NR^kR^i$, $NHNR^kR^i$, $NHNR^kCO_2R^i$, or a heterocyclic ring; and $X_a$ is aryl, arylalkyl, alkyl, heteroaryl, heteroarylalkyl or halo;

T is a cycloalkyl, cycloalkenyl, heterocycloalkyl, aryl, or heteroaryl ring, each ring substituted by 0-4 $R^5$ and 0-1 $R^6$;

$R^3$ and $R^4$ are independently at each occurrence hydrogen, halogen, hydroxy, alkyl, alkenyl, alkynyl, alkoxy, cyano, nitro, $NR^eR^f$, or CHO provided that if M is $CR^m$, X is S, and either of $R^3$ and $R^4$ is alkyl, alkenyl, or alkynyl, then the other of $R^3$ and $R^4$ is not alkyl, alkenyl, or alkynyl;

or $R^3$ and $R^4$ combine to form =O or a =C, wherein the carbon of =C is substituted by hydrogen, aryl, alkyl, alkenyl, alkynyl, alkoxy, amino, substituted amino, alkoxyalkyl, alkylaminoalkyl, dialkylaminoalkyl, heteroaryl, cycloheteroalkyl, heteroarylalkyl, cycloheteroalkylalkyl, cycloalkyl, or cycloalkylalkyl; and $R^5$ and $R^6$ are, independently at each occurrence, hydrogen, halogen, hydroxy, alkyl, alkenyl, alkynyl, alkoxy, aryl, aryloxy, heteroaryl, cycloheteroalkyl, heteroarylalkyl, cycloheteroalkylalkyl, cyano, heteroarylaminocarboyl, cycloheteroalkylcarbonyl, cyanoalkyl, alkylaminoalkyl, hydroxyalkyl, hydroxyaryl, aryloxyalkyl, nitro, oxo, $NR^eR^f$, CHO, $CO_2$ alkyl, hydroxyaryl, aryloxyalkyl, $CONR^eR^f$, $CH_2NR^eR^f$, $CO_2H$, $CH_2OH$, $CH_2NHC(O)R^eR^f$, $NHCOR^i$, $NHCONR^eR^f$, $NHSO_pR^i$, —$SO_2NR^eR^f$, $NR^eSO_2NR^eR^f$, or $NR^eSO_pR^i$;

or $R^5$ and $R^6$ located on adjacent atoms can be taken together to form an optionally substituted cycloalkyl, aryl, heteroaryl, or cycloheteroalkyl ring.

8. A compound as defined in claim 7 having the structure

D

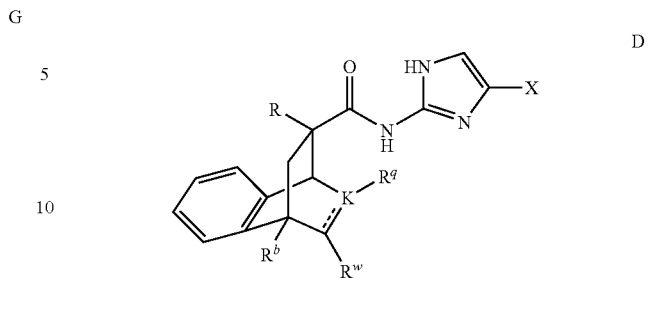

or all stereoisomers thereof, or a pharmaceutically acceptable salt thereof, where K is C; R is $CH_3$; $R^b$ is hydrogen or $CH_3$; $R^q$ is hydrogen, $CH_3$, $C_2H_5$, or benzyl; $R^w$ is hydroxy, =O, =S, $SCH_3$, $NHC_3H_7$, $NHNH(C_6H_5)$, $NHNHCO_2C_2H_5$ or dioxolanyl; and X is 1-naphthyl, 1-(4-methyl)naphthyl, 1-(4-fluoro)naphthyl, 1-(6-methoxy)naphthyl, benzyl, or phenyl, t-butyl; or

E

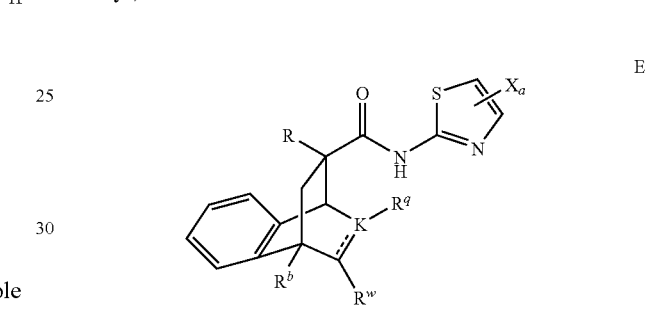

or all stereoisomers thereof, or a pharmaceutically acceptable salt thereof, where K is C; R is $CH_3$; $R^b$ is hydrogen or $CH_3$; $R^q$ is hydrogen, $CH_3$, $C_2H_5$, or benzyl; $R^w$ is hydroxy, =O, =S, $SCH_3$, $NHC_3H_7$, $NHNH(C_6H_5)$, $NHNHCO_2C_2H_5$ or dioxolanyl; and $X_a$ is phenyl, benzyl, t-butyl, 1-naphthyl, 1-(4-fluoro)naphthyl, benzthiophen-3-yl, 1-(4-methyl)naphthyl, 1-(2-methoxy)naphthyl, 1-(6-methoxy)naphthyl, 3-fluorophenyl, 4-fluorophenyl, 3-methylphenyl, 2-chlorophenyl, 1-(4-methoxy)naphthyl, 1-(4-bromo)naphthyl, 1-(4-iodo)naphthyl, 5-anthracenyl, 1-anthracenyl, 4-quinolin-1-yl 2-quinolin-1-yl, 1-(4-cyano)naphthyl, 5-iodo, 4-benzthiophenyl, 1-(2-hydroxy)naphthyl, 1-(6-hydroxy)naphthyl, 1-(4-hydroxy)naphthyl; or

F

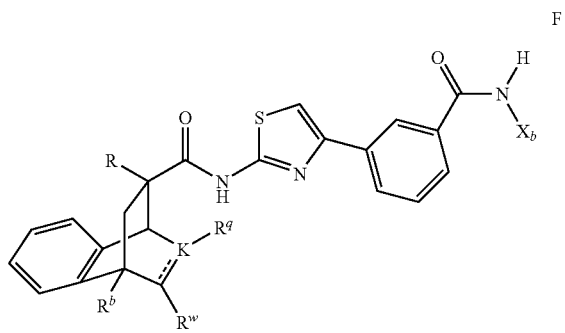

or all stereoisomers thereof, or a pharmaceutically acceptable salt thereof, where K is C; R is $CH_3$; $R^b$ is hydrogen or $CH_3$; $R^q$ is hydrogen, $CH_3$, $C_2H_5$, or benzyl; $R^w$ is hydroxy, =O, =S, $SCH_3$, $NHC_3H_7$, $NHNH(C_6H_5)$, $NHNHCO_2C_2H_5$ or dioxolanyl; and $X_b$ is phenyl, 3-methoxyphenyl, 4-methoxyphenyl, 2,5-dimethoxyphenyl, 3,5-dimethoxyphenyl, 3-pyridyl, 2-(4-pyridyl)ethyl, 2-(4-imidazolyl)ethyl, 3-chloro-4-methoxyphenyl, 3-hydroxy-4-methoxyphenyl, 3-fluoro-4-methoxyphenyl, 3,4,5-trimethoxyphenyl, 3,4-dimethoxyphenyl, 4-methyl-3-methoxyphenyl, 3-methoxyphenyl, 3,5-dimethoxyphenyl, 2,3-dimethoxyphenyl, 4-chlorophenyl, 2-napthyl, 3-chlorophenyl, 3,4-dichlorophenyl, 4-azidophenyl, 2,4-dimethoxyphenyl, 3-ethoxyphenyl, 3-(methylthio)phenyl, 4-(methylthio)phenyl, 3-(acetylenyl)phenyl, 4-methoxy-3-pyridyl, 3-cyanophenyl, 2-methyl-4-methoxyphenyl, 3-azidophenyl, 3-methyl-isothiazolyl, 1-methyl-pyrazol -5-yl, 5-trifluoromethyl-1,3,4-thiadiazol-2-yl; or

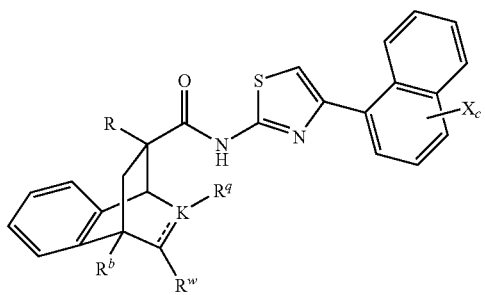

G or all stereoisomers thereof, or a pharmaceutically acceptable salt thereof, where K is C; R is $CH_3$; $R^b$ is hydrogen or $CH_3$; $R^1$ is hydrogen, $CH_3$, $C_2H_5$, or benzyl; $R^w$ is hydroxy, =O, =S, $SCH_3$, $NHC_3H_7$, $NHNH(C_6H_5)$, $NHNHCO_2C_2H_5$ or dioxolanyl; and $X_c$ is hydrogen, $CH_3$, or F; or

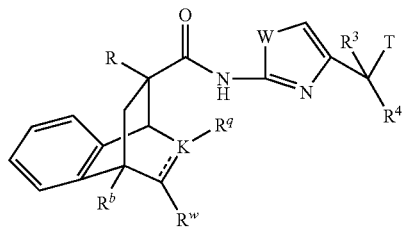

H or all stereoisomers thereof, or a pharmaceutically acceptable salt thereof, where W is S or NH; K is C; R is alkyl; $R^b$ is H, $C_{1-4}$alkyl, halo, and CN; $R^q$ is hydrogen, alkyl, or arylalkyl; $R^w$ is hydroxy, =O, =S, $SR^i$, $NR^kR^l$, $NHNR^kR^l$, $NHNR^kCO_2R^i$, or a heterocyclic ring; and $X_a$ is aryl, arylalkyl, alkyl, heteroaryl, heteroarylalkyl or halo; W is S or NH; Q is CH;

T is a phenyl, naphthyl, pyrimidyl, pyridinyl, pyridazinyl, piperazinyl, thiophenyl, thiazolyl, isoxazolyl, or imidazolyl ring;

$R^3$ is hydrogen, halogen, or hydroxy; and $R^4$ is hydrogen, halogen, hydroxy, alkyl, alkenyl, alkynyl, alkoxy, cyano, nitro, $NR^eR^f$, or CHO;

or $R^3$ and $R^4$ combine to form =O or a double bond, wherein the double bond is substituted by hydrogen, aryl, alkyl, alkenyl, alkynyl, alkoxy, amino, substituted amino, alkoxyalkyl, alkylaminoalkyl, dialkylaminoalkyl, heteroaryl, heterocycloalkyl, heteroarylalkyl, heterocycloalkylalkyl, cycloalkyl, or cycloalkylalkyl;

$R^5$ and $R^6$ are independently at each occurrence:
(a) hydrogen, bromo, chloro, fluoro, $C_{1-4}$alkyl, arylalkyl, $OR^7$, oxo, $NO_2$, cyano, $NH_2$, $-NHC_{1-4}$alkyl, $-N(C_{1-4}$alkyl$)_2$, $SO_2C_{1-4}$alkyl, $-NHC(O)C_{1-4}$alkyl, $-C(O)N(C_{1-4}$alkyl$)_2$, $-C(O)NH(C_{1-4}$alkyl$)$, $-C(O)NH_2$, $CO_2H$, $-CO_2(C_{1-4}$alkyl$)$, arylalkyl; or
(b) a phenyl, naphthyl, pyrazolyl, pyrimidinyl, pyridinyl, isoxazolyl, indolyl, or morpholinyl ring; each of which is optionally further substituted by 1-3 $R^8$;
or $R^5$ and $R^6$ located on adjacent atoms can be taken together to form a dioxole or phenyl ring, where each ring is optionally further substituted;

$R^7$ at each occurrence is selected from hydrogen, $C_{1-4}$alkyl, $(CH_2)_vC(O)NH_2$, $(CH_2)_v$heteroaryl, $(CH_2)_vO(CH_2)_yO(CH_2)_zOR^9$, $(CH_2)_vN(C_{1-4}$alkyl$)_2$,$(CH_2)_v$heterocycloalkyl, or $(CH_2)_v$phenyl;

$R^8$ is halogen, oxo, $NH_2$, hydroxy, $C_{1-4}$alkyl, $C_{1-4}$alkoxy, $-(CH_2)$aryl, or heterocycloalkyl;

$R^9$ is hydrogen or $C_{1-4}$alkyl;
and
v, y and z are independently at each occurrence selected from 0, 1 or 2.

9. A compound having the structure

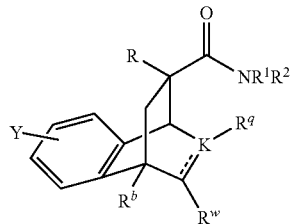

C including all stereoisomers thereof, or a pharmaceutically acceptable salt thereof, or a solvate thereof, where K is C; Y is H or $CH_3$; R is $CH_3$, $C_2H_5$ or 2-hydroxyethyl; $R_b$ is hydrogen or $CH_3$; and one of $R^1$ and $R^2$ is H and the other of $R^1$ and $R^2$ is benzothiazol-2-yl, alkylbenzothiazol-2-yl, alkoxybenzothiazol-2-yl, halobenzothiazol-2-yl, thiazol-2-yl, 4-(1-naphthyl)thiazol-2-yl, 2-quinolin-1-yl, or a thiazole which is optionally substituted with heteroarylthio, heteroaryl, dialkyl, alkyl, aryl where the aryl may be optionally substituted with halo, alkyl, nitro, hydroxy, alkoxy, dialkoxy, carboxy, alkylaminocarbonyl, arylaminocarbonyl, hydroxyalkylaminocarbonyl, cycloheteroalkylcarbonyl, alkoxyalkylaminocarbonyl, heteroarylaminocarbonyl.

10. The compound as defined in claim 9, having the structure

E including all stereoisomers thereof, or a pharmaceutically acceptable salt thereof, or a solvate thereof, where $X_a$ is 4,5-dimethyl, 5-chloro, 4-methyl, 5-methyl, 4-phenyl, 4-(1- naphthyl), 4-(2-naphthyl), 4-(4-fluoronaphth-1-yl), 4-(4-methylnaphth-1-yl), 4-(3-nitrophenyl), 4-(6-hydroxynaphth-1-yl), 4-[(1,2,4-triazol-5-yl)thio]methyl, 4-benzoic acid, 4-(4-bromonaphth-1-yl), 4-(N-ethyl) benzamide, 4-(N-2-methoxyphenyl)benzamide, 4-(N-methyl-N-2-hydroxyethyl)benzamide, 4-(N-(pyrrolidinyl)benzamide, 4-(N-morpholinyl)benzamide, 4-(N-phenyl-N-methyl)benzamide, 3-(N-ethyl)benzamide, 3-(N-2-methoxyphenyl)benzamide, 3-(N-2-methoxyethyl)benzamide, 3-(N-methyl-N-2-hydroxyethyl)benzamide, 3-(N-methyl-N-phenyl)benzamide, 3-(N-4-acetylpiperaziny-1-yl) benzamide, 3-(N-3-methoxypropyl)benzamide, 2-(6-carboxy)pyridine, 3-(N-3-hydroxy-4-methoxyphenyl)benzamide, 3-(N-3-fluoro-4-methoxyphenyl)benzamide, 3-(N-2,3-dimethoxyphenyl)benzamide, 3-(N-3-dimethoxyphenyl)benzamide, 3-(N-5-trifluormethyl-1,3,4-thiadiazol-2-yl)benzamide, 3-(N-5-methyl-1,3,4-thiadiazol-2-yl)benzamide, 3-(N-5-chlorobenzoxazol-2-yl)benzamide, 3-(N-3-benzonitrile) benzamide, 3-(N-4-methoxypyrid-3-yl)benzamide, 5-(1,4-benzodioxane), 4-(1,3-benzodioxole).

11. The compound as defined in claim 1 having the structure:

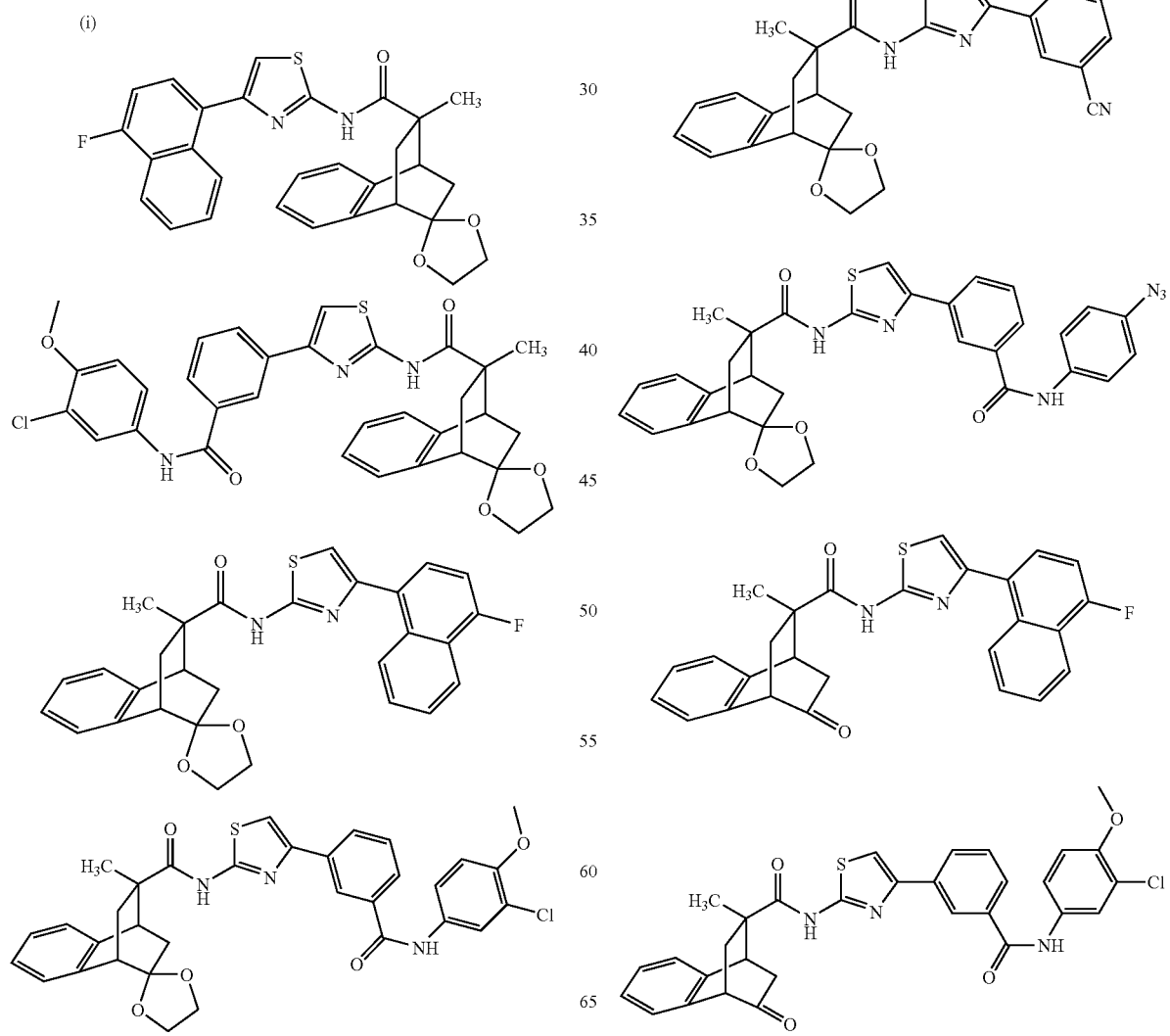

-continued
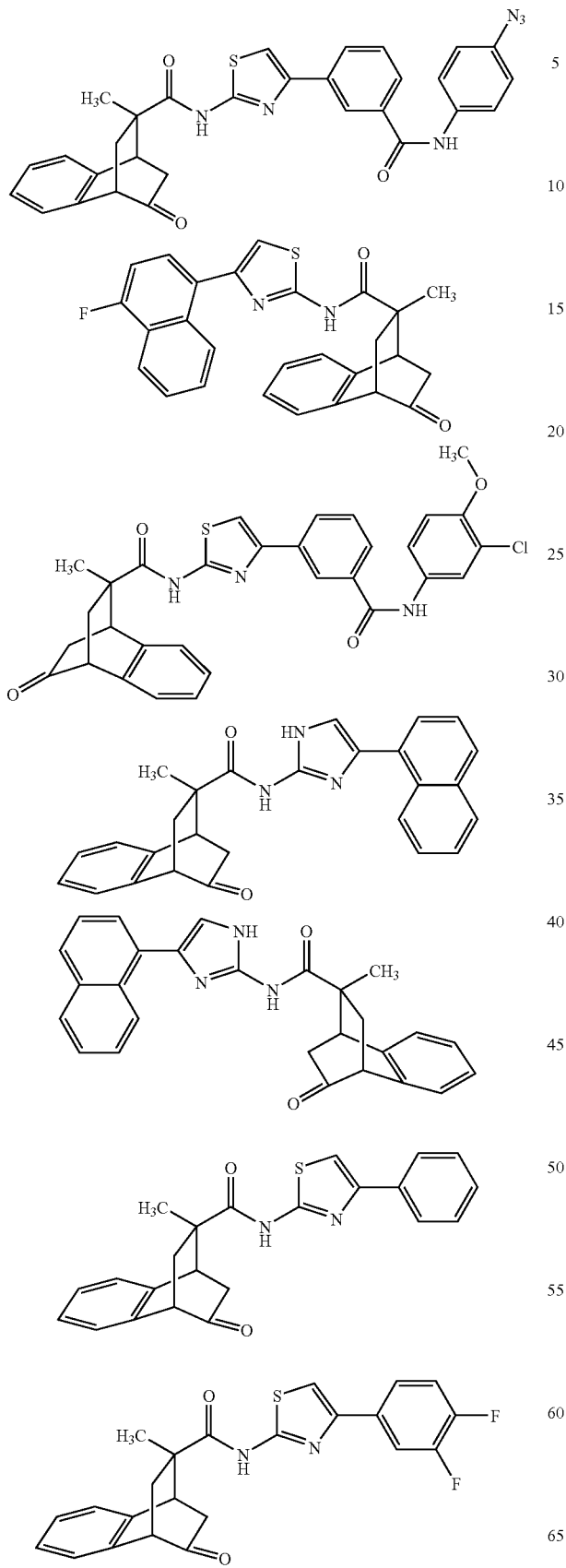
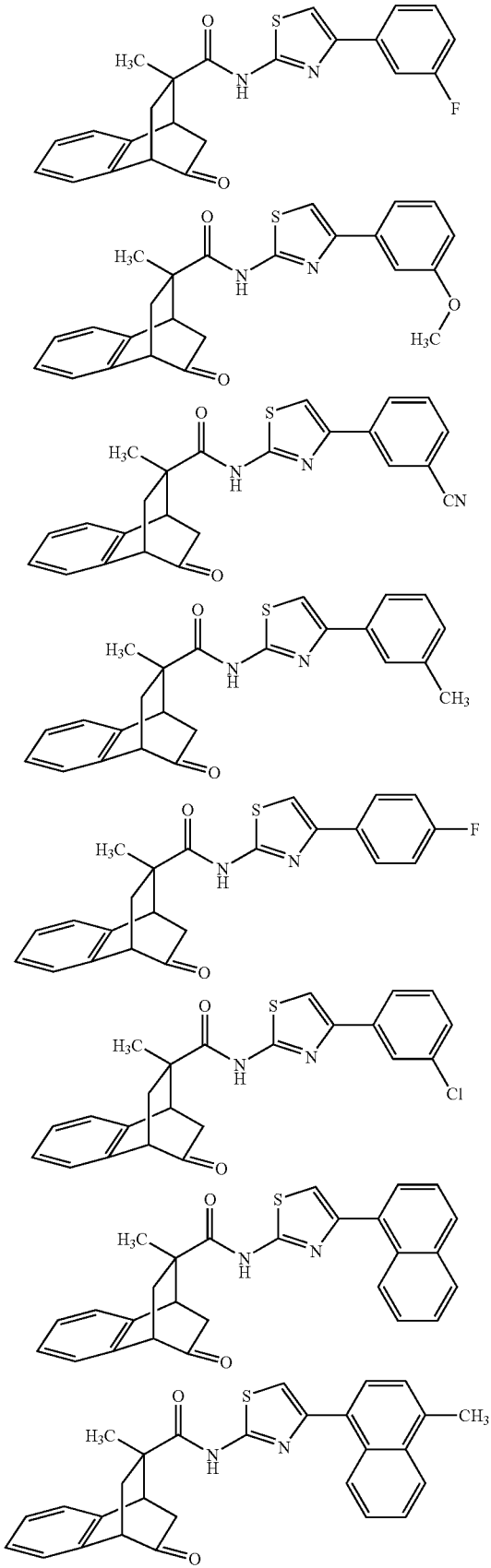

-continued

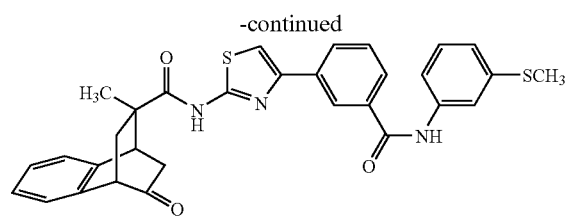
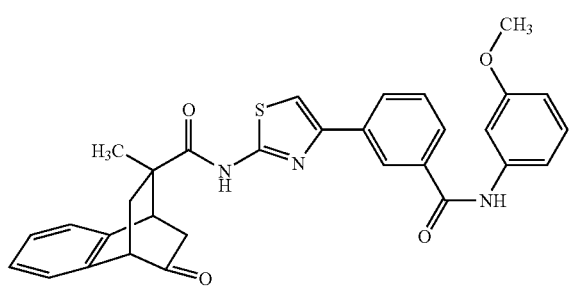
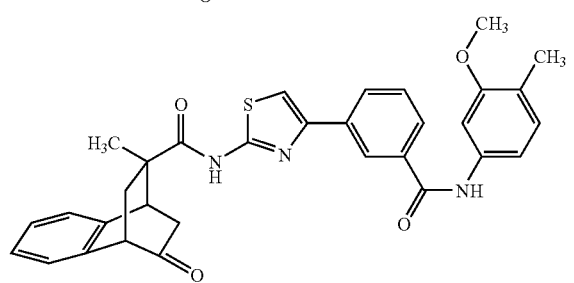
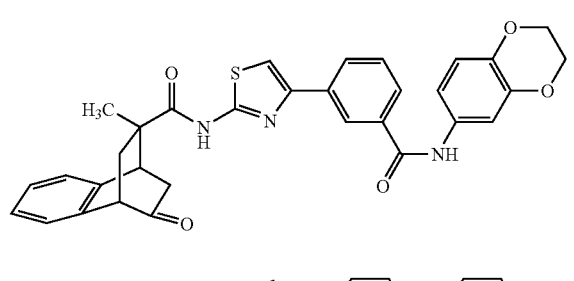
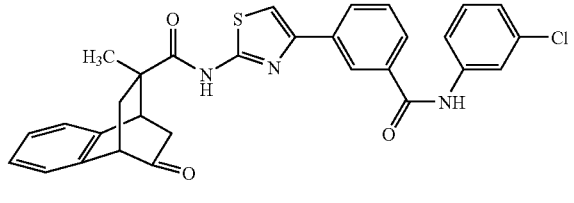
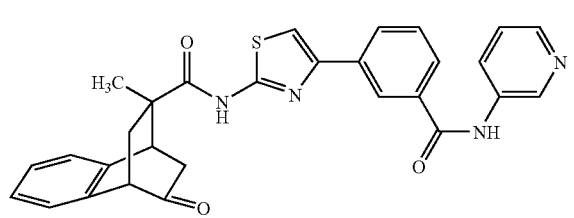
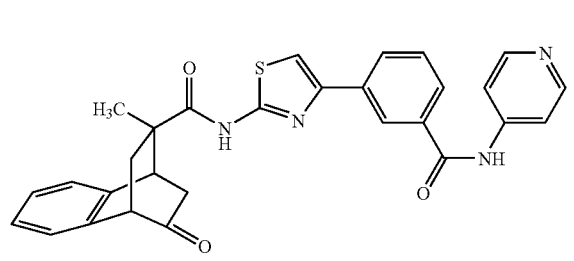

-continued

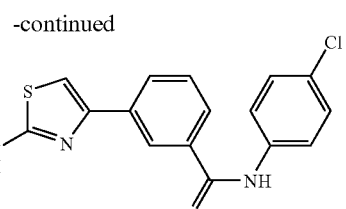
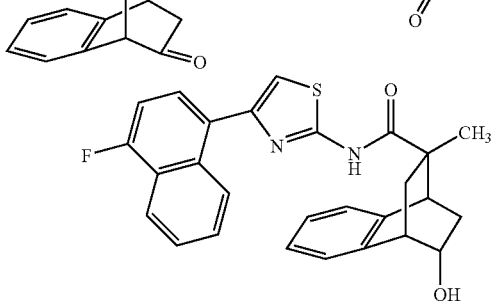
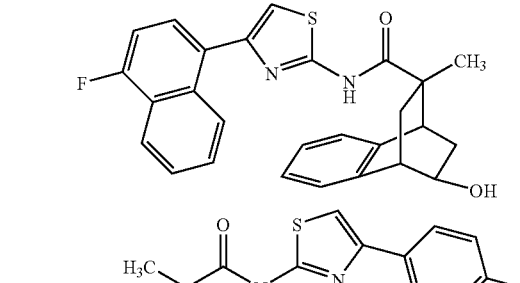
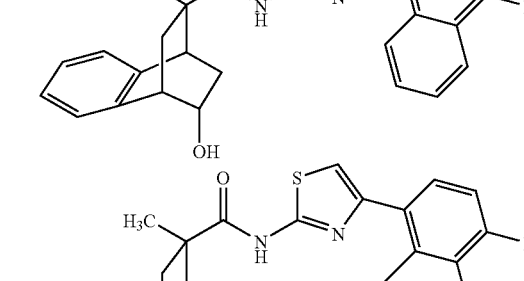
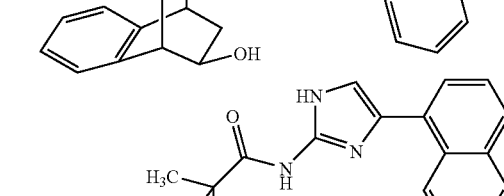
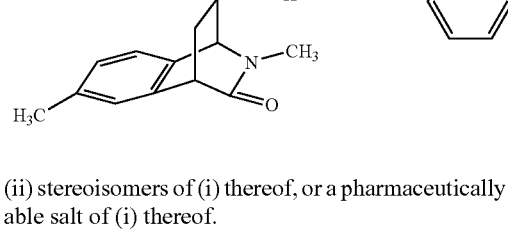
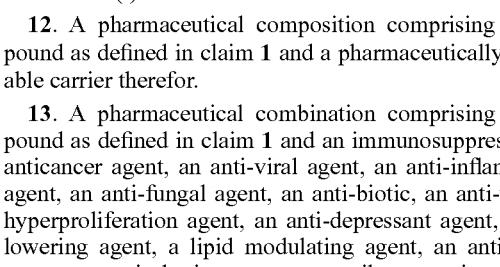

(ii) stereoisomers of (i) thereof, or a pharmaceutically acceptable salt of (i) thereof.

12. A pharmaceutical composition comprising a compound as defined in claim 1 and a pharmaceutically acceptable carrier therefor.

13. A pharmaceutical combination comprising a compound as defined in claim 1 and an immunosuppressant, an anticancer agent, an anti-viral agent, an anti-inflammatory agent, an anti-fungal agent, an anti-biotic, an anti-vascular hyperproliferation agent, an anti-depressant agent, a lipid-lowering agent, a lipid modulating agent, an antidiabetic agent, an anti-obesity agent, an antihypertensive agent, a platelet aggregation inhibitor, and/or an antiosteoporosis agent, wherein the antidiabetic agent is 1, 2, 3 or more of a biguanide, a sulfonyl urea, a glucosidase inhibitor, a PPARγ agonist, a PPAR α/γ dual agonist, an SGLT2 inhibitor, a DP4inhibitor, an aP2inhibitor, an insulin sensitizer, a glucagon-like peptide-1 (GLP-1), insulin and/or a meglitinide, wherein the anti-obesity agent is a beta 3 adrenergic agonist, a lipase inhibitor, a serotonin (and dopamine) reuptake inhibitor, a thyroid receptor agonist, an aP2 inhibitor and/or an anorectic agent, wherein the lipid lowering agent is an MTP inhibitor, an HMG CoA reductase inhibitor, a squalene synthetase inhibitor, a fibric acid derivative, an upregulator of LDL receptor activity, a lipoxygenase inhibitor, or an ACAT inhibitor, wherein the antihypertensive agent is an ACE inhibitor, angiotensin II receptor antagonist, NEP/ACE inhibitor, calcium channel blocker and/or β-adrenergic blocker.

14. The combination as defined in claim 13 wherein the antidiabetic agent is 1, 2, 3 or more of metformin, glyburide, glimepiride, glipyride, glipizide, chlorpropamide, gliclazide, acarbose, miglitol, pioglitazone, troglitazone, rosiglitazone, insulin, Gl-262570, isaglitazone, JTT-501, NN-2344, L895645, YM-440, R-119702, AJ9677, repaglinide, nateglinide, KAD1129, AR-HO 39242, GW-409544, KRP297, AC2993, LY315902, P32/98 and/or NVP-DPP-728A, wherein the anti-obesity agent is orlistat, ATL-962, AJ9677, L750355, CP331648, sibutramine, topiramate, axokine, dexamphetamine, phentermine, phenylpropanolamine, and/or mazindol, wherein the lipid lowering agent is pravastatin, lovastatin, simvastatin, atorvastatin, cerivastatin, fluvastatin, itavastatin, visastatin, fenofibrate, gemfibrozil, clofibrate, avasimibe, TS-962, MD-700, cholestagel, niacin and/or LY295427, wherein the antihypertensive agent is an ACE inhibitor which is captopril, fosinopril, enalapril, lisinopril, quinapril, benazepril, fentiapril, ramipril or moexipril; an NEP/ACE inhibitor which is omapatrilat, [S[(R*,R*)]-hexahydro-6-[(2-mercapto-1-oxo-3-phenylpropyl)amino]-2, 2-dimethyl-7-oxo-1H-azepine-1-acetic acid (gemopatrilat) or CGS 30440;

an angiotensin II receptor antagonist which is irbesartan, losartan or valsartan;

amlodipine besylate, prazosin HCl, verapamil, nifedipine, nadolol, propranolol, carvedilol, or clonidine HCl, wherein the platelet aggregation inhibitor is aspirin, clopidogrel, ticlopidine, dipyridamole or ifetroban;

the immunosuppressant is a cyclosporin, mycophenolate, interferon-beta, deoxyspergolin, FK-506 or Ant.-IL-2;

the anti-cancer agent is azathiprine, 5-fluorouracel, cyclophosphamide, cisplatin, methotrexate, thiotepa, or carboplatin;

the anti-viral agent is abacavir, aciclovir, ganciclovir, zidanocin, or vidarabine; and the antiinflammatory drug is ibuprofen, celecoxib, rofecoxib, aspirin, naproxen, ketoprofen, diclofenac sodium, indomethacin, piroxicam, prednisone, dexamethasone, hydrocortisone, or triamcinolone diacetate.

* * * * *

UNITED STATES PATENT AND TRADEMARK OFFICE
CERTIFICATE OF CORRECTION

PATENT NO.        : 7,544,808 B2
APPLICATION NO.   : 11/773506
DATED             : June 9, 2009
INVENTOR(S)       : David S. Weinstein et al.

It is certified that error appears in the above-identified patent and that said Letters Patent is hereby corrected as shown below:

In the Claims:

Claim 1:
  Column 112, line 42, change "6-or" to -- 6- or --.

Claim 2:
  Column 113, line 10, change "heteroarylalkyl,cyano," to -- heteroarylalkyl, cyano, --.

Claim 4:
  Column 113, line 29, change "$NR^k$" to -- $NR^kR^l$ --.

Claim 7:
  Column 115, line 18, after "C;", insert -- or --.

Column 115, line 25, after " 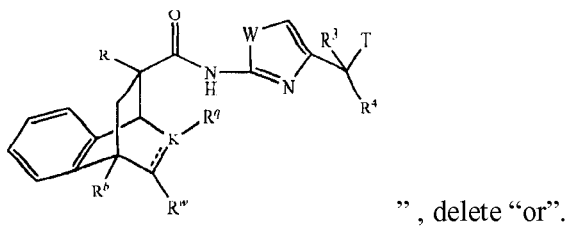 ", delete "or".

Column 115, lines 57 and 58, change "heteroarylaminocarboyl," to -- heteroarylaminocarbonyl, --.

In the Claims:

Claim 8:
  Column 116, line 45, after "4-quinolin-1-yl", insert -- , --.

Column 117, line 8, change "2-napthyl," to -- 2-naphthyl, --.

Signed and Sealed this
Eighth Day of November, 2011

David J. Kappos
Director of the United States Patent and Trademark Office

CERTIFICATE OF CORRECTION (continued)

U.S. Pat. No. 7,544,808 B2

Page 2 of 2

Column 117, line 13, change "1-methyl-pyrazol -5-yl" to -- 1-methyl-pyrazol-5-yl --.

Column 117, line 32, change "$R^1$" to -- $R^q$ --.

Claim 10:
Column 119, line 18, change "trifluormethyl" to -- trifluoromethyl --.

Claim 13:
Column 125, line 5, change "DP4inhibitor, an aP2inhibitor," to -- DP4 inhibitor, an aP2 inhibitor, --.

Claim 14:
Column 126, lines 7 and 8, change "[S[(R*,R*)]-hexahydro-6-[(2-mercapto-1-oxo-3-phenylpropyl)amino]-2,2-dimethyl-7-oxo-1H-azepine-l-acetic acid" to --[S[(R*,R*)]-hexahydro-6-[(2-mercapto-1-oxo-3-phenylpropyl)amino]-2,2-dimethyl-7-oxo-1H-azepine-1]-acetic acid --.

Column 126, line 18, change "deoxyspergolin," to -- deoxyspergualin, --.

Column 126, line 19, change "azathiprine, 5-fluorouracel," to -- azathioprine, 5-fluorouracil, --.